United States Patent
Sloan

(10) Patent No.: US 9,550,744 B2
(45) Date of Patent: Jan. 24, 2017

(54) VITAMIN C PRODRUGS AND USES THEREOF

(71) Applicant: University of Florida Research Foundation, Inc., Gainesville, FL (US)

(72) Inventor: Kenneth B. Sloan, Gainesville, FL (US)

(73) Assignee: University of Florida Research Foundation, Inc., Gainesville, FL (US)

(*) Notice: Subject to any disclaimer, the term of this patent is extended or adjusted under 35 U.S.C. 154(b) by 0 days.

(21) Appl. No.: 15/024,504

(22) PCT Filed: Sep. 24, 2014

(86) PCT No.: PCT/US2014/057198
§ 371 (c)(1),
(2) Date: Mar. 24, 2016

(87) PCT Pub. No.: WO2015/048121
PCT Pub. Date: Apr. 2, 2015

(65) Prior Publication Data
US 2016/0264541 A1 Sep. 15, 2016

Related U.S. Application Data

(60) Provisional application No. 61/882,503, filed on Sep. 25, 2013.

(51) Int. Cl.
| C07D 307/62 | (2006.01) |
| C07D 405/04 | (2006.01) |
| C07D 407/14 | (2006.01) |

(52) U.S. Cl.
CPC .......... *C07D 307/62* (2013.01); *C07D 405/04* (2013.01); *C07D 407/14* (2013.01)

(58) Field of Classification Search
CPC .... C07D 307/62; C07D 407/14; C07D 405/04
See application file for complete search history.

(56) References Cited

U.S. PATENT DOCUMENTS

| 4,340,603 A | 7/1982 | Bodor et al. |
| 4,552,888 A | 11/1985 | Koppel et al. |
| 5,417,662 A | 5/1995 | Hjertman et al. |
| 5,527,288 A | 6/1996 | Gross et al. |
| 6,346,254 B1 | 2/2002 | Streicher et al. |
| 2003/0181436 A1 | 9/2003 | Sakalosky |
| 2005/0095707 A1 | 5/2005 | Carpenter et al. |
| 2005/0234025 A1 | 10/2005 | Kutney et al. |
| 2007/0167517 A1 | 7/2007 | Kvitnitsky et al. |
| 2008/0305039 A1 | 12/2008 | Kraus et al. |
| 2012/0076744 A1 | 3/2012 | Poigny et al. |

FOREIGN PATENT DOCUMENTS

| FR | 2913686 A1 * | 9/2008 | ............ A61K 8/676 |
| IL | WO 03010173 A1 * | 2/2003 | ............ A61K 8/676 |
| IL | WO 2004094369 A2 * | 11/2004 | ............ A23L 1/302 |

OTHER PUBLICATIONS

International Search Report and Written Opinion, mailed Dec. 15, 2014, in connection with PCT/US2014/057198.
International Preliminary Report on Patentability, mailed Apr. 7, 2016, in connection with PCT/US2014/057198.
Berge et al.., Pharmaceutical salts. J Pharm Sci. Jan. 1977;66(1):1-19.
Block, Epidemiologic evidence regarding vitamin C and cancer. American Journal of Clinical Nutrition. 1991;54(6Suppl):1310S-14S.
Bundgaard, Design of Prodrugs. Elsevier. 1985;7-9, 21-24.
Bundgaard, Novel chemical approaches in prodrug design. Drugs of the Future. 1991;16(5):443-458.
Gould, Salt selection for basic drugs. Int. J Pharma. Nov. 1986;33:201-217.
Hadgraft et al., Formulation Fantasies: A Discussion. Cosmetics & Toiletries. Jul. 2013;128(7):480-483.
Hill et al., Catalytic replacement of unactivated alkane carbonhydrogen bonds with carbon-X bonds (X = nitrogen, oxygen, chlorine, bromine, or iodine). Coupling of intermolecular hydrocarbon activation by MnIIITPPX complexes with phase-transfer catalysis. J. Org. Chem. 1983;48:3277-3281.
Jackson et al.., Synthesis of 3-hexuloses. Can. J. Chem. 1969;47:2498-2501.
Jung et al.., Total synthesis of (R)-glycerol acetonide and the antiepileptic and hypotensive drug (-)-.gamma.-amino-.beta.-hydroxybutyric acid (GABOB): Use of vitamin C as a chiral starting material. J. Am. Chem. Soc. 1980;102:6304-6311.
Juntunen et al.., The effect of water solubility of solutes on their flux through human skin in vitro: a prodrug database integrated into the extended Flynn database. Int J Pharm. Mar. 3, 2008;351(1-2):92-103. Epub Sep. 29, 2007.
Krowka, The Importance of Formaldehyde—donor Preservatives in Personal Care Products. Cosmetics & Toiletries. Jul. 2013;128(7):474-476.
Majumdar et al.., Prodrugs of theophylline incorporating ethyleneoxy groups in the promoiety: synthesis, characterization, and transdermal delivery. AAPS PharmSciTech. Sep. 2012;13(3):853-62.doi:10.1208/s12249-012-9803-6. Epub May 31, 2012.

(Continued)

Primary Examiner — Sudhakar Katakam
(74) Attorney, Agent, or Firm — Wolf, Greenfield & Sacks, P.C.

(57) ABSTRACT

Described herein are vitamin C prodrugs of Formula (I), (II), or (III), and pharmaceutically acceptable salts thereof. Also provided are pharmaceutical compositions, cosmetic or personal care composition, neutraceutical composition, and medical food composition thereof. Methods of using the compounds or compositions thereof for treating diseases are also provided.

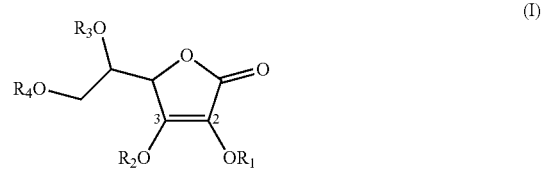

(I)

25 Claims, No Drawings

(56) References Cited

OTHER PUBLICATIONS

Majumdar et al.., The effect of water solubility of solutes on their flux through human skin in vitro. Int J Pharm. Feb. 1, 2007;329(1-2):25-36. Epub Aug. 22, 2006.
McGowan et al., Prodrugs of vitamin C: the reaction of t-acyloxyalkyl-1-iodides with vitamin C 5,6-acetonide. Tetra. Letters. 2015;56:5441-5444.
Olabisi et al.., Rational approach to selective and direct 2-O-alkylation of 5,6-O-isopropylidine-L-ascorbic acid. J Org Chem. Oct. 15, 2004;69(21):7026-32.
Pinnell et al.., Topical L-ascorbic acid: percutaneous absorption studies. Dermatol Surg. Feb. 2001;27(2):137-42.
Potts et al.., Predicting skin permeability. Pharm Res. May 1992;9(5):663-9.
Prybylski et al., Regioselective synthesis of 2-0-acyl-3-0-{t-acyloxyalkyl) prodrugs of 5,6-isopropylidene-t-ascorbic acid. Tetra. Letters. 2016;57:1619-1621.
Roberts et al.., Application of the transformed Potts—Guy equation to in vivo human skin data. Int. J. Pharm. 2001; 90:1318-1323.
Roberts et al.., Correlation of aqueous and lipid solubilities with flux for prodrugs of 5-fluorouracil, theophylline, and 6-mercaptopurine: A Potts-Guy approach. J Pharm Sci. May 1999;88(5):515-22.
Roberts et al.., Prediction of Transdermal Flux of Prodrugs of 5-Fluorouracil, Theophylline, and 6-Mercaptopurine with a Series/Parallel Model. J. Pharm. Sci. 2000;89:1415-1431.
Sinisterra et al., Encapsulation and release of rhodium(II) citrate and its association complex with hydroxypropyl-β-cyclodextrin from biodegradable polymer microspheres. J. Pharm. Sci., 1999;88:574-576.
Sloan et al., Prodrugs of 6-thiopurines: Enhanced delivery through the skin. J. Pharm. Sci. 1983;72:372-378.
Sloan et al., A surrogate for topical delivery in human skin: silicone membranes. Ther Deliv. Feb. 2013;4(2):203-24. doi: 10.4155/tde.12.131.
Sloan et al., Dermal and transdermal delivery:prodrugs. Ther Deliv. Jan. 2011;2(1):83-105.
Sloan et al., Design for optimized topical delivery: Prodrugs and a paradigm change. Pharm Res. Dec. 2006;23(12):2729-47. Epub Nov. 16, 2006.
Sloan, Mannich base derivatives of theophylline and 5-fluorouracil: Syntheses, properties and topical delivery characteristics. Int. J. Pharma. Sep. 1984;21(3):251-264.
Sloan, Prodrugs for dermal delivery. Adv. Drug Del. Rev., 1989;3:67-101.
Thomas et al.., Overcoming steric effects in the coupling reaction of alkyloxycarbonyloxymethyl (AOCOM) halides with phenols: an efficient synthesis of AOCOM phenolic prodrugs. Tetrahedron Lett. 2007;48:109-112.
Thomas et al.., Reaction of alkylcarbonyloxymethyl halides with phenols: reevaluating the influence of steric hindrance. Tetrahedron Lett. 2006;47:8785-8787.
Thomas et al.., Reaction of α-(n-Alkylcarbonyloxy)alkyl (ACOA) Halides with 4-Hydroxy-acetanilide and 2,2,5,7,8-Pentamethyl-6-chromanol: The Effect of Steric Hindrance on Reaction Path. Synthesis. 2008;2:272-278.
Wheeler et al., Orally active esters of cephalosporin antibiotics. 3. Synthesis and biological properties of aminoacyloxymethyl esters of 7-[D(−)-mandelamido]-3-[[(1-methyl-1H-tetrazol-5-yl)thio]methyl]-3-cephem-4-carbo xylic acid. J Med Chem. Jun. 1979;22(6):657-61.
Wu et al.. Mild, Efficient and Highly Selective Hydrolysis of Acetonides with Antimony Trichloride. Letters in Organic Chemistry 2006;3:271-274. Supporting Information.
Beifuss et al., Regioselective Synthesis of 3-0-Alkyl Ethers of Ascorbic Acid without Protecting Groups in a Single Step. Tetrahedron. 2000;56:357-361.
Getz et al., Mechanism of Hydrolysis of 0-Imidomethyl Derivatives of Phenols. J Org Chem. 1993;58:4913-4918.
Jansen et al., Some Novel Penicillin Derivatives. J Chem Soc. 1965;379:2127-2132.
Kato et al., Studies on scavengers of active oxygen species. 1. Synthesis and biological activity of 2-O-alkylascorbic acids. J Med Chem. Apr. 1988;31(4):793-8.
Leppänen et al., Synthesis and in-vitro/in-vivo evaluation of orally administered entacapone prodrugs. J Pharm Pharmacol. Nov. 2001;53(11):1489-98.
Nomura et al., Hiroaki Nomura and Keiichi Sugimoto: Synthesis of L-Ascorbic Acid Acy! Derivatives stabilized against Oxidation. Chem Pharm Bull. 1966;14(9):1039-1044.
Sloan et al., Functional Group Considerations in the Development of Prodrug Approaches to Solving Topical Delivery Problems. Prodrugs in Solving Topical Delivery Problems. Ed:Marcel Dekker, Inc. 1992. 21-26.
Sloan et al., Reaction of (acyloxy)alkyl .alpha.-halides with phenols: effect of nucleofugicity and nucleophilicity on product distribution. J. Org. Chem. 1983;48(21):3777-3783.

* cited by examiner

VITAMIN C PRODRUGS AND USES THEREOF

RELATED APPLICATIONS

This application is a national stage filing under 35 U.S.C. §371 of international PCT application, PCT/US2014/057198, filed Sep. 24, 2014, which claims priority under 35 U.S.C. §119(e) to U.S. provisional patent application, U.S. Ser. No. 61/882,503, filed Sep. 25, 2013, each of which is incorporated herein by reference.

FIELD OF THE INVENTION

This invention relates to prodrugs of vitamin C and uses thereof.

BACKGROUND OF THE INVENTION

Vitamin C is a six carbon compound structurally related to glucose. The term "vitamin C" is commonly used to refer to two compounds: L-ascorbic acid, which is a strong reducing agent, and its oxidised form, L-dehydroascorbic acid:

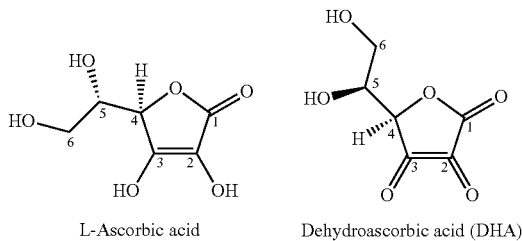

L-Ascorbic acid     Dehydroascorbic acid (DHA)

Both forms have biological activity and are interconvertible by an oxidation/reduction reaction (Basu, T. K. and Dickerson, J. W. T. (1996) In: Vitamins in Human Health and Disease, Cab International, Oxford, UK, pp125-147).

Vitamin C is important in the synthesis of collagen, neurotransmitters and carnitine, in the absorption of non-heme iron, and as an enzyme cofactor. Vitamin C plays a major role as an antioxidant and free-radical scavenger and is involved in the detoxification of many foreign compounds. It is also essential in the metabolism of folic acid (Basu, T. K. and Dickerson, J. W. T. (1996) In: Vitamins in Human Health and Disease, Cab International, Oxford, UK, pp125-147).

Vitamin C is not produced in the human body. Humans rely on dietary intake of vitamin C for their needs. Vitamin C is by far the most consumed dietary supplement. It acts as an antioxidant; prevents colds and boosts immunity; promotes wound healing; protects against effects of stress; and even prevents or assists in the treatment of cancer. (G. Block, American Journal of Clinical Nutrition, 1991, 54(6 Suppl):1310S).

However, vitamin C can be unstable in the presence of UV radiation and oxygen. The functional group in vitamin C that is responsible for the instability is the same functional group that is responsible for its beneificial effect, i.e., keto-2,3-enediol moiety. Therefore, there is a need for prodrugs of vitamin C to stabilize the keto-2,3-enediol functional group and to revert to the 2,3-enediol when the anti-oxidant activity of vitamin C is desired.

SUMMARY OF THE INVENTION

Vitamin C is an important anti-oxidant in the body that is essential to many important biological functions. Vitamin C is unstable in the presence of UV radiation and oxygen, and this instability limits its bioavailability, particularly when it is administered topically. The keto-2,3-enediol functional group of vitamin C is responsible for both its beneficial effect and instability.

There are a number of derivatives of vitamin C that are used commercially, but they all have drawbacks to their use for topical delivery of vitamin C. First, various 6- acyl or 5,6-alkylidene derivatives are essentially subject to the same instability issues as vitamin C because the 2,3-enediol functional group has not been masked. Further they do not readily revert to vitamin C. Second, various 2- or 3-alkyl derivatives have been made but they do not express the same biological/pharmacological activity profile as vitamin C and they do not revert to vitamin C. They are not prodrugs; they are "hard (to metabolize)" alkyl derivatives (J. Pharm. Sci., 72 [1983] 372). The 2,3-dialkyl derivatives are devoid of any anti-oxidant properties. Third, various polar 2-phosphate and 2-glucopyranosyl derivatives have been made in combination with 6-acyl derivatives. These derivatives are effective at delivering vitamin C or 6-acyl vitamin C orally but are not as effective as vitamin C topically because they are too polar to permeate the lipid matrix of the stratum corneum (the above comparison assumes that the formulation containing the vitamin C is used immediately after its preparation). Fourth, various 2,3,5,6-tetracyl derivatives has been made. The acyl derivatives of the 2,3-enediol functional group do function as prodrugs by reverting to the 2,3-enediol functional group but the tetracyl derivatives are too lipid soluble to effectively deliver vitamin C topically. A balance of lipid and aqueous solubility is required for topical delivery. (Adv. Drug Del. Rev., 3 [1989] 67). In addition, the acyl derivative of the 3-eneol is essentially an acid anhydride so it suffers from the same potential to cause irritation of the skin as topical administration of acetic anhydride.

The present invention provides prodrugs of vitamin C by masking the 2,3-diol functional group with "soft" (easy to metabolize) alkyl derivatives of the 2,3-enediol (2,3-diSA) and mixed soft alkyl/acyl derivatives of the 2,3-enediol (2-Ac-3-SA) of vitamin C or vitamin C acetonide (or other 6- or 5,6-protected derivatives). The "soft" alkyl group of the 2,3-diol is hydrolyzed in vivo to provide the biologically active 2,3-diol (J. Pharm. Sci., 1983, 72, 372-378). In certain embodiments, the inventive vitamin C prodrugs have the benefit of balanced lipid and aqueous solubilities and provide for effective delivery of vitamin C, for example, effective topical delivery of vitamin C (Pharm. Res., 2006, 23(12), 2729-2747).

In particular, the present invention provides compounds of Formulae (I)-(III) and compositions thereof (e.g., pharmaceutical compositions, cosmetic compositions, nutraceutical compositions, medical foods). The present invention also provides methods of using the inventive compounds and compositions for treating vitamin C deficiency. The invention also provides methods of treating and preventing conditions and diseases using the inventive vitamin C prodrugs, in particular, dermatological conditions and diseases.

In one aspect, the present invention provides compounds of Formula (I):

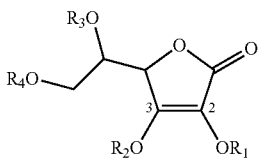

or pharmaceutically acceptable salts thereof, wherein $R_1$, $R_2$, and $R_3$ are as defined herein. In certain embodiments, the present invention provides compounds of Formula (II):

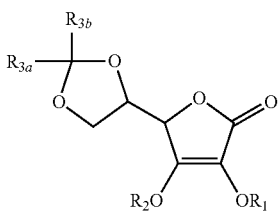

or pharmaceutically acceptable salts thereof, wherein $R_1$, $R_2$, $R_{3a}$, and $R_{3b}$ are as defined herein. In certain embodiments, the present invention provides compounds of Formula (III):

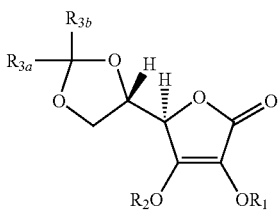

or pharmaceutically acceptable salts thereof, wherein $R_1$, $R_2$, $R_{3a}$, and $R_{3b}$ are as defined herein.

In another aspect, the present invention provides methods of preparing a compound of Formula (I), (II), or (III) or a pharmaceutically acceptable salt by either soft alkylation with a soft alkylating agent at C2—OH and C3—OH, soft alkylation at C2—OH and acylation at C3—OH, or soft alkylation at C3—OH and acylation at C2—OH. This regiospecificity is made possible by the different acidic pKa values of the C2—OH and C3—OH.

In another aspect, the present invention provides pharmaceutical compositions comprising a compound of Formula (I), (II), or (III), or a pharmaceutically acceptable salt thereof, and optionally a pharmaceutically acceptable carrier. In certain embodiments, the pharmaceutical compositions described herein include a therapeutically effective amount of a compound of Formula (I), (II), or (III), or a pharmaceutically acceptable salt thereof.

The present invention also provides cosmetic or personal care compositions comprising a compound of Formula (I), (II), or (III), or a cosmetically acceptable salt thereof, and optionally a cosmetically acceptable carrier.

In another aspect, the present invention provides nutraceutical compositions comprising a compound of Formula (I), (II), or (III), or a nutraceutically acceptable salt thereof, and optionally a neutraceutically acceptable carrier. The nutraceutical composition may include other vitamins and minerals.

In another aspect, the present invention provides a medical food comprising a compound of Formula (I), (II), or (III), or a nutritionally acceptable salt, and optionally a nutritionally acceptable carrier. For example, the compounds of Formula (I), (II), or (III), or an acceptable salt thereof, may be used to fortify a food.

In another aspect, the present invention provides methods of delivering vitamin C to a subject by administering an effective amount of a compound of Formula (I), (II), or (III). The invention also provides methods of treating and/or preventing vitamin C deficiency comprising administering an effective amount of a compound of Formula (I), (II), or (III) to a subject in need thereof. The invention further provides methods of treating or preventing a disease or condition comprising administering an effective amount of a compound of Formula (I), (II), or (III) to a subject in need thereof. In certain embodiments, the invention provides methods of treating or preventing a dermatological disease or condition comprising administering an effective amount of a compound of Formula (I), (II), or (III) to a subject in need thereof.

In another aspect, the present invention provides kits comprising a compound of Formulae (I), (II), or (III), pharmaceutical compositions thereof, cosmetic or personal care compositions thereof, nutraceutical compositions thereof, or medical foods thereof. The kits of the invention may include a single dose or multiple doses of a compound of Formula (I), (II), or (III), or a pharmaceutically acceptable salt, or composition thereof. The provided kits may be useful for the treatment and/or prevention of vitamin C deficiency, diseases, and/or conditions. In certain embodiments, the kits described herein further include instructions for administering the compound of Formula (I), (II), or (III), or the pharmaceutically acceptable salt thereof, or compositions thereof. The kits may also include packaging information describing the use of the compound or composition, or prescribing information for the subject or a health care professional. Such information may be required by a regulatory agency such as the U.S. Food and Drug Administration (FDA). The kit may also optionally include a device for administration of the compound or composition, for example, a dropper for ocular administration or a syringe for parenteral administration.

The details of certain embodiments of the invention are set forth herein. Other features, objects, and advantages of the invention will be apparent from the Detailed Description, Examples, and Claims.

DEFINITIONS

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentyl ($C_5$), amyl ($C_5$), neopentyl ($C_5$), 3-methyl-2-butyl ($C_5$), tertiary amyl ($C_5$), and n-hexyl ($C_6$). Additional examples of alkyl groups include n-heptyl ($C_7$), n-octyl ($C_8$), and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl (e.g., —$CH_3$). In certain embodiments, the alkyl group is substituted $C_{1-10}$ alkyl.

"Alkenyl" refers to a radical of a straight-chain or branched hydrocarbon group having from 3 to 20 carbon atoms, one or more carbon-carbon double bonds, and no triple bonds ("$C_{3-20}$ alkenyl"). In some embodiments, an alkenyl group has 3 to 10 carbon atoms ("$C_{3-10}$ alkenyl"). In some embodiments, an alkenyl group has 3 to 9 carbon atoms ("$C_{3-9}$ alkenyl"). In some embodiments, an alkenyl group has 3 to 8 carbon atoms ("$C_{3-8}$ alkenyl"). In some embodiments, an alkenyl group has 3 to 7 carbon atoms ("$C_{3-7}$ alkenyl"). In some embodiments, an alkenyl group has 3 to 6 carbon atoms ("$C_{3-6}$ alkenyl"). In some embodiments, an alkenyl group has 3 to 5 carbon atoms ("$C_{3-5}$ alkenyl"). In some embodiments, an alkenyl group has 3 to 4 carbon atoms ("$C_{3-4}$ alkenyl"). In some embodiments, an alkenyl group has 3 carbon atoms ("$C_3$ alkenyl"). Examples of $C_{3-4}$ alkenyl groups include 2-propenyl ($C_3$), 2-butenyl ($C_4$), and the like. Examples of $C_{3-6}$ alkenyl groups include the aforementioned $C_{3-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{3-10}$ alkenyl. In certain embodiments, the alkenyl group is substituted $C_{3-10}$ alkenyl.

"Alkynyl" refers to a radical of a straight-chain or branched hydrocarbon group having from 3 to 20 carbon atoms, one or more carbon-carbon triple bonds, and optionally one or more double bonds ("$C_{3-20}$ alkynyl"). In some embodiments, an alkynyl group has 3 to 10 carbon atoms ("$C_{3-10}$ alkynyl"). In some embodiments, an alkynyl group has 3 to 9 carbon atoms ("$C_{3-9}$ alkynyl"). In some embodiments, an alkynyl group has 3 to 8 carbon atoms ("$C_{3-8}$ alkynyl"). In some embodiments, an alkynyl group has 3 to 7 carbon atoms ("$C_{3-7}$ alkynyl"). In some embodiments, an alkynyl group has 3 to 6 carbon atoms ("$C_{3-6}$ alkynyl"). In some embodiments, an alkynyl group has 3 to 5 carbon atoms ("$C_{3-5}$ alkynyl"). In some embodiments, an alkynyl group has 3 to 4 carbon atoms ("$C_{3-4}$ alkynyl"). In some embodiments, an alkynyl group has 3 carbon atoms ("$C_3$ alkynyl"). Examples of $C_{3-4}$ alkynyl groups include, without limitation, 2-propynyl ($C_3$), 2-butynyl ($C_4$), and the like. Examples of $C_{3-6}$ alkenyl groups include the aforementioned $C_{3-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contains a fused, bridged, or spiro ring system such as a bicyclic system ("bicyclic carbocyclyl") and can be saturated or partially unsaturated. "Carbocyclyl" also includes ring systems wherein the carbocyclic ring, as defined above, is fused to one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl. In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In certain embodiments, the heteroatom is independently selected from nitrogen, sulfur, and oxygen. In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl. In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiorenyl. Exemplary 4-membered heterocyclyl groups containing one heteroatom include, without limitation, azetidinyl, oxetanyl, and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl, and thiepanyl. Exemplary 8-membered heterocyclyl groups containing one heteroatom include, without limitation, azocanyl, oxecanyl, and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Arylalkyl" is a subset of alkyl and aryl, as defined herein, and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen, and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl, as defined herein, and refers to an optionally substituted alkyl group substituted by an optionally substituted heteroaryl group.

"Partially unsaturated" refers to a group that includes at least one double or triple bond. A "partially unsaturated" ring system is further intended to encompass rings having multiple sites of unsaturation but is not intended to include aromatic groups (e.g., aryl or heteroaryl groups) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, as defined herein, which are divalent bridging groups are further referred to using the suffix -ene, e.g., alkylene, alkenylene, alkynylene, carbocyclylene, heterocyclylene, arylene, and heteroarylene.

As used herein, the term "optionally substituted" refers to a substituted or unsubstituted moiety.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$—C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{3-10}$ alkenyl, C$_{3-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$=NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{3-10}$ alkenyl, C$_{3-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO2R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{3-10}$ alkenyl, C$_{3-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{3-10}$ alkenyl, C$_{3-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{3-6}$ alkenyl, C$_{3-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{3-6}$ alkenyl, C$_{3-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{3-6}$ alkenyl, C$_{3-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —C$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$—C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{3-6}$ alkenyl, C$_{3-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

"Halo" or "halogen" refers to fluorine (fluoro, —F), chlorine (chloro, —Cl), bromine (bromo, —Br), or iodine (iodo, —I).

"Acyl" as used herein refers to a moiety selected from the group consisting of —C(=O)R$^{aa}$, —CHO, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —C(=O)NR$^{bb}$SO$_2$R$^{aa}$, —C(=S)N(R$^{bb}$)$_2$, —C(=O)SR$^{aa}$, and —C(=S)SR$^{aa}$, wherein R$^{aa}$ and R$^{bb}$ are as defined herein.

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{3-10}$ alkenyl, C$_{3-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Oxygen protecting groups are well known in the art and include those described in *Protecting Groups in Organic Synthesis*, T. W. Greene and P. G. M. Wuts, $3^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, t-butyl carbonate (BOC), alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, tosylate (Ts), and alkylcarbonyloxymethyl (ACOM) protecting groups such as pivaloyloxy methyl $(CH_3)_3CC(=O)OCH_2$.

In certain embodiments, the substituent present on a sulfur atom is a sulfur protecting group (also referred to as a thiol protecting group). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in *Protecting Groups in Organic Synthesis*, T. W. Greene and P. G. M. Wuts, 3$^{rd}$ edition, John Wiley & Sons, 1999, incorporated herein by reference.

These and other exemplary substituents are described in more detail in the Detailed Description, Examples, and Claims. The invention is not intended to be limited in any manner by the above exemplary listing of substituents.

Other Definitions

The following definitions are more general terms used throughout the present application.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, and sulfuric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4} \text{ alkyl})_4^-$ salts. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, lower-alkyl sulfonate, and aryl sulfonate.

The term "nutraceutical composition" refers to a class of compositions used as nutritional supplements, or otherwise as materials that are ingested for their healthful benefits, and are generally free from manufactured pharmaceuticals. In addition to the inventive compounds as described herein, the neutraceutical compositions provided herein may include, but are not limited to, one or more of the following: vitamins (e.g., ascorbic acid, pyridoxine, riboflavin), minerals (e.g., calcium salts, zinc salts, potassium salts), hormones (e.g. dehydroepiandrosterone (DHEA), melatonin), biochemicals (e.g., adenosine triphosphate, coenzyme A, cysteine, dimethylaminoethanol (DMAE), glandulars (e.g., edible compositions derived from glandular organs of animals such as the thyroid, pancreas, adrenal cortex), or herbals (e.g., ginkgo, garlic, goldenseal, echinacea).

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds of Formulae (I)-(III) may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound which is associated with water. Typically, the number of the water molecules contained in a hydrate of a compound is in a definite ratio to the number of compound molecules in the hydrate. Therefore, a hydrate of a compound may be represented, for example, by the general formula $R.x\ H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates ($R.0.5\ H_2O$)), and polyhydrates (x is a number greater than 1, e.g., dihydrates ($R.2\ H_2O$) and hexahydrates ($R.6\ H_2O$)).

As used herein, the term "tautomer" includes two or more interconvertible forms resulting from at least one formal migration of a hydrogen atom and at least one change in valency (e.g., a single bond to a double bond, a triple bond to a double bond, or vice versa). The exact ratio of the tautomers depends on several factors, including temperature, solvent, and pH. Tautomerizations (i.e., the reaction providing a tautomeric pair) may be catalyzed by acid or base. Exemplary tautomerizations include keto-to-enol; amide-to-imide; lactam-to-lactim; enamine-to-imine; and enamine-to-(a different) enamine tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and/or solubility. Recrystallization solvent, rate of crystallization, storage temperature, and other factors may cause one crystal form to dominate. Various polymorphs of a compound can be prepared by crystallization under different conditions.

The term "prodrugs" refer to compounds, including derivatives of the compounds of Formulae (I)-(III), which have cleavable groups and are converted by hydrolysis or under physiological conditions to the compounds of Formulae (I)-(III), which are pharmaceutically active in vivo. (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, from acidic groups pendant on the compounds of this invention are particular prodrugs. In some cases it is desirable to prepare double ester type prodrugs such as (acyloxy)alkyl esters or ((alkoxycarbonyl)oxy)alkyl esters. $C_1$ to $C_8$ alkyl, $C_3$-$C_8$ alkenyl, $C_3$-$C_8$ alkynyl, aryl, $C_7$-$C_{12}$ substituted aryl, and $C_7$-$C_{12}$ arylalkyl esters of the compounds of Formula (I)-(III) may be preferred in certain instances.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A non-human animal may be a transgenic animal.

The terms "administer," "administering," or "administration," as used herein refers to implanting, absorbing, ingesting, injecting, inhaling, or otherwise introducing an inventive compound, or a pharmaceutical composition thereof.

As used herein, the terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

As used herein, the terms "condition," "disease," and "disorder" are used interchangeably.

An "effective amount" of a compound refers to an amount sufficient to elicit a desired biological response, i.e., treating the condition. As will be appreciated by those of ordinary skill in this art, the effective amount of a compound provided in the invention may vary depending on such factors as the desired biological endpoint, the pharmacokinetics of the compound, the condition being treated, the mode of administration, and the age and health of the subject. An effective amount encompasses therapeutic and prophylactic treatment. For example, in treating cancer, an effective amount of an inventive compound may reduce the tumor burden or stop the growth or spread of a tumor. In treating macular degeneration, an effective amount of an inventive compound may improve sight, reduce the risk of vision loss, or prevent central vision loss from worsening.

A "therapeutically effective amount" of a compound provided in the invention is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound of Formula (I), (II), or (III) is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

As used herein, "skin aging" includes skin atrophy and means the thinning and/or general degradation of the dermis caused by free radical damage which is often characterized by an alteration and degeneration of collagen and/or elastin. In epidermis, markers of degeneration include lipofuscin granules and loss of rete pegs. Skin aging may be caused by either intrinsic or extrinsic factors such as natural chrono-aging, photodamage, burns, or chemical damage.

As used herein, "regulating skin aging" means preventing, retarding, arresting, treating, or reversing the process of skin aging in mammalian skin.

As used herein, "cosmetic" means articles intended to be applied to the human body or any part thereof for cleansing, beautifying, promoting attractiveness or altering the appearance thereof.

As used herein, "hard alkyl" refers to the type of alkyl group masking the 2,3-diol of the vitamin C wherein the alkyl group is hard to hydrolize in vivo to provide the biological active 2,3-diol.

As used herein, "soft alkyl" refers to the type of alkyl group masking the 2,3-diol of the vitamin C wherein the alkyl group is easy to hydrolize in vivo to provide the biological active 2,3-diol.

As used herein, "soft alkylating agent" refers to a compound capable of alkylating the 2,3-diol of the vitamin C wherein the alkyl group is easy to hydrolize in vivo to provide the biological active 2,3-diol.

DETAILED DESCRIPTION OF CERTAIN EMBODIMENTS OF THE INVENTION

Vitamin C is an important anti-oxidant in the body, and its instability is due to the keto-2,3-enediol functional group that is also responsible for the beneficial effect of vitamin C. The present invention provides prodrugs of vitamin C by masking the 2,3-enediol functional group with a "soft" alkyl group and an acyl group or two "soft" alkyl groups. The "soft" alkyl and acyl groups can be hydrolyzed to provide the beneficial 2,3-enediol in vivo. For example, for a provided compound with the substituent C3—O—CH$_2$—O—(C=O)—CH$_3$, the C=O in the α-acylheteroalkyl functions as a target for chemical or enzymatic hydrolysis to give C3—O—CH$_2$—OH, which spontaneously decomposes to give a free hydroxyl group at C3. The invention provides vitamin C prodrugs with the benefit of balanced lipid and aqueous solubilities and effective delivery of vitamin C, for example, effective topical delivery of vitamin C.

The present invention provides compounds of Formulae (I)-(III) and compositions thereof. Also provided are methods of using compounds of Formulae (I)-(III) and compositions to deliver vitamin C, treat and/or prevent vitamin C deficiency, or treat and/or prevent a disease or condition (e.g., a dermatological disease or condition).

Compounds

As generally described herein, the present disclosure provides compounds of Formula (I):

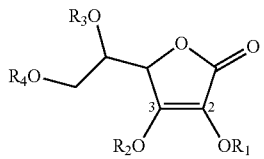
(I)

or a pharmaceutically or cosmetically acceptable salt thereof,
wherein:
R$_1$ is hydrogen or of Formula (A), Formula (B), or Formula (E):

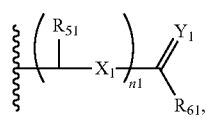
(A)

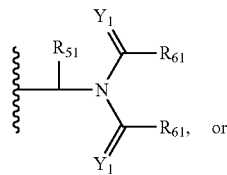
(B)

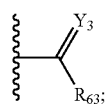
(E)

R$_2$ is of Formula (C), Formula (D), or Formula (E):

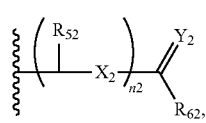
(C)

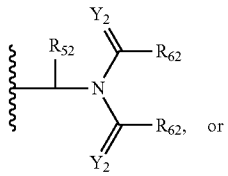
(D)

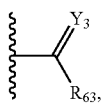
(E)

provided that R$_1$ and R$_2$ are not both of Formula (E);
R$_3$ and R$_4$ are each independently hydrogen, or of Formula (E):

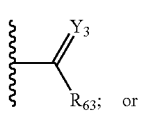
(E)

R$_3$ and R$_4$ are taken together with the intervening atoms to form an optionally substituted heterocyclic ring;
each of X$_1$ and X$_2$ is independently —O—, or —NR$^{XN}$—;
each instance of Y$_1$, Y$_2$, and Y$_3$ is independently O or NR$^{YN}$;
each instance of R$_{51}$ and R$_{52}$ is independently hydrogen, optionally substituted C$_{1-6}$ alkyl, optionally substituted C$_{3-6}$ alkenyl, optionally substituted C$_{3-6}$ alkynyl, optionally substituted C$_{3-6}$ carbocyclyl, optionally substituted 3- to 6-membered heterocyclyl, optionally substituted aryl, optionally substituted heteroaryl;
each instance of R$_{61}$, R$_{62}$, and R$_{63}$ is independently optionally substituted C$_{1-6}$ alkyl, optionally substituted C$_{3-6}$ alkenyl, optionally substituted C$_{3-6}$ alkynyl, optionally substituted C$_{3-6}$ carbocyclyl, optionally substituted 3- to 6-membered heterocyclyl, optionally substituted aryl, optionally substituted heteroaryl, —OR$^{56O}$, —N(R$^{56N}$)$_2$, or two R$_{61}$ are taken together with their intervening atoms to form an optionally substituted heterocyclic ring, or two R$_{62}$ are taken together with their intervening atoms to form an optionally substituted heterocyclic ring; or
R$_{51}$ and R$_{61}$ are taken together with the intervening atoms to form an optionally substituted heterocyclic ring; or
R$_{52}$ and R$_{62}$ are taken together with the intervening atoms to form an optionally substituted heterocyclic ring;
each instance of R$^{XN}$, R$^{YN}$, and R$^{56N}$ is independently hydrogen, optionally substituted C$_{1-6}$ alkyl, optionally substituted C$_{3-6}$ alkenyl, optionally substituted C$_{3-6}$ alkynyl, optionally substituted C$_{3-6}$ carbocyclyl, optionally substituted aryl, optionally substituted 3- to 6-membered heterocyclyl, optionally substituted heteroaryl, or a nitrogen protecting group;
each instance of R$^{56O}$ is independently optionally substituted C$_{1-6}$ alkyl, optionally substituted C$_{3-6}$ alkenyl, optionally substituted C$_{3-6}$ alkynyl, optionally substituted C$_{3-6}$ carbocyclyl, optionally substituted 3- to 6-membered heterocyclyl, optionally substituted aryl, optionally substituted heteroaryl, or an oxygen protecting group;
n$_1$ is 1, 2, or 3; and
n$_2$ is 1, 2, or 3.

As generally described above, $R_1$ is hydrogen or of Formula (A), Formula (B), or Formula (E). In certain embodiments, $R_1$ is hydrogen. In certain embodiments, $R_1$ is of Formula (A):

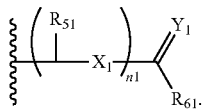

In certain embodiments, $R_1$ is of Formula (B):

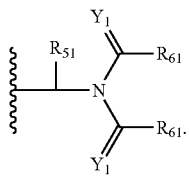

In certain embodiments, $R_1$ is of Formula (E):

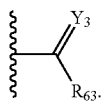

As generally described above, $R_2$ is of Formula (C), Formula (D), or Formula (E), provided that $R_1$ and $R_2$ are not both of Formula (E). In certain embodiments, $R_2$ is of Formula (C):

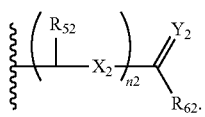

In certain embodiments, $R_2$ is of Formula (D):

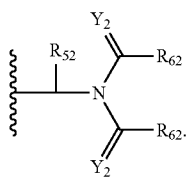

In certain embodiments, $R_2$ is of Formula (E):

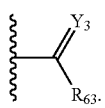

In certain embodiments, $R_1$ is hydrogen, and $R_2$ is of Formula (C) or Formula (D). In certain embodiments, $R_1$ is hydrogen, and $R_2$ is of Formula (C). In certain embodiments, $R_1$ is hydrogen, and $R_2$ is of Formula (D). In certain embodiments, $R_1$ is of Formula (A), and $R_2$ is of Formula (C), Formula (D), or Formula (E). In certain embodiments, $R_1$ is of Formula (A), and $R_2$ is of Formula (C). In certain embodiments, $R_1$ is of Formula (A), and $R_2$ is of Formula (D). In certain embodiments, $R_1$ is of Formula (A), and $R_2$ is of Formula (E). In certain embodiments, $R_1$ is of Formula (B), and $R_2$ is of Formula (C), Formula (D), or Formula (E). In certain embodiments, $R_1$ is of Formula (B), and $R_2$ is of Formula (C). In certain embodiments, $R_1$ is of Formula (B), and $R_2$ is of Formula (D). In certain embodiments, $R_1$ is of Formula (B), and $R_2$ is of Formula (E). In certain embodiments, $R_1$ is of Formula (E), and $R_2$ is of Formula (C) or Formula (D). In certain embodiments, $R_1$ is of Formula (E), and $R_2$ is of Formula (C). In certain embodiments, $R_1$ is of Formula (E) and $R_2$ is of Formula (D).

As generally described above, $R_3$ is hydrogen or of Formula (E):

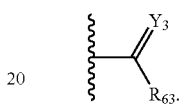

In certain embodiments, $R_3$ is hydrogen. In certain embodiments, $R_3$ is of Formula (E).

As generally described above, $R_4$ is hydrogen or of Formula (E):

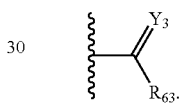

In certain embodiments, $R_4$ is hydrogen. In certain embodiments, $R_4$ is of Formula (E).

In certain embodiments, $R_3$ and $R_4$ are taken together with the intervening atoms to form an optionally substituted heterocyclic ring. In some embodiments, $R_3$ and $R_4$ are taken together with the intervening atoms to form an optionally substituted 5-membered heterocyclic ring. In some embodiments, $R_3$ and $R_4$ are taken together with the intervening atoms to form an optionally substituted 5-membered heterocyclic ring of the formula:

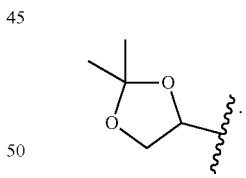

In some embodiments, $R_3$ and $R_4$ are taken together with the intervening atoms to form an optionally substituted 5-membered heterocyclic ring of the formula:

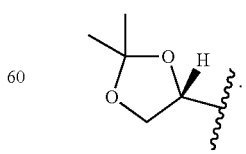

As generally described above, $X_1$ is —O— or —NR$^{XN}$—. In certain embodiments, $X_1$ is —O—. In certain embodiments, $X_1$ is —NR$^{XN}$—, wherein R$^{XN}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, or a nitrogen protecting group. In certain embodiments, $X_1$ is —NH—. In certain embodiments, $X_1$ is —NR$^{XN}$—, wherein R$^{XN}$ is independently optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, or a nitrogen protecting group. In certain embodiments, $X_1$ is —NR$^{XN}$—, wherein R$^{XN}$ is independently optionally substituted $C_{1-6}$ alkyl. In certain embodiments, $X_1$ is —N(CH$_3$)—, —N(C$_2$H$_5$)—, or —N(C$_3$H$_7$)—. In certain embodiments, $X_1$ is —NR$^{XN}$—, wherein R$^{XN}$ is independently optionally substituted $C_{3-6}$ alkenyl. In certain embodiments, $X_1$ is —NR$^{XN}$—, wherein R$^{XN}$ is independently optionally substituted $C_{3-6}$ alkynyl. In certain embodiments, $X_1$ is —NR$^{XN}$—, wherein R$^{XN}$ is independently optionally substituted $C_{3-6}$ carbocyclyl. In certain embodiments, $X_1$ is —NR$^{XN}$—, wherein R$^{XN}$ is independently optionally substituted aryl. In certain embodiments, $X_1$ is —NR$^{XN}$—, wherein R$^{XN}$ is independently optionally substituted phenyl. In certain embodiments, $X_1$ is —NR$^{XN}$—, wherein R$^{XN}$ is phenyl. In certain embodiments, $X_1$ is —NR$^{XN}$—, wherein R$^{XN}$ is independently optionally substituted 3- to 6-membered heterocyclyl. In certain embodiments, $X_1$ is —NR$^{XN}$—, wherein R$^{XN}$ is independently optionally substituted 6-membered heterocyclyl. In certain embodiments, $X_1$ is —NR$^{XN}$—, wherein R$^{XN}$ is independently optionally substituted 5-membered heterocyclyl. In certain embodiments, $X_1$ is —NR$^{XN}$—, wherein R$^{XN}$ is independently optionally substituted heteroaryl. In certain embodiments, $X_1$ is —NR$^{XN}$—, wherein R$^{XN}$ is independently optionally substituted 6-membered heteroaryl. In certain embodiments, $X_1$ is —NR$^{XN}$—, wherein R$^{XN}$ is independently optionally substituted 5-membered heteroaryl. In certain embodiments, $X_1$ is —NR$^{XN}$—, wherein R$^{XN}$ is a nitrogen protecting group. In certain embodiments, $X_1$ is —NR$^{XN}$—, wherein R$^{XN}$ is Bn, BOC, Cbz, Fmoc, trifluoroacetyl, triphenylmethyl, or Ts.

As generally described above, $X_2$ is —O— or —NR$^{XN}$—. In certain embodiments, $X_2$ is —O—. In certain embodiments, $X_2$ is —NR$^{XN}$—, wherein R$^{XN}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, or a nitrogen protecting group. In certain embodiments, $X_2$ is —NH—. In certain embodiments, $X_2$ is —NR$^{XN}$—, wherein R$^{XN}$ is independently optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, or a nitrogen protecting group. In certain embodiments, $X_2$ is —NR$^{XN}$—, wherein R$^{XN}$ is independently optionally substituted $C_{1-6}$ alkyl. In certain embodiments, $X_2$ is —N(CH$_3$)—, —N(C$_2$H$_5$)—, or —N(C$_3$H$_7$)—. In certain embodiments, $X_2$ is —NR$^{XN}$—, wherein R$^{XN}$ is independently optionally substituted $C_{3-6}$ alkenyl. In certain embodiments, $X_2$ is —NR$^{XN}$—, wherein R$^{XN}$ is independently optionally substituted $C_{3-6}$ alkynyl. In certain embodiments, $X_2$ is —NR$^{XN}$—, wherein R$^{XN}$ is independently optionally substituted $C_{3-6}$ carbocyclyl. In certain embodiments, $X_2$ is —NR$^{XN}$—, wherein R$^{XN}$ is independently optionally substituted aryl. In certain embodiments, $X_2$ is —NR$^{XN}$—, wherein R$^{XN}$ is independently optionally substituted phenyl. In certain embodiments, $X_2$ is —NR$^{XN}$—, wherein R$^{XN}$ is phenyl. In certain embodiments, $X_2$ is —NR$^{XN}$—, wherein R$^{XN}$ is independently optionally substituted 3- to 6-membered heterocyclyl. In certain embodiments, $X_2$ is —NR$^{XN}$—, wherein R$^{XN}$ is independently optionally substituted 6-membered heterocyclyl. In certain embodiments, $X_2$ is —NR$^{XN}$—, wherein R$^{XN}$ is independently optionally substituted 5-membered heterocyclyl. In certain embodiments, $X_2$ is —NR$^{XN}$—, wherein R$^{XN}$ is independently optionally substituted heteroaryl. In certain embodiments, $X_2$ is —NR$^{XN}$—, wherein R$^{XN}$ is independently optionally substituted 6-membered heteroaryl. In certain embodiments, $X_2$ is —NR$^{XN}$—, wherein R$^{XN}$ is independently optionally substituted 5-membered heteroaryl. In certain embodiments, $X_2$ is —NR$^{XN}$—, wherein R$^{XN}$ is a nitrogen protecting group. In certain embodiments, $X_2$ is —NR$^{XN}$—, wherein R$^{XN}$ is Bn, BOC, Cbz, Fmoc, trifluoroacetyl, triphenylmethyl, or Ts.

In certain embodiments, $X_1$ and $X_2$ are the same. In certain embodiments, $X_1$ and $X_2$ are O. In certain embodiments, $X_1$ and $X_2$ are different.

As generally described above, $Y_1$ is O or NR$^{YN}$. In certain embodiments, $Y_1$ is O. In certain embodiments, $Y_1$ is NR$^{YN}$, wherein R$^{YN}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, or a nitrogen protecting group. In certain embodiments, $Y_1$ is NH. In certain embodiments, $Y_1$ is NR$^{YN}$, wherein R$^{YN}$ is independently optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, or a nitrogen protecting group. In certain embodiments, $Y_1$ is NR$^{YN}$, wherein R$^{YN}$ is independently optionally substituted $C_{1-6}$ alkyl. In certain embodiments, $Y_1$ is N(CH$_3$), N(C$_2$H$_5$), or N(C$_3$H$_7$). In certain embodiments, $Y_1$ is NR$^{YN}$, wherein R$^{YN}$ is independently optionally substituted $C_{3-6}$ alkenyl. In certain embodiments, $Y_1$ is NR$^{YN}$, wherein R$^{YN}$ is independently optionally substituted $C_{3-6}$ alkynyl. In certain embodiments, $Y_1$ is NR$^{YN}$, wherein R$^{YN}$ is independently optionally substituted $C_{3-6}$ carbocyclyl. In certain embodiments, $Y_1$ is NR$^{YN}$, wherein R$^{YN}$ is independently optionally substituted aryl. In certain embodiments, $Y_1$ is NR$^{YN}$, wherein R$^{YN}$ is independently optionally substituted phenyl. In certain embodiments, $Y_1$ is NR$^{YN}$, wherein R$^{YN}$ is phenyl. In certain embodiments, $Y_1$ is —NR$^{YN}$—, wherein R$^{YN}$ is independently optionally substituted 3- to 6-membered heterocyclyl. In certain embodiments, $Y_1$ is NR$^{YN}$, wherein R$^{YN}$ is independently optionally substituted 6-membered heterocyclyl. In certain embodiments, $Y_1$ is NR$^{YN}$, wherein R$^{YN}$ is independently optionally substituted 5-membered heterocyclyl. In certain embodiments, $Y_1$ is NR$^{YN}$, wherein R$^{YN}$ is independently optionally substituted heteroaryl. In certain embodiments, $Y_1$ is NR$^{YN}$, wherein R$^{YN}$ is independently optionally substituted 6-membered heteroaryl. In certain embodiments, $Y_1$ is NR$^{YN}$, wherein R$^{YN}$ is independently optionally substituted 5-membered heteroaryl. In certain embodiments, $Y_1$ is NR$^{YN}$, wherein R$^{YN}$ is a nitrogen protecting group. In certain embodiments, $Y_1$ is $NR^{YN}$, wherein $R^{YN}$ is Bn, BOC, Cbz, Fmoc, trifluoroacetyl, triphenylmethyl, or Ts.

As generally described above, $Y_2$ is O or $NR^{YN}$. In certain embodiments, $Y_2$ is O. In certain embodiments, $Y_2$ is $NR^{YN}$, wherein $R^{YN}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, or a nitrogen protecting group. In certain embodiments, $Y_2$ is NH. In certain embodiments, $Y_2$ is $NR^{YN}$, wherein $R^{YN}$ is independently optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, or a nitrogen protecting group. In certain embodiments, $Y_2$ is $NR^{YN}$, wherein $R^{YN}$ is independently optionally substituted $C_{1-6}$ alkyl. In certain embodiments, $Y_2$ is $N(CH_3)$, $N(C_2H_5)$, or $N(C_3H_7)$. In certain embodiments, $Y_2$ is $NR^{YN}$, wherein $R^{YN}$ is independently optionally substituted $C_{3-6}$ alkenyl. In certain embodiments, $Y_2$ is $NR^{YN}$, wherein $R^{YN}$ is independently optionally substituted $C_{3-6}$ alkynyl. In certain embodiments, $Y_2$ is $NR^{YN}$, wherein $R^{YN}$ is independently optionally substituted $C_{3-6}$ carbocyclyl. In certain embodiments, $Y_2$ is $NR^{YN}$, wherein $R^{YN}$ is independently optionally substituted aryl. In certain embodiments, $Y_2$ is $NR^{YN}$, wherein $R^{YN}$ is independently optionally substituted phenyl. In certain embodiments, $Y_2$ is $NR^{YN}$, wherein $R^{YN}$ is phenyl. In certain embodiments, $Y_2$ is $—NR^{YN}—$, wherein $R^{YN}$ is independently optionally substituted 3- to 6-membered heterocyclyl. In certain embodiments, $Y_2$ is $NR^{YN}$, wherein $R^{YN}$ is independently optionally substituted 6-membered heterocyclyl. In certain embodiments, $Y_2$ is $NR^{YN}$, wherein $R^{YN}$ is independently optionally substituted 5-membered heterocyclyl. In certain embodiments, $Y_2$ is $NR^{YN}$, wherein $R^{YN}$ is independently optionally substituted heteroaryl. In certain embodiments, $Y_2$ is $NR^{YN}$, wherein $R^{YN}$ is independently optionally substituted 6-membered heteroaryl. In certain embodiments, $Y_2$ is $NR^{YN}$, wherein $R^{YN}$ is independently optionally substituted 5-membered heteroaryl. In certain embodiments, $Y_2$ is $NR^{YN}$, wherein $R^{YN}$ is a nitrogen protecting group. In certain embodiments, $Y_2$ is $NR^{YN}$, wherein $R^{YN}$ is Bn, BOC, Cbz, Fmoc, trifluoroacetyl, triphenylmethyl, or Ts.

As generally described above, $Y_3$ is O or $NR^{YN}$. In certain embodiments, $Y_3$ is O. In certain embodiments, $Y_3$ is $NR^{YN}$, wherein $R^{YN}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, or a nitrogen protecting group. In certain embodiments, $Y_3$ is NH. In certain embodiments, $Y_3$ is $NR^{YN}$, wherein $R^{YN}$ is independently optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, or a nitrogen protecting group. In certain embodiments, $Y_3$ is $NR^{YN}$, wherein $R^{YN}$ is independently optionally substituted $C_{1-6}$ alkyl. In certain embodiments, $Y_3$ is $N(CH_3)$, $N(C_2H_5)$, or $N(C_3H_7)$. In certain embodiments, $Y_3$ is $NR^{YN}$, wherein $R^{YN}$ is independently optionally substituted $C_{3-6}$ alkenyl. In certain embodiments, $Y_3$ is $NR^{YN}$, wherein $R^{YN}$ is independently optionally substituted $C_{3-6}$ alkynyl. In certain embodiments, $Y_3$ is $NR^{YN}$, wherein $R^{YN}$ is independently optionally substituted $C_{3-6}$ carbocyclyl. In certain embodiments, $Y_3$ is $NR^{YN}$, wherein $R^{YN}$ is independently optionally substituted aryl. In certain embodiments, $Y_3$ is $NR^{YN}$, wherein $R^{YN}$ is independently optionally substituted phenyl. In certain embodiments, $Y_3$ is $NR^{YN}$, wherein $R^{YN}$ is phenyl. In certain embodiments, $Y_3$ is $—NR^{YN}—$, wherein $R^{YN}$ is independently optionally substituted 3- to 6-membered heterocyclyl. In certain embodiments, $Y_3$ is $NR^{YN}$, wherein $R^{YN}$ is independently optionally substituted 6-membered heterocyclyl. In certain embodiments, $Y_3$ is $NR^{YN}$, wherein $R^{YN}$ is independently optionally substituted 5-membered heterocyclyl. In certain embodiments, $Y_3$ is $NR^{YN}$, wherein $R^{YN}$ is independently optionally substituted heteroaryl. In certain embodiments, $Y_3$ is $NR^{YN}$, wherein $R^{YN}$ is independently optionally substituted 6-membered heteroaryl. In certain embodiments, $Y_3$ is $NR^{YN}$, wherein $R^{YN}$ is independently optionally substituted 5-membered heteroaryl. In certain embodiments, $Y_3$ is $NR^{YN}$, wherein $R^{YN}$ is a nitrogen protecting group. In certain embodiments, $Y_3$ is $NR^{YN}$, wherein $R^{YN}$ is Bn, BOC, Cbz, Fmoc, trifluoroacetyl, triphenylmethyl, or Ts.

As generally described above, each instance of $R_{51}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, or optionally substituted heteroaryl. In certain embodiments, $R_{51}$ is hydrogen. In certain embodiments, $R_{51}$ is optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, or optionally substituted heteroaryl. In certain embodiments, $R_{51}$ is optionally substituted $C_{1-6}$ alkyl. In certain embodiments, $R_{51}$ is methyl, ethyl, or propyl. In certain embodiments, $R_{51}$ is methyl. In some embodiments, $R_{51}$ is optionally substituted $C_{3-6}$ alkenyl. In some embodiments, $R_{51}$ is optionally substituted $C_{3-6}$ alkynyl. In some embodiments, $R_{51}$ is optionally substituted $C_{3-6}$ carbocyclyl. In some embodiments, $R_{51}$ is optionally substituted 3- to 6-membered heterocyclyl. In some embodiments, $R_{51}$ is optionally substituted aryl. In some embodiments, $R_{51}$ is optionally substituted phenyl. In some embodiments, $R_{51}$ is phenyl. In some embodiments, $R_{51}$ is optionally substituted heteroaryl.

As generally described above, each instance of $R_{52}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, or optionally substituted heteroaryl. In certain embodiments, $R_{52}$ is hydrogen. In certain embodiments, $R_{52}$ is optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, or optionally substituted heteroaryl. In certain embodiments, $R_{52}$ is optionally substituted $C_{1-6}$ alkyl. In certain embodiments, $R_{52}$ is methyl, ethyl, or propyl. In certain embodiments, $R_{52}$ is methyl. In some embodiments, $R_{52}$ is optionally substituted $C_{3-6}$ alkenyl. In some embodiments, $R_{52}$ is optionally substituted $C_{3-6}$ alkynyl. In some embodiments, $R_{52}$ is optionally substituted $C_{3-6}$ carbocyclyl. In some embodiments, $R_{52}$ is optionally substituted 3- to 6-membered heterocyclyl. In some embodiments, $R_{52}$ is optionally substituted aryl. In some embodiments, $R_{52}$ is optionally substituted phenyl. In some embodiments, $R_{52}$ is phenyl. In some embodiments, $R_{52}$ is optionally substituted heteroaryl.

In certain embodiments, $R_{51}$ and $R_{52}$ are the same. In certain embodiments, $R_{51}$ and $R_{52}$ are both hydrogen. In certain embodiments, $R_{51}$ and $R_{52}$ are both methyl. In certain embodiments, $R_{51}$ and $R_{52}$ are different. In certain embodiments, $R_{51}$ is hydrogen and $R_{52}$ is methyl. In certain embodiments, $R_{51}$ is methyl and $R_{52}$ is hydrogen. In certain embodiments, $R_{51}$ and $R_{52}$ are each independently optionally substituted alkyl.

As generally described above, each instance of $R_{61}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, optionally substituted heteroaryl, —$OR^{56O}$, or —$N(R^{56N})_2$. In certain embodiments, $R_{61}$ is hydrogen. In certain embodiments, $R_{61}$ is optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, optionally substituted heteroaryl, —$OR^{56O}$, or —$N(R^{56N})_2$. In certain embodiments, $R_{61}$ is optionally substituted $C_{1-6}$ alkyl. In certain embodiments, $R_{61}$ is substituted $C_{1-6}$ alkyl. In certain embodiments, $R_{61}$ is unsubstituted $C_{1-6}$ alkyl. In certain embodiments, $R_{61}$ is methyl, ethyl, n-propyl, i-propyl, n-butyl, s-butyl, t-butyl, n-pentyl, t-pentyl, neo-pentyl, i-pentyl, s-pentyl, or 3-pentyl. In some embodiments, $R_{61}$ is optionally substituted $C_{3-6}$ alkenyl. In some embodiments, $R_{61}$ is optionally substituted $C_{3-6}$ alkynyl. In some embodiments, $R_{61}$ is optionally substituted $C_{3-6}$ carbocyclyl, optionally substituted 3- to 6-membered heterocyclyl, optionally substituted aryl, optionally substituted heteroaryl, —$OR^{56O}$, or —$N(R^{56N})_2$. In some embodiments, $R_{61}$ is optionally substituted $C_{3-6}$ carbocyclyl. In some embodiments, $R_{61}$ is optionally substituted 3- to 6-membered heterocyclyl. In some embodiments, $R_{61}$ is optionally substituted 6-membered heterocyclyl with one heteroatom selected from the group consisting of N, O, and S. In some embodiments, $R_{61}$ is optionally substituted 5-membered heterocyclyl with one heteroatom selected from the group consisting of N, O, and S. In some embodiments, $R_{61}$ is optionally substituted aryl. In some embodiments, $R_{61}$ is phenyl. In some embodiments, $R_{61}$ is optionally substituted phenyl of the formula

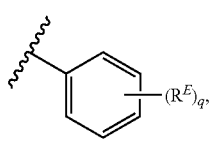

wherein q is 0, 1, 2, 3, 4, or 5; $R^E$ is independently selected from the group consisting of halogen, —CN, —$NO_2$, —$N_3$, optionally substituted alkyl, optionally substituted alkenyl, optionally substituted alkynyl, optionally substituted carbocyclyl, optionally substituted phenyl, optionally substituted heterocyclyl, optionally substituted heteroaryl, optionally substituted alkoxy, an optionally substituted amino group, or an optionally substitute acyl. In certain embodiments, q is 0. In certain embodiments, q is 1. In certain embodiments, q is 2. In certain embodiments, q is 3. In certain embodiments, q is 4. In certain embodiments, q is 5. In certain embodiments, q is 1, and $R^E$ is optionally substituted alkyl or optionally substituted alkoxy. In certain embodiments, q is 1, and $R_{61}$ is one of the formulae:

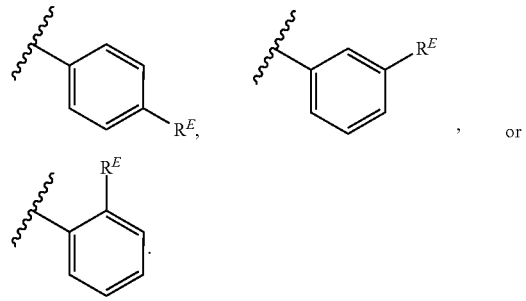

In certain embodiments, q is 2, and $R_{61}$ is one of the formulae:

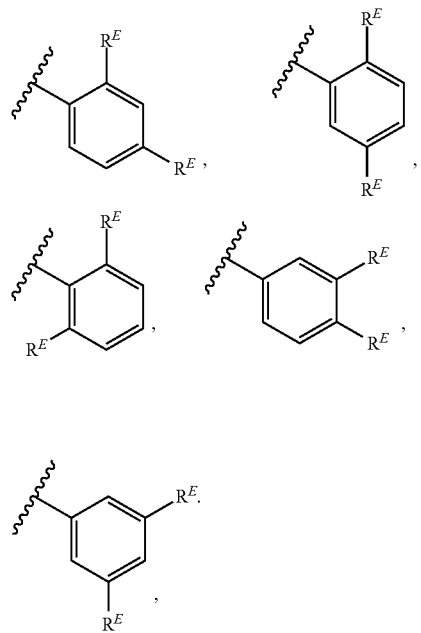

In certain embodiments, q is 3, and $R_{61}$ is one of the formulae:

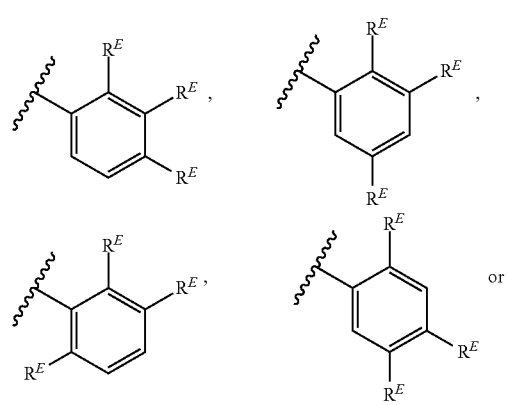

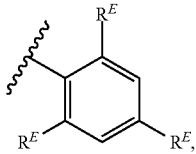

In certain embodiments, q is 4, and $R_{61}$ is one of the formulae:

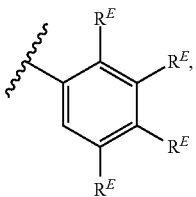

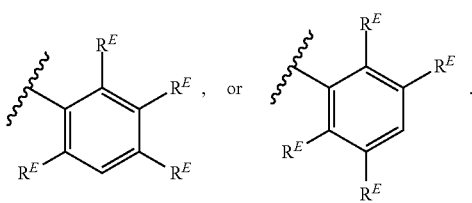

In certain embodiments, q is 5, and $R_{61}$ is of the formula

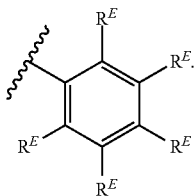

In certain embodiments, $R^E$ is optionally substituted alkyl. In certain embodiments, $R^E$ is methyl, ethyl, or propyl. In certain embodiments, $R^E$ is optionally substituted alkoxy. In certain embodiments, $R^E$ is methoxy or ethoxy. In certain embodiments, $R_{61}$ is one of the following formulae:

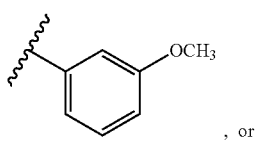
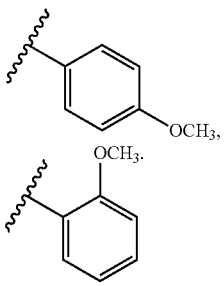

In some embodiments, $R_{61}$ is optionally substituted heteroaryl. In some embodiments, $R_{61}$ is optionally substituted 6-membered heteroaryl with one heteroatom selected from the group consisting of N, O, and S. In some embodiments, $R_{61}$ is optionally substituted 6-membered heteroaryl with two heteroatoms each independently selected from the group consisting of N, O, and S. In some embodiments, $R_{61}$ is optionally substituted 5-membered heteroaryl with one heteroatom selected from the group consisting of N, O, and S. In some embodiments, $R_{61}$ is optionally substituted 5-membered heteroaryl with two heteroatoms each independently selected from the group consisting of N, O, and S.

In some embodiments, $R_{61}$ is —$OR^{56O}$. In some embodiments, $R_{61}$ is —$OR^{56O}$, wherein $R^{56O}$ is independently optionally substituted $C_{1-6}$ alkyl, optionally substituted $C_{3-6}$ carbocyclyl, optionally substituted aryl, optionally substituted heterocyclyl, optionally substituted heteroaryl, or an oxygen protecting group. In certain embodiments, $R_{61}$ is —$OR^{56O}$, wherein $R^{56O}$ is optionally substituted $C_{1-6}$ alkyl. In certain embodiments, $R_{61}$ is —$OR^{56O}$, wherein $R^{56O}$ is unsubstituted $C_{1-6}$ alkyl. In certain embodiments, $R_{61}$ is —O-methyl, —O-ethyl, —O-propyl, —O-isopropyl, —O-isobutyl, or —O-isoamyl. In certain embodiments, $R_{61}$ is —$O(CH_2CH_2O)_sCH_3$, wherein s is 1, 2, 3, or 4. In certain embodiments, $R_{61}$ is —O—$CH_2CH_2O$—$CH_3$. In certain embodiments, $R_{61}$ is —$O(CH_2CH_2O)_2CH_3$. In certain embodiments, $R_{61}$ is —$O(CH_2CH_2O)_3CH_3$. In certain embodiments, $R_{61}$ is —$O(CH_2CH_2O)_4CH_3$. In certain embodiments, $R_{61}$ is —$OR^{56O}$, wherein $R^{56O}$ is optionally substituted $C_{3-6}$ alkenyl. In certain embodiments, $R_{61}$ is —$OR^{56O}$, wherein $R^{56O}$ is optionally substituted $C_{3-6}$ alkynyl. In certain embodiments, $R_{61}$ is —$OR^{56O}$, wherein $R^{56O}$ is optionally substituted 3- to 6-membered heterocyclyl. In certain embodiments, $R_{61}$ is —$OR^{56O}$, wherein $R^{56O}$ is optionally substituted aryl. In certain embodiments, $R_{61}$ is —O-phenyl. In certain embodiments, $R_{61}$ is —$OR^{56O}$, wherein $R^{56O}$ is optionally substituted heteroaryl. In certain embodiments, $R_{61}$ is —$OR^{56O}$, wherein $R^{56O}$ is an oxygen protecting group. In certain embodiments, $R_{61}$ is —$OR^{56O}$, wherein $R^{56O}$ is Ac, Boc, TBS, TIPS, Bn, or Bz.

In some embodiments, $R_{61}$ is —$N(R^{56N})_2$. In certain embodiments, $R_{61}$ is —$NHR^{56N}$, wherein $R^{56N}$ is optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, or a nitrogen protecting group. In certain embodiments, $R_{61}$ is —$NHR^{56N}$, wherein $R^{56N}$ is unsubstituted $C_{1-6}$ alkyl. In certain embodiments, $R_{61}$ is —NH-methyl, —NH-ethyl, or —NH-propyl. In certain embodiments, $R_{61}$ is —$NHR^{56N}$, wherein $R^{56N}$ is substituted $C_{1-6}$ alkyl. In certain embodiments, $R_{61}$ is —NH-benzyl. In certain embodiments, $R_{61}$ is —$N(R^{56N})_2$, wherein $R^{56N}$ is optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, or a nitrogen protecting group. In certain embodiments, $R_{61}$ is —$N(R^{56N})_2$, wherein each instance of $R^{56N}$ is independently optionally substituted $C_{1-6}$ alkyl. In certain embodiments, $R_{61}$ is —$N(R^{56N})_2$, wherein each $R^{56N}$ is independently unsubstituted $C_{1-6}$ alkyl. In certain embodiments, $R_{61}$ is —$N(CH_3)R^{56N}$, wherein each $R^{56N}$ is independently optionally substituted $C_{1-6}$ alkyl or or a nitrogen protecting group. In certain embodiments, $R_{61}$ is —$N(CH_2CH_3) R^{56N}$, wherein each $R^{56N}$ is independently optionally substituted $C_{1-6}$ alkyl or a nitrogen protecting group. In certain embodiments, $R_{61}$ is —$N(R^{56N})_2$, wherein each instance $R^{56N}$ is independently selected from the group consisting of methyl, ethyl, isopropyl, isobutyl, isoamyl, and benzyl. In some embodiments, $R_{61}$ is —$N(R^{56N})_2$, wherein each instance of $R^{56N}$ is the same. In some embodiments, $R_{61}$ is —N($R^{56N}$)$_2$, wherein each instance of $R^{56N}$ is different. In certain embodiments, $R_{61}$ is —NH$_2$. In certain embodiments, $R^{56N}$ is a nitrogen protecting group. In certain embodiments, $R^{56N}$ is Bn, BOC, Cbz, Fmoc, trifluoroacetyl, triphenylmethyl, or Ts.

In some embodiments, two $R_{61}$ are optionally taken together with the intervening atoms to form an optionally substituted heterocyclic ring. In some embodiments, two $R_{61}$ are taken together with the intervening atoms to form an optionally substituted 5-membered heterocyclic ring. In some embodiments, two $R_{61}$ are taken together with the intervening atoms to form an optionally substituted 5-membered heterocyclic ring with one heteroatom selected from the group consisting of S, O, and N. In some embodiments, two $R_{61}$ are taken together with the intervening atoms to form an optionally substituted 5-membered heterocyclic ring with one N. In some embodiments, two $R_{61}$ are taken together with the intervening atoms to form an optionally substituted 5-membered heterocyclic ring with two heteroatoms each independently selected from the group consisting of S, O, and N. In some embodiments, two $R_{61}$ are taken together with the intervening atoms to form an optionally substituted 6-membered heterocyclic ring. In some embodiments, two $R_{61}$ are taken together with the intervening atoms to form an optionally substituted 6-membered heterocyclic ring with one heteroatom selected from the group consisting of S, O, and N. In some embodiments, two $R_{61}$ are taken together with the intervening atoms to form an optionally substituted 6-membered heterocyclic ring with two heteroatoms each independently selected from the group consisting of S, O, and N. In some embodiments, two $R_{61}$ are taken together with the intervening atoms to form an optionally substituted bicyclic heterocyclic ring with one heteroatom selected from the group consisting of S, O, and N. In some embodiments, two $R_{61}$ are taken together with the intervening atoms to form an optionally substituted bicyclic heterocyclic ring with one N. In some embodiments, two $R_{61}$ are taken together with the intervening atoms to form an optionally substituted heterocyclic ring of the formula

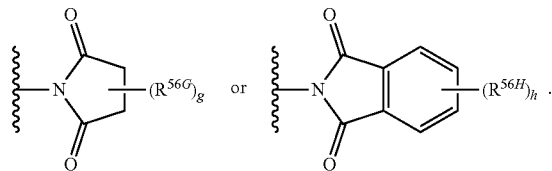

In some embodiments, two $R_{61}$ are taken together with the intervening atoms to form a heterocyclic ring of the formula

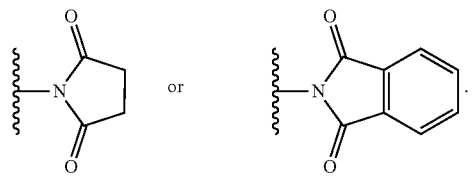 [SMILES: *N1C(=O)CCC1=O ; *N1C(=O)c2ccccc2C1=O]

As generally described above, each instance of $R_{62}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, optionally substituted heteroaryl, —OR$^{56O}$, or —N(R$^{56N}$)$_2$. In certain embodiments, $R_{62}$ is hydrogen. In certain embodiments, $R_{62}$ is optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, optionally substituted heteroaryl, —OR$^{56O}$, or —N(R$^{56N}$)$_2$. In certain embodiments, $R_{62}$ is optionally substituted $C_{1-6}$ alkyl. In certain embodiments, $R_{62}$ is substituted $C_{1-6}$ alkyl. In certain embodiments, $R_{62}$ is unsubstituted $C_{1-6}$ alkyl. In certain embodiments, $R_{62}$ is methyl, ethyl, n-propyl, i-propyl, n-butyl, s-butyl, t-butyl, n-pentyl, t-pentyl, neo-pentyl, i-pentyl, s-pentyl, or 3-pentyl. In certain embodiments, $R_{62}$ is methyl. In some embodiments, $R_{62}$ is optionally substituted $C_{3-6}$ alkenyl. In some embodiments, $R_{62}$ is optionally substituted $C_{3-6}$ alkynyl. In some embodiments, $R_{62}$ is optionally substituted $C_{3-6}$ carbocyclyl. In some embodiments, $R_{62}$ is cyclopropyl or cyclobutyl. In some embodiments, $R_{62}$ is optionally substituted 3- to 6-membered heterocyclyl. In some embodiments, $R_{62}$ is optionally substituted 6-membered heterocyclyl with one heteroatom selected from the group consisting of N, O, and S. In some embodiments, $R_{62}$ is optionally substituted 5-membered heterocyclyl with one heteroatom selected from the group consisting of N, O, and S. In some embodiments, $R_{62}$ is optionally substituted aryl. In some embodiments, $R_{62}$ is phenyl. In some embodiments, $R_{62}$ is optionally substituted phenyl of the formula

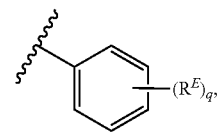

wherein q is 0, 1, 2, 3, 4, or 5; $R^E$ is independently selected from the group consisting of halogen, —CN, —NO$_2$, —N$_3$, optionally substituted alkyl, optionally substituted alkenyl, optionally substituted alkynyl, optionally substituted carbocyclyl, optionally substituted phenyl, optionally substituted heterocyclyl, optionally substituted heteroaryl, optionally substituted alkoxy, an optionally substituted amino group, or an optionally substituted acyl. In certain embodiments, q is 0. In certain embodiments, q is 1. In certain embodiments, q is 2. In certain embodiments, q is 3. In certain embodiments, q is 4. In certain embodiments, q is 5. In certain embodiments, q is 1 and $R^E$ is optionally substituted alkyl or optionally substituted alkoxy. In certain embodiments, q is 1, and $R_{62}$ is one of the formulae:

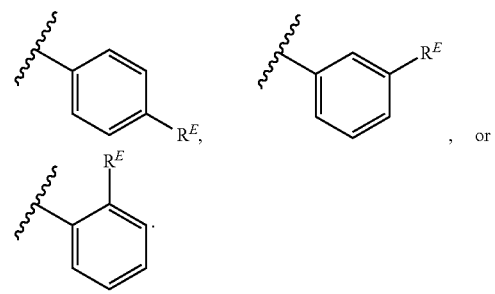

In certain embodiments, q is 2, and $R_{62}$ is one of the formulae:

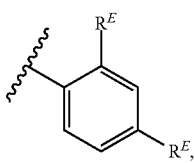

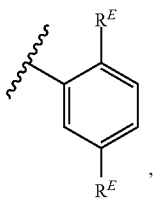
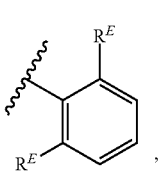

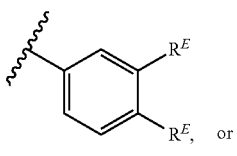
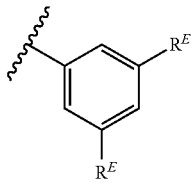

In certain embodiments, q is 3, and $R_{62}$ is one of the formulae:

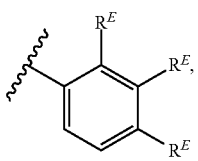
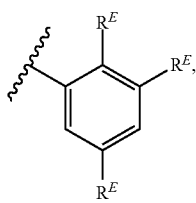

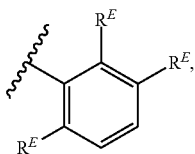

In certain embodiments, q is 4, and $R_{62}$ is one of the formulae:

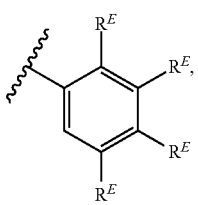
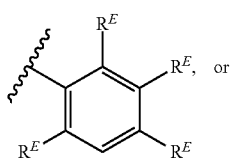

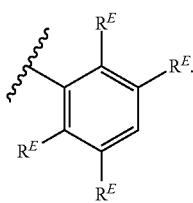

In certain embodiments, q s 5, and $R_{62}$ is of the formula

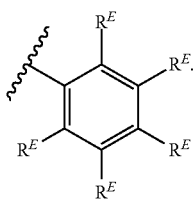

In certain embodiments, $R^E$ is optionally substituted alkyl. In certain embodiments, $R^E$ is methyl, ethyl, or propyl. In certain embodiments, $R^E$ is optionally substituted alkoxy. In certain embodiments, $R^E$ is methoxy or ethoxy. In certain embodiments, $R_{62}$ is one of the following formulae:

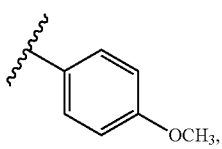 [SMILES: *c1ccc(OC)cc1]

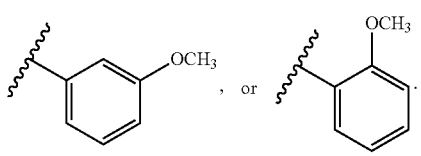 [SMILES: *c1cccc(OC)c1 ; *c1ccccc1OC]

In some embodiments, $R_{62}$ is optionally substituted heteroaryl. In some embodiments, $R_{62}$ is optionally substituted 6-membered heteroaryl with one heteroatom selected from the group consisting of N, O, and S. In some embodiments, $R_{62}$ is optionally substituted 6-membered heteroaryl with two heteroatoms each independently selected from the group consisting of N, O, and S. In some embodiments, $R_{62}$ is optionally substituted 5-membered heteroaryl with one heteroatom selected from the group consisting of N, O, and S. In some embodiments, $R_{62}$ is optionally substituted 5-membered heteroaryl with two heteroatoms each independently selected from the group consisting of N, O, and S.

In some embodiments, $R_{62}$ is —$OR^{56O}$. In some embodiments, $R_{62}$ is —$OR^{56O}$, wherein $R^{56O}$ is independently optionally substituted $C_{1-6}$ alkyl, optionally substituted $C_{3-6}$ carbocyclyl, optionally substituted aryl, optionally substituted heterocyclyl, optionally substituted heteroaryl, or an oxygen protecting group. In certain embodiments, $R_{62}$ is —$OR^{56O}$, wherein $R^{56O}$ is optionally substituted $C_{1-6}$ alkyl. In certain embodiments, $R_{62}$ is —$OR^{56O}$, wherein $R^{56O}$ is unsubstituted $C_{1-6}$ alkyl. In certain embodiments, $R_{62}$ is —O-methyl, —O-ethyl, —O-propyl, —O-isopropyl, —O-isobutyl, or —O-isoamyl. In certain embodiments, $R_{62}$ is —O(CH$_2$CH$_2$O)$_s$CH$_3$, wherein s is 1, 2, 3, or 4. In certain embodiments, R$_{62}$ is —O—CH$_2$CH$_2$O—CH$_3$. In certain embodiments, R$_{62}$ is —O(CH$_2$CH$_2$O)$_2$CH$_3$. In certain embodiments, R$_{62}$ is —O(CH$_2$CH$_2$O)$_3$CH$_3$. In certain embodiments, R$_{62}$ is —O(CH$_2$CH$_2$O)$_4$CH$_3$. In certain embodiments, R$_{62}$ is —OR$^{56O}$, wherein R$^{56O}$ is optionally substituted C$_{3-6}$ alkenyl. In certain embodiments, R$_{62}$ is —OR$^{56O}$, wherein R$^{56O}$ is optionally substituted C$_{3-6}$ alkynyl. In certain embodiments, R$_{62}$ is —OR$^{56O}$, wherein R$^{56O}$ is optionally substituted 3- to 6-membered heterocyclyl. In certain embodiments, R$_{62}$ is —OR$^{56O}$, wherein R$^{56O}$ is optionally substituted aryl. In certain embodiments, R$_{62}$ is —O-phenyl. In certain embodiments, R$_{62}$ is —OR$^{56O}$, wherein R$^{56O}$ is optionally substituted heteroaryl. In certain embodiments, R$_{62}$ is —OR$^{56O}$, wherein R$^{56O}$ is an oxygen protecting group. In certain embodiments, R$_{62}$ is —OR$^{56O}$, wherein R$^{56O}$ is Ac, Boc, TBS, TIPS, Bn, or Bz.

In some embodiments, R$_{62}$ is —N(R$^{56N}$)$_2$. In certain embodiments, R$_{62}$ is —NHR$^{56N}$, wherein R$^{56N}$ is optionally substituted C$_{1-6}$ alkyl, optionally substituted C$_{3-6}$ alkenyl, optionally substituted C$_{3-6}$ alkynyl, optionally substituted C$_{3-6}$ carbocyclyl, optionally substituted aryl, optionally substituted 3- to 6-membered heterocyclyl, optionally substituted heteroaryl, or a nitrogen protecting group. In certain embodiments, R$_{62}$ is —NHR$^{56N}$, wherein R$^{56N}$ is unsubstituted C$_{1-6}$ alkyl. In certain embodiments, R$_{62}$ is —NH-methyl, —NH-ethyl, or —NH-propyl. In certain embodiments, R$_{62}$ is —NHR$^{56N}$, wherein R$^{56N}$ is substituted C$_{1-6}$ alkyl. In certain embodiments, R$_{62}$ is —NH-benzyl. In certain embodiments, R$_{62}$ is —N(R$^{56N}$)$_2$, wherein R$^{56N}$ is optionally substituted C$_{1-6}$ alkyl, optionally substituted C$_{3-6}$ alkenyl, optionally substituted C$_{3-6}$ alkynyl, optionally substituted C$_{3-6}$ carbocyclyl, optionally substituted aryl, optionally substituted 3- to 6-membered heterocyclyl, optionally substituted heteroaryl, or a nitrogen protecting group. In certain embodiments, R$_{62}$ is —N(R$^{56N}$)$_2$, wherein each instance of R$^{56N}$ is independently optionally substituted C$_{1-6}$ alkyl. In certain embodiments, R$_{62}$ is —N(R$^{56N}$)$_2$, wherein each R$^{56N}$ is independently unsubstituted C$_{3-6}$ alkyl. In certain embodiments, R$_{62}$ is —N(CH$_3$)R$^{56N}$, wherein each R$^{56N}$ is independently optionally substituted C$_{1-6}$ alkyl or or a nitrogen protecting group. In certain embodiments, R$_{62}$ is —N(CH$_2$CH$_3$) R$^{56N}$, wherein each R$^{56N}$ is independently optionally substituted C$_{1-6}$ alkyl or a nitrogen protecting group. In certain embodiments, R$_{62}$ is —N(R$^{56N}$)$_2$, wherein each instance R$^{56N}$ is independently selected from the group consisting of methyl, ethyl, isopropyl, isobutyl, isoamyl, and benzyl. In some embodiments, R$_{62}$ is —N(R$^{56N}$)$_2$, wherein each instance of R$^{56N}$ is the same. In some embodiments, R$_{62}$ is —N(R$^{56N}$)$_2$, wherein each instance of R$^{56N}$ is different. In certain embodiments, R$_{62}$ is —NH$_2$. In certain embodiments, R$^{56N}$ is a nitrogen protecting group. In certain embodiments, R$^{56N}$ is Bn, BOC, Cbz, Fmoc, trifluoroacetyl, triphenylmethyl, or Ts.

In some embodiments, two R$_{62}$ are optionally taken together with the intervening atoms to form an optionally substituted heterocyclic ring. In some embodiments, two R$_{62}$ are taken together with the intervening atoms to form an optionally substituted 5-membered heterocyclic ring. In some embodiments, two R$_{62}$ are taken together with the intervening atoms to form an optionally substituted 5-membered heterocyclic ring with one heteroatom selected from the group consisting of S, O, and N. In some embodiments, two R$_{62}$ are taken together with the intervening atoms to form an optionally substituted 5-membered heterocyclic ring with one N. In some embodiments, two R$_{62}$ are taken together with the intervening atoms to form an optionally substituted 5-membered heterocyclic ring with two heteroatoms each independently selected from the group consisting of S, O, and N. In some embodiments, two R$_{62}$ are taken together with the intervening atoms to form an optionally substituted 6-membered heterocyclic ring. In some embodiments, two R$_{62}$ are taken together with the intervening atoms to form an optionally substituted 6-membered heterocyclic ring with one heteroatom selected from the group consisting of S, O, and N. In some embodiments, two R$_{62}$ are taken together with the intervening atoms to form an optionally substituted 6-membered heterocyclic ring with two heteroatoms each independently selected from the group consisting of S, O, and N. In some embodiments, two R$_{62}$ are taken together with the intervening atoms to form an optionally substituted bicyclic heterocyclic ring with one heteroatom selected from the group consisting of S, O, and N. In some embodiments, two R$_{62}$ are taken together with the intervening atoms to form an optionally substituted bicyclic heterocyclic ring with one N. In some embodiments, two R$_{62}$ are taken together with the intervening atoms to form an optionally substituted heterocyclic ring of the formula

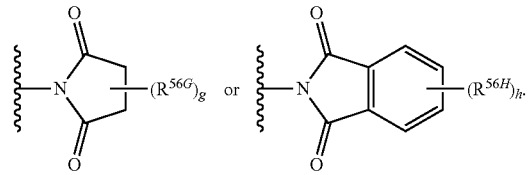

In some embodiments, two R$_{62}$ are taken together with the intervening atoms to form a heterocyclic ring of the formula

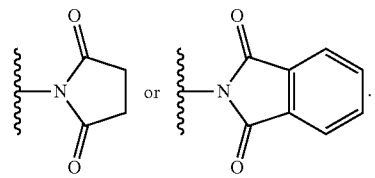

In certain embodiments, R$_{61}$ and R$_{62}$ are the same. In certain embodiments, R$_{61}$ and R$_{62}$ are optionally substituted alkyl. In certain embodiments, R$_{61}$ and R$_{62}$ are different. In certain embodiments, R$_{61}$ and R$_{62}$ are each independently optionally substituted alkyl. In certain embodiments, R$_{61}$ and R$_{62}$ are both methyl. In certain embodiments, R$_{61}$ and R$_{62}$ are each independently —O(CH$_2$CH$_2$O)$_s$CH$_3$, wherein s is 1, 2, 3, or 4. In certain embodiments, R$_{61}$ and R$_{62}$ are —OCH$_2$CH$_2$OCH$_3$. In certain embodiments, R$_{61}$ and R$_{62}$ are —O(CH$_2$CH$_2$O)$_2$CH$_3$. In certain embodiments, R$_{61}$ and R$_{62}$ are —O(CH$_2$CH$_2$O)$_3$CH$_3$. In certain embodiments, R$_{61}$ and R$_{62}$ are —O(CH$_2$CH$_2$O)$_4$CH$_3$. In certain embodiments, R$_{62}$ is optionally substituted C$_{1-6}$ alkyl; and R$_{61}$ is —OR$^{56O}$, wherein R$^{56O}$ is optionally substituted alkyl. In certain embodiments, R$_{62}$ is methyl, ethyl, n-propyl, i-propyl, n-butyl, s-butyl, t-butyl, n-pentyl, t-pentyl, neo-pentyl, i-pentyl, s-pentyl, or 3-pentyl; ; and R$_{61}$ is —OR$^{56O}$, wherein R$^{56O}$ is methyl, ethyl, n-propyl, or i-propy. In certain embodiments, R$_{61}$ is optionally substituted C$_{1-6}$ alkyl; and R$_{62}$ is —OR$^{56O}$. In certain embodiments, R$_{61}$ is methyl, ethyl, n-propyl, i-propyl, n-butyl, s-butyl, t-butyl, n-pentyl, t-pentyl, neo-pentyl, i-pentyl, s-pentyl, or 3-pentyl; ; and R$_{62}$ is —OR$^{56O}$, wherein R$^{56O}$ is methyl, ethyl, n-propyl, or i-propy. In certain embodiments, R$_{61}$ and R$_{62}$ are each independently —OR$^{56O}$, wherein R$^{56O}$ is optionally substituted alkyl. In certain embodiments, R$_{61}$ and R$_{62}$ are each independently —OR$^{56O}$, wherein R$^{56O}$ is methyl, ethyl, n-propyl, or i-propy.

As generally described above, each instance of R$_{63}$ is independently hydrogen, optionally substituted C$_{1-6}$ alkyl, optionally substituted C$_{3-6}$ alkenyl, optionally substituted C$_{3-6}$ alkynyl, optionally substituted C$_{3-6}$ carbocyclyl, optionally substituted 3- to 6-membered heterocyclyl, optionally substituted aryl, optionally substituted heteroaryl, —OR$^{56O}$, or —N(R$^{56N}$)$_2$. In certain embodiments, R$_{63}$ is hydrogen. In certain embodiments, R$_{63}$ is optionally substituted C$_{1-6}$ alkyl, optionally substituted C$_{3-6}$ alkenyl, optionally substituted C$_{3-6}$ alkynyl, optionally substituted C$_{3-6}$ carbocyclyl, optionally substituted 3- to 6-membered heterocyclyl, optionally substituted aryl, optionally substituted heteroaryl, —OR$^{56O}$, or —N(R$^{56N}$)$_2$. In certain embodiments, R$_{63}$ is optionally substituted C$_{1-6}$ alkyl. In certain embodiments, R$_{63}$ is substituted C$_{1-6}$ alkyl. In certain embodiments, R$_{63}$ is unsubstituted C$_{1-6}$ alkyl. In certain embodiments, R$_{63}$ is methyl, ethyl, or propyl. In some embodiments, R$_{63}$ is optionally substituted C$_{3-6}$ alkenyl. In some embodiments, R$_{63}$ is substituted C$_{3-6}$ alkenyl. In some embodiments, R$_{63}$ is unsubstituted C$_{3-6}$ alkenyl. In some embodiments, R$_{63}$ is allyl, crotyl, or vinyl. In some embodiments, R$_{63}$ is optionally substituted C$_{3-6}$ alkynyl. In some embodiments, R$_{63}$ is ethynyl, propargyl, or propynyl. In some embodiments, R$_{63}$ is optionally substituted C$_{3-6}$ carbocyclyl, optionally substituted 3- to 6-membered heterocyclyl, optionally substituted aryl, optionally substituted heteroaryl, —OR$^{56O}$, or —N(R$^{56N}$)$_2$. In some embodiments, R$_{63}$ is optionally substituted C$_{3-6}$ carbocyclyl. In some embodiments, R$_{63}$ is cyclopropyl or cyclobutyl. In some embodiments, R$_{63}$ is optionally substituted 3- to 6-membered heterocyclyl. In some embodiments, R$_{63}$ is optionally substituted 6-membered heterocyclyl with one heteroatom selected from the group consisting of N, O, and S. In some embodiments, R$_{63}$ is optionally substituted 5-membered heterocyclyl with one heteroatom selected from the group consisting of N, O, and S. In some embodiments, R$_{63}$ is optionally substituted aryl. In some embodiments, R$_{63}$ is phenyl. In some embodiments, R$_{63}$ is optionally substituted phenyl of the formula

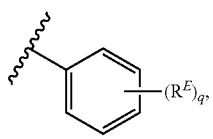

wherein q is 0, 1, 2, 3, 4, or 5; R$^E$ is independently selected from the group consisting of halogen, —CN, —NO$_2$, —N$_3$, optionally substituted alkyl, optionally substituted alkenyl, optionally substituted alkynyl, optionally substituted carbocyclyl, optionally substituted phenyl, optionally substituted heterocyclyl, optionally substituted heteroaryl, optionally substituted alkoxy, an optionally substituted amino group, or an optionally substituted acyl. In certain embodiments, q is 0. In certain embodiments, q is 1. In certain embodiments, q is 2. In certain embodiments, q is 3. In certain embodiments, q is 4. In certain embodiments, q is 5. In certain embodiments, q is 1 and R$^E$ is optionally substituted alkyl or optionally substituted alkoxy. In certain embodiments, q is 1, and R$_{63}$ is one of the formulae:

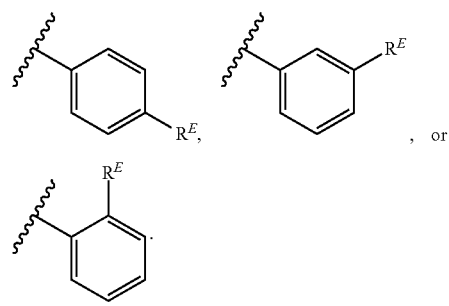

In certain embodiments, q is 2, and R$_{63}$ is one of the formulae:

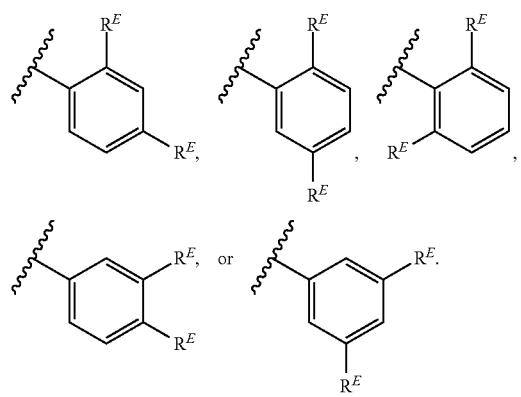

In certain embodiments, q is 3, and R$_{63}$ is one of the formulae:

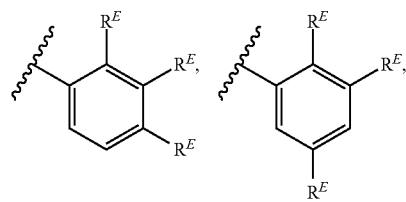

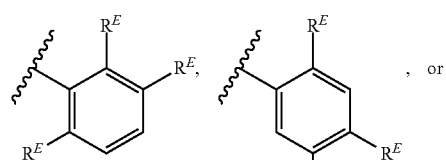

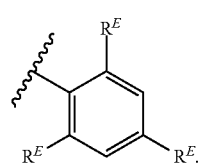

In certain embodiments, q is 4, and R$_{63}$ is one of the formulae:

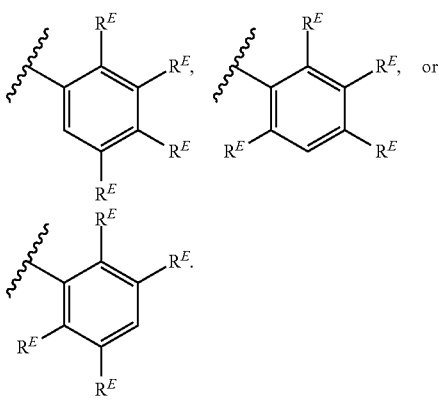

In certain embodiments, q is 5, and $R_{63}$ is of the formula

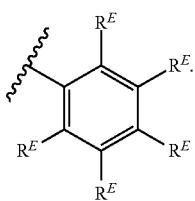

In certain embodiments, $R^E$ is optionally substituted alkyl. In certain embodiments, $R^E$ is methyl, ethyl, or propyl. In certain embodiments, $R^E$ is optionally substituted alkoxy. In certain embodiments, $R^E$ is methoxy or ethoxy. In certain embodiments, $R_{63}$ is one of the following formulae:

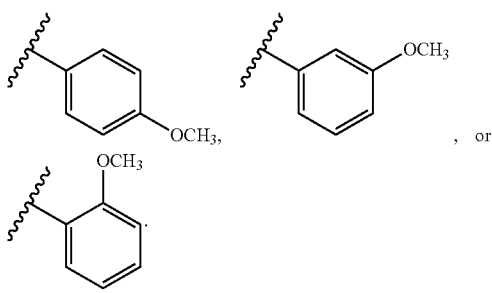

In some embodiments, $R_{63}$ is optionally substituted heteroaryl. In some embodiments, $R_{63}$ is optionally substituted 6-membered heteroaryl with one heteroatom selected from the group consisting of N, O, and S. In some embodiments, $R_{63}$ is optionally substituted 6-membered heteroaryl with two heteroatoms each independently selected from the group consisting of N, O, and S. In some embodiments, $R_{63}$ is optionally substituted 5-membered heteroaryl with one heteroatom selected from the group consisting of N, O, and S. In some embodiments, $R_{63}$ is optionally substituted 5-membered heteroaryl with two heteroatoms each independently selected from the group consisting of N, O, and S.

In some embodiments, $R_{63}$ is —$OR^{56O}$. In some embodiments, $R_{63}$ is —$OR^{56O}$, wherein $R^{56O}$ is independently optionally substituted $C_{1-6}$ alkyl, optionally substituted $C_{3-6}$ carbocyclyl, optionally substituted aryl, optionally substituted heterocyclyl, optionally substituted heteroaryl, or an oxygen protecting group. In certain embodiments, $R_{63}$ is —$OR^{56O}$, wherein $R^{56O}$ is optionally substituted $C_{1-6}$ alkyl.

In certain embodiments, $R_{63}$ is —$OR^{56O}$, wherein $R^{56O}$ is unsubstituted $C_{1-6}$ alkyl. In certain embodiments, $R_{63}$ is —O-methyl, —O-ethyl, —O-propyl, —O-isopropyl, —O-isobutyl, or —O-isoamyl. In certain embodiments, $R_{63}$ is —$O(CH_2CH_2O)_sCH_3$, wherein s is 1, 2, 3, or 4. In certain embodiments, $R_{63}$ is —O—$CH_2CH_2O$—$CH_3$. In certain embodiments, $R_{63}$ is —$O(CH_2CH_2O)_2CH_3$. In certain embodiments, $R_{63}$ is —O $(CH_2CH_2O)_3CH_3$. In certain embodiments, $R_{63}$ is —$O(CH_2CH_2O)_4CH_3$. In certain embodiments, $R_{63}$ is —$O(CH_2CH_2O)_4CH_3$. In certain embodiments, $R_{63}$ is —$OR^{56O}$, wherein $R^{56O}$ is optionally substituted $C_{3-6}$ alkenyl. In certain embodiments, $R_{63}$ is —$OR^{56O}$, wherein $R^{56O}$ is optionally substituted $C_{3-6}$ alkynyl. In certain embodiments, $R_{63}$ is —$OR^{56O}$, wherein $R^{56O}$ is optionally substituted 3- to 6-membered heterocyclyl. In certain embodiments, $R_{63}$ is —$OR^{56O}$, wherein $R^{56O}$ is optionally substituted aryl. In certain embodiments, $R_{63}$ is —O-phenyl. In certain embodiments, $R_{63}$ is —$OR^{56O}$, wherein $R^{56O}$ is optionally substituted heteroaryl. In certain embodiments, $R_{63}$ is —$OR^{56O}$, wherein $R^{56O}$ is an oxygen protecting group. In certain embodiments, $R_{63}$ is —$OR^{56O}$, wherein $R^{56O}$ is Ac, Boc, TBS, TIPS, Bn, or Bz.

In some embodiments, $R_{63}$ is —$N(R^{56N})_2$. In certain embodiments, $R_{63}$ is —$NHR^{56N}$, wherein $R^{56N}$ is optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, or a nitrogen protecting group. In certain embodiments, $R_{63}$ is —$NHR^{56N}$, wherein $R^{56N}$ is unsubstituted $C_{1-6}$ alkyl. In certain embodiments, $R_{63}$ is —NH-methyl, —NH-ethyl, or —NH-propyl. In certain embodiments, $R_{63}$ is —$NHR^{56N}$, wherein $R^{56N}$ is substituted $C_{1-6}$ alkyl. In certain embodiments, $R_{63}$ is —NH-benzyl. In certain embodiments, $R_{63}$ is —$N(R^{56N})_2$, wherein $R^{56N}$ is optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, or a nitrogen protecting group. In certain embodiments, $R_{63}$ is —$N(R^{56N})_2$, wherein each instance of $R^{56N}$ is independently optionally substituted $C_{1-6}$ alkyl. In certain embodiments, $R_{63}$ is —$N(R^{56N})_2$, wherein each $R^{56N}$ is independently unsubstituted $C_{1-6}$ alkyl. In certain embodiments, $R_{63}$ is —$N(CH_3)R^{56N}$, wherein each $R^{56N}$ is independently optionally substituted $C_{1-6}$ alkyl or or a nitrogen protecting group. In certain embodiments, $R_{63}$ is —$N(CH_2CH_3)R^{56N}$, wherein each $R^{56N}$ is independently optionally substituted $C_{1-6}$ alkyl or a nitrogen protecting group. In certain embodiments, $R_{63}$ is —$N(R^{56N})_2$, wherein each instance $R^{56N}$ is independently selected from the group consisting of methyl, ethyl, isopropyl, isobutyl, isoamyl, and benzyl. In some embodiments, $R_{63}$ is —$N(R^{56N})_2$, wherein each instance of $R^{56N}$ is the same. In some embodiments, $R_{63}$ is —$N(R^{56N})_2$, wherein each instance of $R^{56N}$ is different. In certain embodiments, $R_{63}$ is —$NH_2$. In certain embodiments, $R^{56N}$ is a nitrogen protecting group. In certain embodiments, $R^{56N}$ is Bn, BOC, Cbz, Fmoc, trifluoroacetyl, triphenylmethyl, or Ts.

As generally defined herein, n1 is 1, 2, or 3. In certain embodiments, n1 is 1. In certain embodiments, n1 is 2. In certain embodiments, n1 is 3.

As generally defined herein, n2 is 1, 2, or 3. In certain embodiments, n2 is 1. In certain embodiments, n2 is 2. In certain embodiments, n2 is 3.

In certain embodiments, n1 and n2 are the same. In certain embodiments, n1 and n2 are different. In certain embodiments, n1 and n2 are 1. In certain embodiments, n1 and n2 are 2. In certain embodiments, n1 and n2 are 3. In certain embodiments, n1 is 1 and n2 is 1. In certain embodiments, n1 is 1 and n2 is 2. In certain embodiments, n1 is 1 and n2 is 3.

In certain embodiments, a compound of Formula (I) is of Formula (II) or Formula (III):

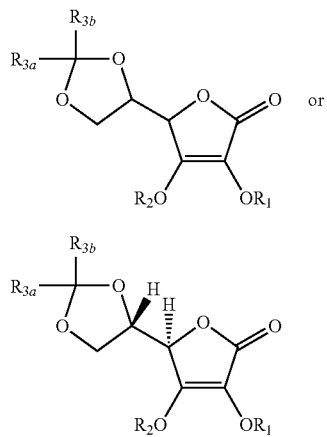

or a pharmaceutically or cosmetically acceptable salt thereof, wherein $R_1$ and $R_2$ are defined as described herein; and each of $R_{3a}$ and $R_{3b}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, or optionally substituted heteroaryl.

As generally defined herein, $R_{3a}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, or optionally substituted heteroaryl. In certain embodiments, $R_{3a}$ is hydrogen. In certain embodiments, $R_{3a}$ is optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, or optionally substituted heteroaryl. In certain embodiments, $R_{3a}$ is optionally substituted $C_{1-6}$ alkyl. In certain embodiments, $R_{3a}$ is substituted $C_{1-6}$ alkyl. In certain embodiments, $R_{3a}$ is unsubstituted $C_{1-6}$ alkyl. In certain embodiments, $R_{3a}$ is methyl, ethyl, or propyl. In certain embodiments, $R_{3a}$ is methyl. In some embodiments, $R_{3a}$ is optionally substituted $C_{3-6}$ alkenyl. In some embodiments, $R_{3a}$ is optionally substituted $C_{3-6}$ alkynyl. In some embodiments, $R_{3a}$ is optionally substituted $C_{3-6}$ carbocyclyl. In some embodiments, $R_{3a}$ is cyclopropyl or cyclobutyl. In some embodiments, $R_{3a}$ is optionally substituted 3- to 6-membered heterocyclyl. In some embodiments, $R_{3a}$ is optionally substituted aryl. In some embodiments, $R_{3a}$ is optionally substituted phenyl. In some embodiments, $R_{3a}$ is phenyl. In some embodiments, $R_{3a}$ is optionally substituted heteroaryl.

As generally defined herein, $R_{3b}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, or optionally substituted heteroaryl. In certain embodiments, $R_{3b}$ is hydrogen. In certain embodiments, $R_{3b}$ is optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, or optionally substituted heteroaryl. In certain embodiments, $R_{3b}$ is optionally substituted $C_{1-6}$ alkyl. In certain embodiments, $R_{3b}$ is substituted $C_{1-6}$ alkyl. In certain embodiments, $R_{3b}$ is unsubstituted $C_{1-6}$ alkyl. In certain embodiments, $R_{3b}$ is methyl, ethyl, or propyl. In certain embodiments, $R_{3b}$ is methyl. In some embodiments, $R_{3b}$ is optionally substituted $C_{3-6}$ alkenyl. In some embodiments, $R_{3b}$ is optionally substituted $C_{3-6}$ alkynyl. In some embodiments, $R_{3b}$ is optionally substituted $C_{3-6}$ carbocyclyl. In some embodiments, $R_{3b}$ is cyclopropyl or cyclobutyl. In some embodiments, $R_{3b}$ is optionally substituted 3- to 6-membered heterocyclyl. In some embodiments, $R_{3b}$ is optionally substituted aryl. In some embodiments, $R_{3b}$ is optionally substituted phenyl. In some embodiments, $R_{3b}$ is phenyl. In some embodiments, $R_{3b}$ is optionally substituted heteroaryl.

In certain embodiments, $R_{3a}$ and $R_{3b}$ are the same. In certain embodiments, $R_{3a}$ and $R_{3b}$ are different. In certain embodiments, $R_{3a}$ and $R_{3b}$ are independently optionally substituted $C_{1-6}$ alkyl. In certain embodiments, $R_{3a}$ and $R_{3b}$ are independently methyl, ethyl, or propyl. In certain embodiments, $R_{3a}$ and $R_{3b}$ are both methyl.

In certain embodiments when the provided compounds are of Formula (I), (II), or (III), $R_1$ is of the formula

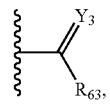

wherein $Y_3$ is O or $NR^{YN}$; $R^{YN}$ is hydrogen or optionally substituted alkyl; and $R_{63}$ is optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, optionally substituted heteroaryl, —$OR^{56O}$, —$N(R^{56N})_2$. In certain embodiments, $R_1$ is of the formula

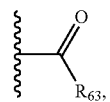

wherein $R_{63}$ is optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, optionally substituted heteroaryl, —$OR^{56O}$, or —$N(R^{56N})_2$. In certain embodiments, $R_1$ is of the formula

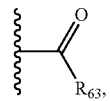

wherein $R_{63}$ is optionally substituted $C_{1-6}$ alkyl or optionally substituted aryl. In certain embodiments, $R_1$ is of the formula

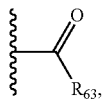

wherein $R_{63}$ is optionally substituted alkyl. In certain embodiments, $R_1$ is of the formula

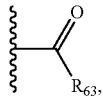

wherein $R_{63}$ is methyl, ethyl, n-propyl, i-propyl, n-butyl, s-butyl, t-butyl, n-pentyl, t-pentyl, neo-pentyl, i-pentyl, s-pentyl, or 3-pentyl. In certain embodiments, $R_1$ is of the formula

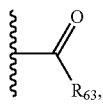

wherein $R_{63}$ is methyl. In certain embodiments, $R_1$ is of the formula

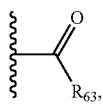

wherein $R_{63}$ is optionally substituted aryl. In certain embodiments, $R_1$ is of the formula

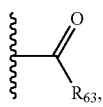

wherein $R_{63}$ is optionally substituted phenyl. In certain embodiments, $R_1$ is of the formula

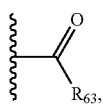

wherein $R_{63}$ is phenyl. In certain embodiments, $R_1$ is of the formula

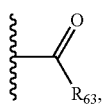

wherein $R_{63}$ is of the formula

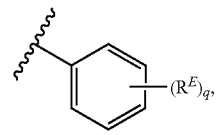

wherein $R^E$ and q are as defined herein. In certain embodiments, $R_1$ is of the formula

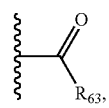

wherein $R_{63}$ is one of the following formulae:

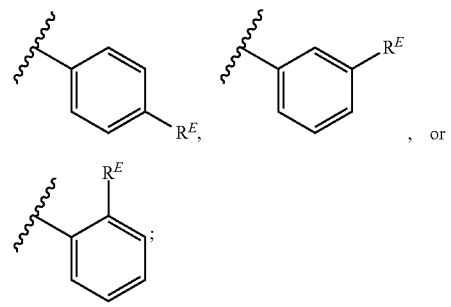

and $R^E$ is optionally substituted alkyl or optionally substituted alkoxy. In certain embodiments, $R_1$ is of the formula

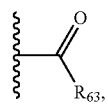

wherein $R_{63}$ is one of the following formulae:

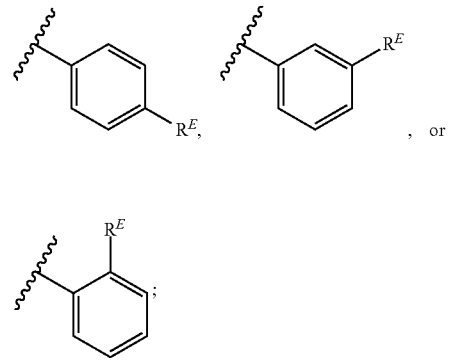

and $R^E$ is optionally substituted alkoxy. In certain embodiments, $R_1$ is of the formula

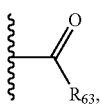

wherein $R_{63}$ is one of the following formulae:

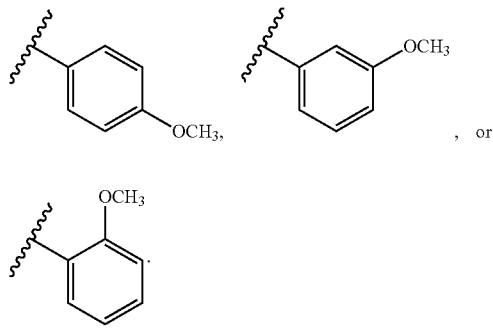

In certain embodiments, $R_1$ is of the formula

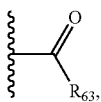

wherein $R_{63}$ is —O-alkyl. In certain embodiments, $R_1$ is of the formula

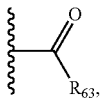

wherein $R_{63}$ is —O-alkyl. In certain embodiments, $R_1$ is of the formula

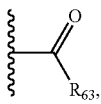

wherein $R_{63}$ is —O(CH$_2$CH$_2$O)$_s$CH$_3$, wherein s is 1, 2, 3, or 4. In certain embodiments, $R_1$ is of the formula

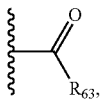

wherein $R_{63}$ is —O—CH$_2$CH$_2$O—CH$_3$, —O(CH$_2$CH$_2$O)$_2$CH$_3$, —O(CH$_2$CH$_2$O)$_3$CH$_3$, or —O(CH$_2$CH$_2$O)$_4$CH$_3$.

In certain embodiments when the provided compounds are of Formula (I), (II), or (III), $R_1$ is of the formula

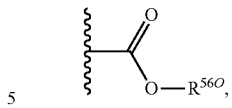

wherein $R^{56O}$ is optionally substituted C$_{1-6}$ alkyl, optionally substituted C$_{3-6}$ alkenyl, optionally substituted C$_{3-6}$ alkynyl, optionally substituted C$_{3-6}$ carbocyclyl, optionally substituted 3- to 6-membered heterocyclyl, optionally substituted aryl, or optionally substituted heteroaryl. In certain embodiments, $R_1$ is of the formula

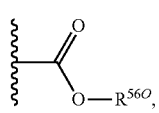

wherein $R^{56O}$ is optionally substituted alkyl. In certain embodiments, $R_1$ is of the formula

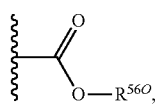

wherein $R^{56O}$ is substituted alkyl. In certain embodiments, $R_1$ is of the formula

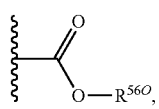

wherein $R^{56O}$ is unsubstituted alkyl. In certain embodiments, $R_1$ is of the formula

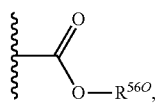

wherein $R^{56O}$ is methyl, ethyl, or propyl. In certain embodiments, $R_1$ is of the formula

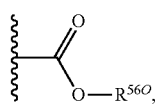

wherein $R^{56O}$ is methyl. In certain embodiments, $R_1$ is of the formula

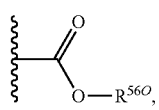

wherein $R^{56O}$ is —(CH$_2$CH$_2$O)$_s$CH$_3$, wherein s is 1, 2, 3, or 4. In certain embodiments, $R_1$ is of the formula

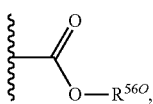

wherein $R^{56O}$ is —CH$_2$CH$_2$OCH$_3$, —(CH$_2$CH$_2$O)$_2$CH$_3$, —(CH$_2$CH$_2$O)$_3$CH$_3$, or —(CH$_2$CH$_2$O)$_4$CH$_3$.

In certain embodiments when the provided compounds are of Formula (I), (II), or (III), $R_1$ is of the formula:

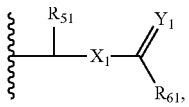

wherein $X_1$ is O or NR$^{XN}$; $Y_1$ is O or NR$^{YN}$; $R^{XN}$ and $R^{XN}$ are each independently hydrogen or optionally substituted alkyl; $R_{51}$ is optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, or optionally substituted heteroaryl; and $R_{61}$ is optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, optionally substituted heteroaryl, —OR$^{56O}$, or —N(R$^{56N}$)$_2$. In certain embodiments, $R_1$ is of the formula

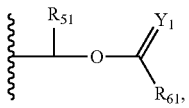

wherein $Y_1$ is O or NR$^{RN}$; $R^{RN}$ is hydrogen or optionally substituted alkyl; $R_{51}$ is hydrogen, optionally substituted alkyl, optionally substituted heterocyclyl, optionally substituted aryl, or optionally substituted heteroaryl; and $R_{61}$ is optionally substituted alkyl, optionally substituted heterocyclyl, optionally substituted aryl, optionally substituted heteroaryl, or optionally substituted alkoxy. In certain embodiments, $R_1$ is of the formula

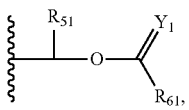

wherein $Y_1$ is O; $R_{51}$ is hydrogen, optionally substituted $C_{1-6}$ alkyl; and $R_{61}$ is optionally substituted $C_{1-6}$ alkyl, optionally substituted aryl, or —OR$^{56O}$. In certain embodiments, $R_1$ is of the formula

wherein $R_{61}$ is optionally substituted $C_{1-6}$ alkyl, optionally substituted heterocyclyl, optionally substituted aryl, optionally substituted 3- to 6-membered heteroaryl, or —OR$^{56O}$. In certain embodiments, $R_1$ is of the formula

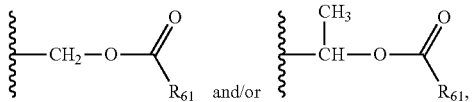

wherein $R_{61}$ is optionally substituted $C_{1-6}$ alkyl, optionally substituted heterocyclyl, optionally substituted aryl, optionally substituted 3- to 6-membered heteroaryl, or —OR$^{56O}$. In certain embodiments, $R_1$ is of the formula:

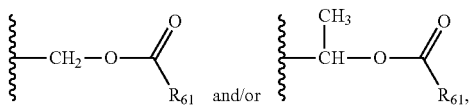

wherein $R_{61}$ is optionally substituted $C_{1-6}$ alkyl. In certain embodiments, $R_1$ is of the formula:

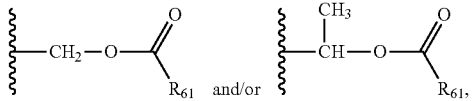

wherein $R_{61}$ is methyl, ethyl, n-propyl, i-propyl, n-butyl, s-butyl, t-butyl, n-pentyl, t-pentyl, neo-pentyl, i-pentyl, s-pentyl, or 3-pentyl. In certain embodiments, $R_1$ is of the formula:

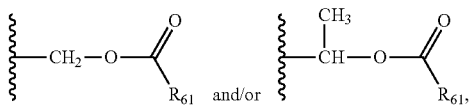

wherein $R_{61}$ is optionally substituted aryl. In certain embodiments, $R_1$ is of the formula:

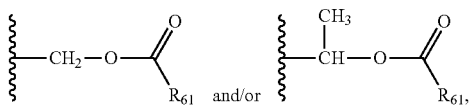

wherein $R_{61}$ is substituted phenyl of the formula:

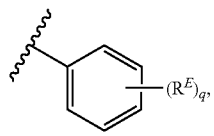

wherein $R^E$ and q are as defined herein. In certain embodiments, $R_1$ is of the formula:

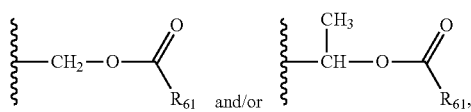

wherein $R_{61}$ is optionally substituted $C_{1-6}$ alkyl, optionally substituted heterocyclyl, optionally substituted aryl, optionally substituted 3- to 6-membered heteroaryl, or $-OR^{56O}$. In certain embodiments, $R_1$ is of the formula:

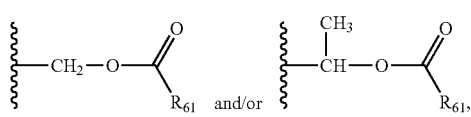

wherein $R_{61}$ is optionally substituted $C_{1-6}$ alkyl. In certain embodiments, $R_1$ is of the formula:

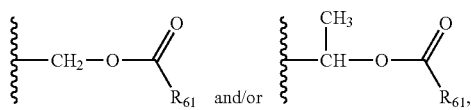

wherein $R_{61}$ is methyl, ethyl, n-propyl, i-propyl, n-butyl, s-butyl, t-butyl, n-pentyl, t-pentyl, neo-pentyl, i-pentyl, s-pentyl, or 3-pentyl. In certain embodiments, $R_1$ is of the formula:

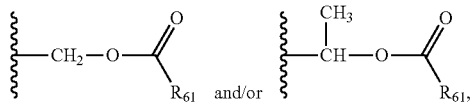

wherein $R_{61}$ is optionally substituted aryl. In certain embodiments, $R_1$ is of the formula:

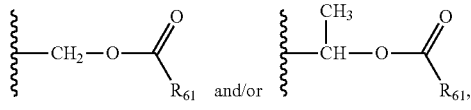

wherein $R_{61}$ is selected from one of the following formulae:

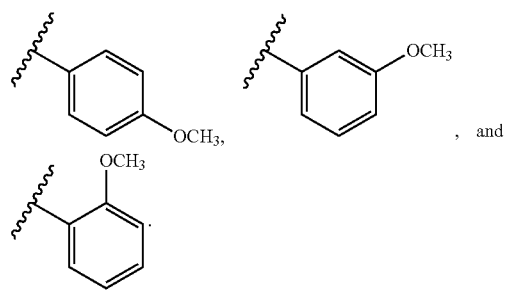

In certain embodiments, $R_1$ is of the formula

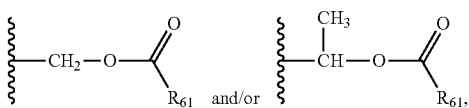

wherein $R_{61}$ is $-OR^{56O}$. In certain embodiments, $R_1$ is of the formula:

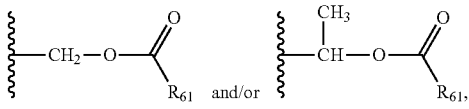

wherein $R_{61}$ is methoxy, ethoxy, n-propyloxy, or 2-propyloxy. In certain embodiments, $R_1$ is of the formula:

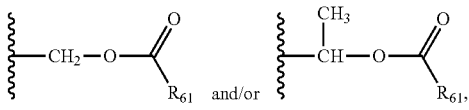

wherein $R_{61}$ is $-O(CH_2CH_2O)_sCH_3$, wherein s is 1, 2, 3, or 4. In certain embodiments, $R_1$ is of the formula:

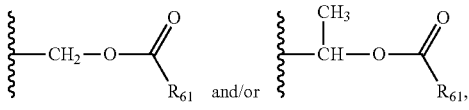

wherein $R_{61}$ is $-OCH_2CH_2OCH_3$, $-O(CH_2CH_2O)_2CH_3$, $-O(CH_2CH_2O)_3CH_3$, or $-O(CH_2CH_2O)_4CH_3$.

In certain embodiments when the provided compounds are of Formula (I), (II), or (III), $R_1$ is of Formula (B):

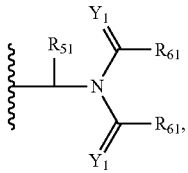

wherein two $R_{61}$ are taken together with their intervening atoms to form an optionally substituted heterocyclic ring. In certain embodiments, $R_1$ is of the formula:

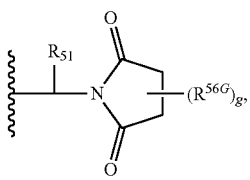

wherein $R_{51}$ is hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, optionally substituted heteroaryl; g is 0, 1, 2, 3, or 4; and each instance of $R^{56G}$ is independently selected from the group consisting of halogen, —CN, —NO$_2$, —N$_3$, optionally substituted alkyl, optionally substituted alkenyl, optionally substituted alkynyl, optionally substituted carbocyclyl, optionally substituted phenyl, optionally substituted heterocyclyl, optionally substituted heteroaryl, optionally substituted alkoxy, or an optionally substituted amino group, or optionally two $R^{56G}$ are taken together with the intervening atoms to form optionally substituted aryl, heteroaryl, carbocyclyl, or heterocyclyl. In certain embodiments, R$_1$ is of the formula:

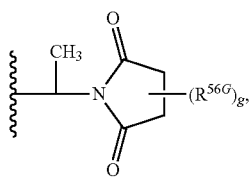

wherein g is 0, 1, 2, 3, or 4; and each instance of $R^{56G}$ is independently selected from the group consisting of halogen, —CN, —NO$_2$, —N$_3$, optionally substituted alkyl, optionally substituted alkenyl, optionally substituted alkynyl, optionally substituted carbocyclyl, optionally substituted phenyl, optionally substituted heterocyclyl, optionally substituted heteroaryl, optionally substituted alkoxy, or an optionally substituted amino group, or optionally two $R^{56G}$ are taken together with the intervening atoms to form optionally substituted aryl, heteroaryl, carbocyclyl, or heterocyclyl. In certain embodiments, R$_1$ is of the formula:

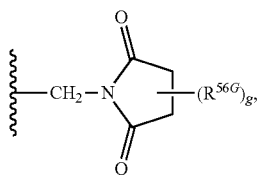

wherein g is 0, 1, 2, 3, or 4; and each instance of $R^{56G}$ is independently halogen, —CN, —NO$_2$, —N$_3$, optionally substituted alkyl, optionally substituted alkenyl, optionally substituted alkynyl, optionally substituted carbocyclyl, optionally substituted phenyl, optionally substituted heterocyclyl, optionally substituted heteroaryl, optionally substituted alkoxy, or an optionally substituted amino group, or two $R^{56G}$ are taken together with the intervening atoms to form optionally substituted aryl, heteroaryl, carbocyclyl, or heterocyclyl. In certain embodiments, g is 0. In certain embodiments, g is 1. In certain embodiments, g is 2. In certain embodiments, g is 3. In certain embodiments, g is 4. In certain embodiments, R$_1$ is of the formula:

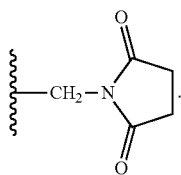

In certain embodiments, R$_1$ is of the formula:

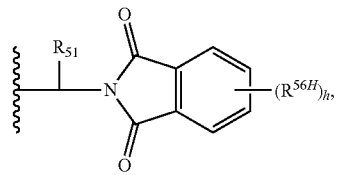

wherein $R_{51}$ is hydrogen, optionally substituted C$_{1-6}$ alkyl, optionally substituted C$_{3-6}$ alkenyl, optionally substituted C$_{3-6}$ alkynyl, optionally substituted C$_{3-6}$ carbocyclyl, optionally substituted 3- to 6-membered heterocyclyl, optionally substituted aryl, optionally substituted heteroaryl; h is 0, 1, 2, 3, or 4; and each instance of $R^{56H}$ is independently halogen, —CN, —NO$_2$, —N$_3$, optionally substituted alkyl, optionally substituted alkenyl, optionally substituted alkynyl, optionally substituted carbocyclyl, optionally substituted phenyl, optionally substituted heterocyclyl, optionally substituted heteroaryl, optionally substituted alkoxy, an optionally substituted amino group, or an optionally substituted acyl group. In certain embodiments, R$_1$ is of the formula:

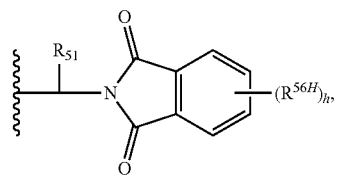

wherein $R_{51}$ is hydrogen, optionally substituted C$_{1-6}$ alkyl, optionally substituted C$_{3-6}$ alkenyl, optionally substituted C$_{3-6}$ alkynyl, optionally substituted C$_{3-6}$ carbocyclyl, optionally substituted 3- to 6-membered heterocyclyl, optionally substituted aryl, or optionally substituted heteroaryl; h is 0, 1, 2, 3, or 4; and each instance of $R^{56H}$ is independently halogen, —CN, —NO$_2$, —N$_3$, optionally substituted alkyl, optionally substituted alkenyl, optionally substituted alkynyl, optionally substituted carbocyclyl, optionally substituted phenyl, optionally substituted heterocyclyl, optionally substituted heteroaryl, optionally substituted alkoxy, an optionally substituted amino group, or an optionally substituted acyl group. In certain embodiments, R$_1$ is of the formula:

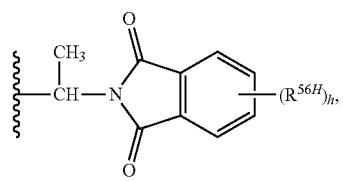

wherein h is 0, 1, 2, 3, or 4; and each instance of $R^{56H}$ is independently halogen, —CN, —NO$_2$, —N$_3$, optionally substituted alkyl, optionally substituted alkenyl, optionally substituted alkynyl, optionally substituted carbocyclyl, optionally substituted phenyl, optionally substituted heterocyclyl, optionally substituted heteroaryl, optionally substituted alkoxy, an optionally substituted amino group, or an optionally substituted acyl group. In certain embodiments, R$_1$ is of the formula:

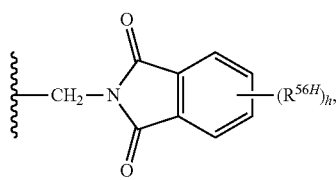

wherein h is 0, 1, 2, 3, or 4; and each instance of $R^{56H}$ is independently halogen, —CN, —NO$_2$, —N$_3$, optionally substituted alkyl, optionally substituted alkenyl, optionally substituted alkynyl, optionally substituted carbocyclyl, optionally substituted phenyl, optionally substituted heterocyclyl, optionally substituted heteroaryl, optionally substituted alkoxy, an optionally substituted amino group, or an optionally substituted acyl group. In certain embodiments, $R_1$ is of the formula:

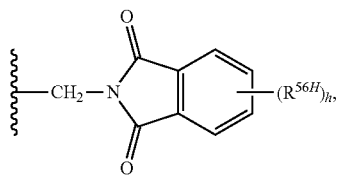

wherein h is 0, 1, 2, 3, or 4; each instance of $R^{56H}$ is independently halogen, —CN, —NO$_2$, —N$_3$, optionally substituted alkyl, optionally substituted alkoxy, an optionally substituted amino group, or an optionally substituted acyl group. In certain embodiments, h is 0. In certain embodiments, h is 1. In certain embodiments, h is 2. In certain embodiments, h is 3. In certain embodiments, h is 4. In certain embodiments, $R_1$ is of the formula:

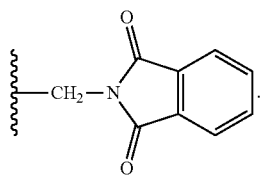 [SMILES: *CN1C(=O)c2ccccc2C1=O]

In certain embodiments, $R_1$ is one of the following formulae: —(C═O)CH$_3$, —CH$_2$—O—(C═O)C$_2$H$_5$, —(C═O)C$_2$H$_5$, —CH$_2$—O—(C═O)—(CH$_2$)$_3$CH$_3$, —(C═O)—(CH$_2$)$_3$CH$_3$, —CH$_2$—O—(C═O)-tC$_4$H$_9$, —(C═O)-tC$_4$H$_9$, —CH$_2$—O—(C═O)—(CH$_2$)$_4$CH$_3$, —(C═O)—(CH$_2$)$_4$CH$_3$, —CH(CH$_3$)—O—(C═O)-tC$_4$H$_9$, —CH$_2$—O—(C═O)O—(CH$_2$)$_2$CH$_3$, —(C═O)O(CH$_2$)$_2$CH$_3$, —CH$_2$—O—(C═O)C$_6$H$_4$OCH$_3$, —(C═O)C$_6$H$_4$OCH$_3$, —CH$_2$—N-Phth, —CH$_2$—N-Suc, wherein N-Suc is

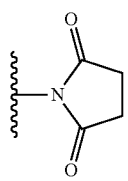

and N-Phth is

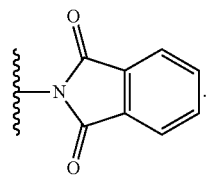 [SMILES: *N1C(=O)c2ccccc2C1=O]

In certain embodiments when the provided compounds are of Formula (I), (II), or (III), $R_2$ is of the formula:

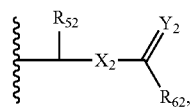

wherein $X_2$ is O or NR$^{XN}$; $Y_2$ is O or NR$^{YN}$; $R^{YN}$ is hydrogen or optionally substituted alkyl; $R_{52}$ is optionally substituted C$_{1-6}$ alkyl, optionally substituted C$_{3-6}$ alkenyl, optionally substituted C$_{3-6}$ alkynyl, optionally substituted C$_{3-6}$ carbocyclyl, optionally substituted 3- to 6-membered heterocyclyl, optionally substituted aryl, or optionally substituted heteroaryl; and $R_{62}$ is optionally substituted C$_{1-6}$ alkyl, optionally substituted C$_{3-6}$ alkenyl, optionally substituted C$_{3-6}$ alkynyl, optionally substituted C$_{3-6}$ carbocyclyl, optionally substituted 3- to 6-membered heterocyclyl, optionally substituted aryl, optionally substituted heteroaryl, —OR$^{56O}$, or —N(R$^{56N}$)$_2$. In certain embodiments, $R_2$ is of the formula:

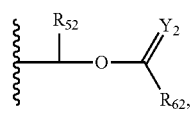

wherein $Y_2$ is O or NR$^{YN}$; $R^{YN}$ is hydrogen or optionally substituted alkyl; $R_{52}$ is hydrogen, optionally substituted alkyl, optionally substituted heterocyclyl, optionally substituted aryl, or optionally substituted heteroaryl; and $R_{62}$ is optionally substituted alkyl, optionally substituted heterocyclyl, optionally substituted aryl, optionally substituted heteroaryl, or optionally substituted alkoxy. In certain embodiments, $R_2$ is of the formula:

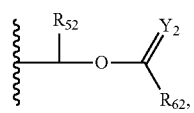

wherein $Y_2$ is O; $R_{52}$ is hydrogen, optionally substituted C$_{1-6}$ alkyl; and $R_{62}$ is optionally substituted C$_{1-6}$ alkyl, optionally substituted aryl, or —OR$^{56O}$. In certain embodiments, $R_2$ is of the formula:

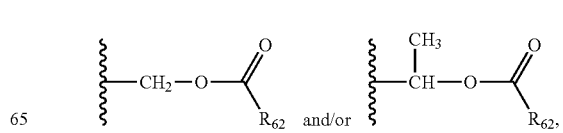

wherein $R_{62}$ is optionally substituted $C_{1-6}$ alkyl, optionally substituted heterocyclyl, optionally substituted aryl, optionally substituted 3- to 6-membered heteroaryl, or $-OR^{56O}$. In certain embodiments, $R_2$ is of the formula:

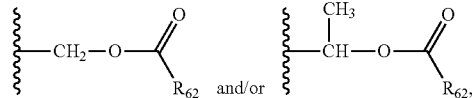

wherein $R_{62}$ is optionally substituted $C_{1-6}$ alkyl, optionally substituted heterocyclyl, optionally substituted aryl, optionally substituted 3- to 6-membered heteroaryl, or $-OR^{56O}$. In certain embodiments, $R_2$ is of the formula:

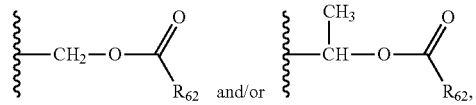

wherein $R_{62}$ is optionally substituted $C_{1-6}$ alkyl. In certain embodiments, $R_2$ is of the formula:

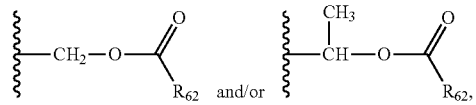

wherein $R_{62}$ is methyl, ethyl, n-propyl, i-propyl, n-butyl, s-butyl, t-butyl, n-pentyl, t-pentyl, neo-pentyl, i-pentyl, s-pentyl, or 3-pentyl. In certain embodiments, $R_2$ is of the formula:

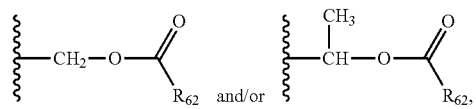

wherein $R_{62}$ is optionally substituted aryl. In certain embodiments, $R_2$ is of the formula:

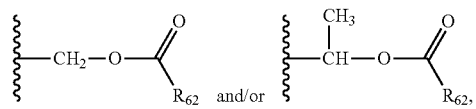

wherein $R_{62}$ is substituted phenyl of the formula:

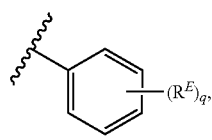

wherein $R^E$ and q are as defined herein. In certain embodiments, $R_2$ is of the formula:

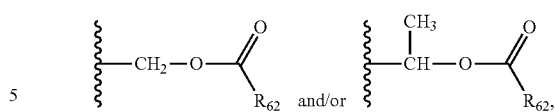

wherein $R_{62}$ is optionally substituted $C_{1-6}$ alkyl, optionally substituted heterocyclyl, optionally substituted aryl, optionally substituted 3- to 6-membered heteroaryl, or $-OR^{56O}$. In certain embodiments, $R_2$ is of the formula:

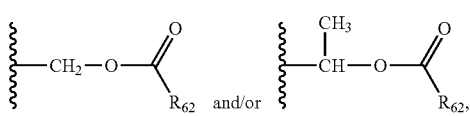

wherein $R_{62}$ is optionally substituted $C_{1-6}$ alkyl. In certain embodiments, $R_2$ is of the formula:

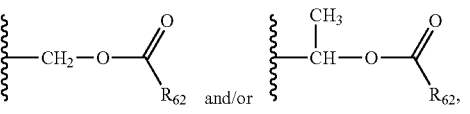

wherein $R_{62}$ is methyl, ethyl, n-propyl, i-propyl, n-butyl, s-butyl, t-butyl, n-pentyl, t-pentyl, neo-pentyl, i-pentyl, s-pentyl, or 3-pentyl. In certain embodiments, $R_2$ is of the formula:

wherein $R_{62}$ is optionally substituted aryl. In certain embodiments, $R_2$ is of the formula:

wherein $R_{62}$ is selected from one of the following formulae

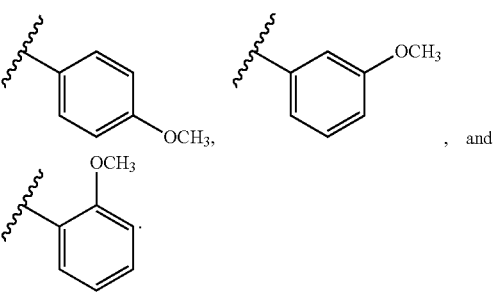

In certain embodiments, $R_2$ is of the formula:

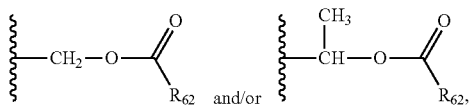

wherein $R_{62}$ is $-OR^{56O}$. In certain embodiments, $R_1$ is of the formula:

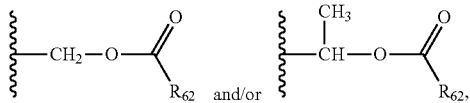

wherein $R_{62}$ is methoxy, ethoxy, n-propyloxy, or 2-propyloxy. In certain embodiments, $R_1$ is of the formula:

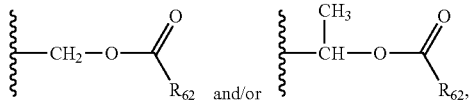

wherein $R_{62}$ is $-O(CH_2CH_2O)_sCH_3$, wherein s is 1, 2, 3, or 4. In certain embodiments, $R_1$ is of the formula:

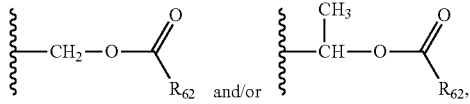

wherein $R_{62}$ is $-O-CH_2CH_2O-CH_3$, $-O(CH_2CH_2O)_2CH_3$, $-O(CH_2CH_2O)_3CH_3$, or $-O(CH_2CH_2O)_4CH_3$.

In certain embodiments when the provided compounds are of Formula (I), (II), or (III), $R_2$ is of Formula (D):

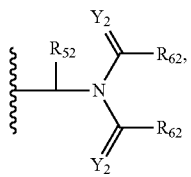

(D)

wherein two $R_{62}$ are taken together with their intervening atoms to form an optionally substituted heterocyclic ring. In certain embodiments, $R_2$ is of the formula:

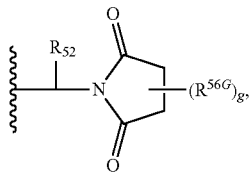

wherein $R_{52}$ is hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, or optionally substituted heteroaryl; g is 0, 1, 2, 3, or 4; and each instance of $R^{56G}$ is independently halogen, $-CN$, $-NO_2$, $-N_3$, optionally substituted alkyl, optionally substituted alkenyl, optionally substituted alkynyl, optionally substituted carbocyclyl, optionally substituted phenyl, optionally substituted heterocyclyl, optionally substituted heteroaryl, optionally substituted alkoxy, or an optionally substituted amino group, or optionally two $R^{56G}$ are taken together with the intervening atoms to form optionally substituted aryl, heteroaryl, carbocyclyl, or heterocyclyl. In certain embodiments, $R_2$ is of the formula:

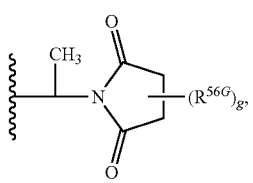

wherein g is 0, 1, 2, 3, or 4; and each instance of $R^{56G}$ is independently halogen, $-CN$, $-NO_2$, $-N_3$, optionally substituted alkyl, optionally substituted alkenyl, optionally substituted alkynyl, optionally substituted carbocyclyl, optionally substituted phenyl, optionally substituted heterocyclyl, optionally substituted heteroaryl, optionally substituted alkoxy, or an optionally substituted amino group, or optionally two $R^{56G}$ are taken together with the intervening atoms to form optionally substituted aryl, heteroaryl, carbocyclyl, or heterocyclyl. In certain embodiments, $R_2$ is of the formula:

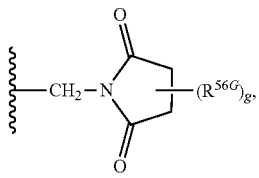

wherein g is 0, 1, 2, 3, or 4; and each instance of $R^{56G}$ is independently halogen, $-CN$, $-NO_2$, $-N_3$, optionally substituted alkyl, optionally substituted alkenyl, optionally substituted alkynyl, optionally substituted carbocyclyl, optionally substituted phenyl, optionally substituted heterocyclyl, optionally substituted heteroaryl, optionally substituted alkoxy, or an optionally substituted amino group, or optionally two $R^{56G}$ are taken together with the intervening atoms to form optionally substituted aryl, heteroaryl, carbocyclyl, or heterocyclyl. In certain embodiments, g is 0. In certain embodiments, g is 1. In certain embodiments, g is 2. In certain embodiments, g is 3. In certain embodiments, g is 4. In certain embodiments, $R_2$ is of the formula:

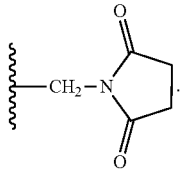 [SMILES: *CN1C(=O)CCC1=O]

In certain embodiments when the provided compounds are of Formula (I), (II), or (III), R₂ is of the formula:

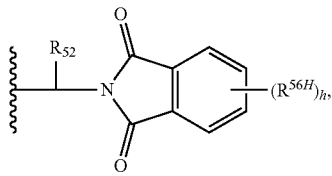

wherein $R_{52}$ is hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, optionally substituted heteroaryl; h is 0, 1, 2, 3, or 4; and each instance of $R^{56H}$ is independently halogen, —CN, —NO₂, —N₃, optionally substituted alkyl, optionally substituted alkenyl, optionally substituted alkynyl, optionally substituted carbocyclyl, optionally substituted phenyl, optionally substituted heterocyclyl, optionally substituted heteroaryl, optionally substituted alkoxy, an optionally substituted amino group, or an optionally substituted acyl group. In certain embodiments, R₂ is of the formula:

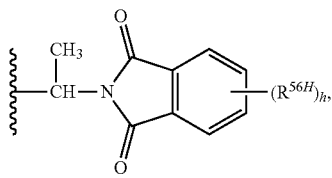

wherein h is 0, 1, 2, 3, or 4; and each instance of $R^{56H}$ is independently halogen, —CN, —NO₂, —N₃, optionally substituted alkyl, optionally substituted alkenyl, optionally substituted alkynyl, optionally substituted carbocyclyl, optionally substituted phenyl, optionally substituted heterocyclyl, optionally substituted heteroaryl, optionally substituted alkoxy, an optionally substituted amino group, or an optionally substituted acyl group. In certain embodiments, R₂ is of the formula:

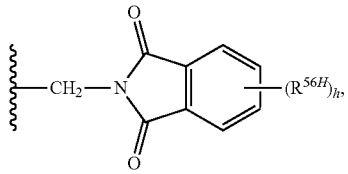

wherein h is 0, 1, 2, 3, or 4; and each instance of $R^{56H}$ is independently halogen, —CN, —NO₂, —N₃, optionally substituted alkyl, optionally substituted alkenyl, optionally substituted alkynyl, optionally substituted carbocyclyl, optionally substituted phenyl, optionally substituted heterocyclyl, optionally substituted heteroaryl, optionally substituted alkoxy, an optionally substituted amino group, or an optionally substituted acyl group. In certain embodiments, R₂ is of the formula:

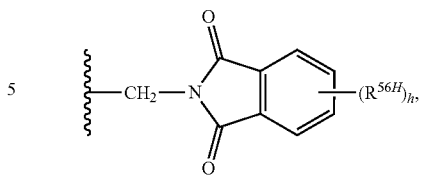

wherein h is 0, 1, 2, 3, or 4; each instance of $R^{56H}$ is independently halogen, —CN, —NO₂, —N₃, or optionally substituted alkyl, optionally substituted alkoxy, an optionally substituted amino group, or an optionally substituted acyl group. In certain embodiments, h is 0. In certain embodiments, h is 1. In certain embodiments, h is 2. In certain embodiments, h is 3. In certain embodiments, h is 4. In certain embodiments, R₂ is of the formula:

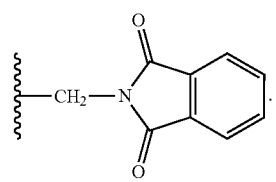 [SMILES: *CN1C(=O)c2ccccc2C1=O]

In certain embodiments, R₂ is one of the following formulae: —CH₂—O—(C=O)CH₃, —CH₂—O—(C=O)C₂H₅, —CH₂—O—(C=O)—(CH₂)₃—CH₃, —CH₂—O—(C=O)-t C₄H₉, —CH₂—O—(C=O)—(CH₂)₄—CH₃, —CH(CH₃)—O—(C=O)-t C₄H₉, —CH(CH₃)—O—(C=O)CH₃, —CH₂—O—(C=O)O—(CH₂)₂—CH₃, —CH₂—O—(C=O)C₆H₄OCH₃, —CH₂—N-Phth, and —CH₂—N-Suc, wherein N-Suc is

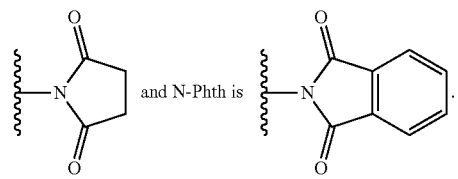 [SMILES: *N1C(=O)CCC1=O ; *N1C(=O)c2ccccc2C1=O]

In certain embodiments, $R_{61}$ and the carbon substituted by $R_{51}$ are taken together with the intervening atoms to form an optionally substituted heterocyclic ring, and R₁ is one of the following formulae:

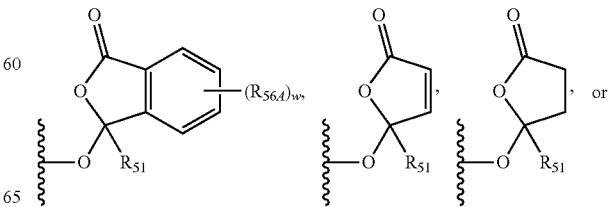

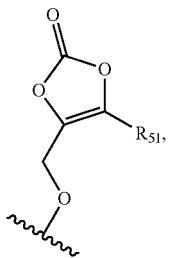

wherein each instance of $R_{56A}$ is independently halogen, —CN, —NO$_2$, —N$_3$, or optionally substituted alkyl, optionally substituted alkoxy, an optionally substituted amino group, or an optionally substituted acyl group; and w is 0, 1, 2, 3, or 4.

In certain embodiments, $R_{62}$ and the carbon substituted by $R_{52}$ are taken together with the intervening atoms to form an optionally substituted heterocyclic ring, and $R_2$ is one of the following formulae:

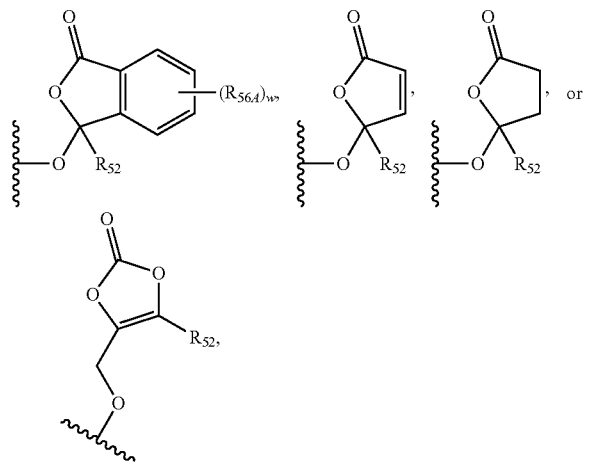

wherein each instance of $R_{56A}$ is independently halogen, —CN, —NO$_2$, —N$_3$, optionally substituted alkyl, optionally substituted alkoxy, an optionally substituted amino group, or an optionally substituted acyl group; and w is 0, 1, 2, 3, or 4.

In certain embodiments, $R_1$ is of the formula:

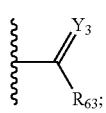

and $R_2$ is one of the following formulae:

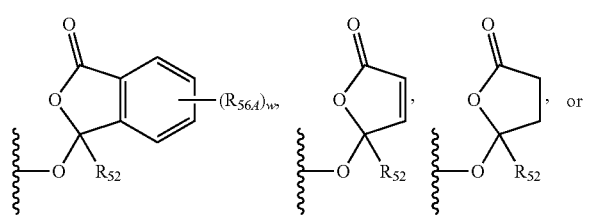

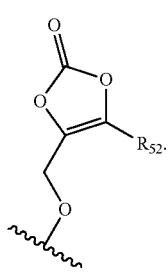

In certain embodiments, $R_1$ is independently of one of the following formulae:

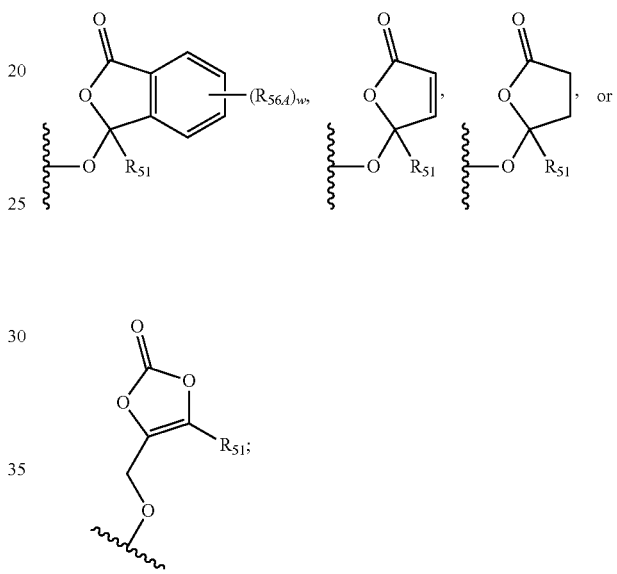

and $R_2$ is independently one of the following formulae:

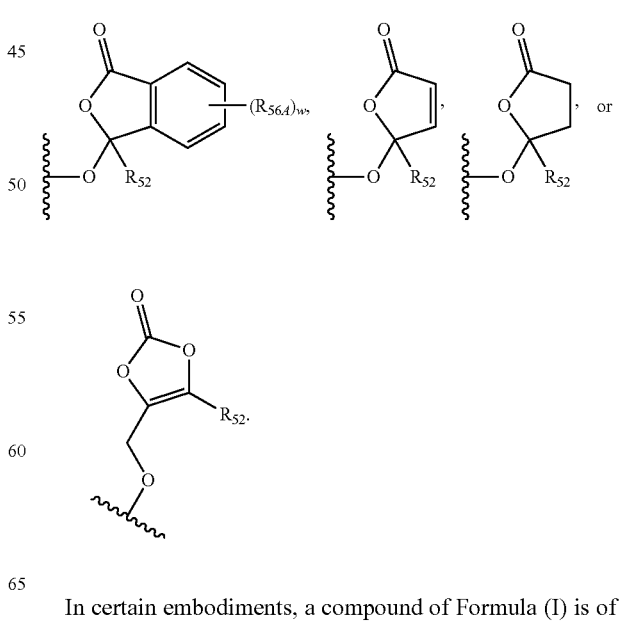

In certain embodiments, a compound of Formula (I) is of Formula (III):

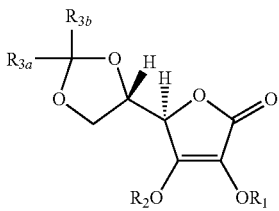

(III)

or a pharmaceutically or cosmetically acceptable salt thereof.

In certain embodiments, a compound of Formula (I) is of Formula (III-a):

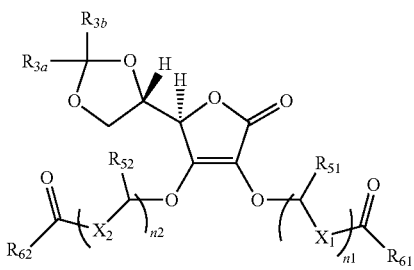

(III-a)

or a pharmaceutically or cosmetically acceptable salt thereof.

In certain embodiments, a compound of Formula (I) is of Formula (III-a1):

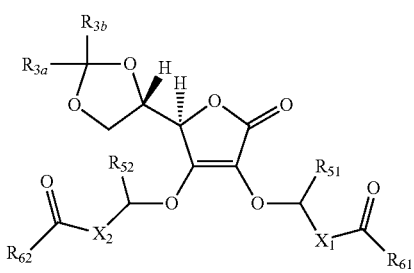

(III-a1)

or a pharmaceutically or cosmetically acceptable salt thereof.

In certain embodiments, a compound of Formula (I) is of Formula (III-a1-i):

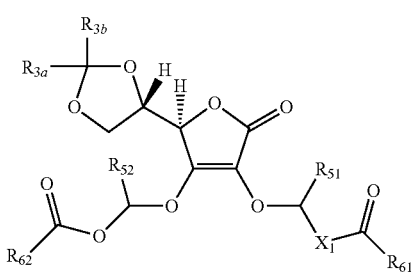

(III-a1-i)

or a pharmaceutically or cosmetically acceptable salt thereof.

In certain embodiments, a compound of Formula (I) is of Formula (III-a1-ii):

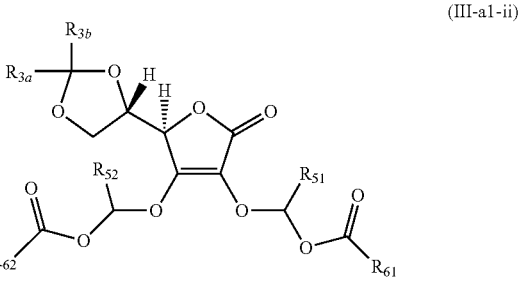

(III-a1-ii)

or a pharmaceutically or cosmetically acceptable salt thereof.

In certain embodiments, a compound of Formula (I) is of Formula (III-a2):

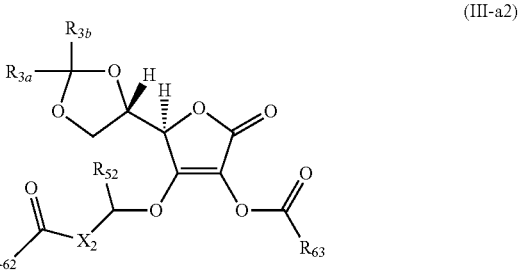

(III-a2)

or a pharmaceutically or cosmetically acceptable salt thereof.

In certain embodiments, a compound of Formula (I) is of Formula (III-a2-i):

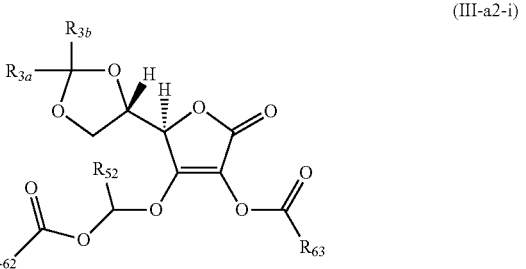

(III-a2-i)

or a pharmaceutically or cosmetically acceptable salt thereof.

In certain embodiments, a compound of Formula (I) is of Formula (III-b):

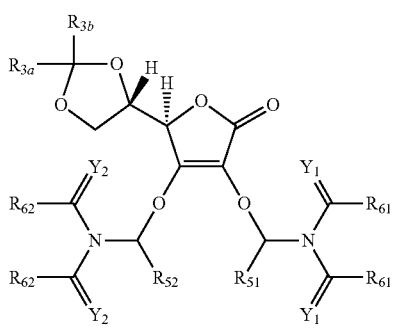

(III-b)

or a pharmaceutically or cosmetically acceptable salt thereof.

In certain embodiments, a compound of Formula (I) is of Formula (IIII-b1):

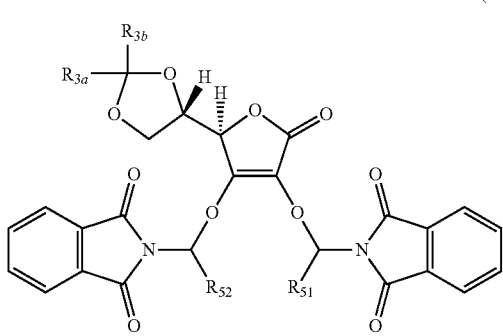

(III-b1)

or a pharmaceutically or cosmetically acceptable salt thereof.

In certain embodiments, a compound of Formula (I) is of Formula (III-b2):

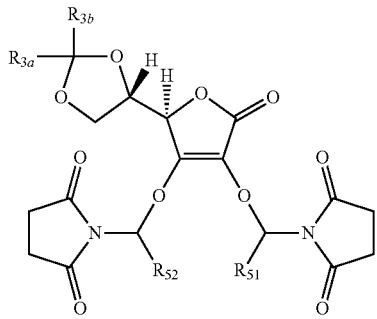

(III-b2)

or a pharmaceutically or cosmetically acceptable salt thereof.

Synthetic Methods

In some embodiments, compounds described herein can be prepared using methods shown in Scheme 1, which include alkylating the free 2,3-enediol with a soft alkylating agent in the presence of one equivalent of organic or inorganic base to give a 3-monoalkylated product.

Scheme 1

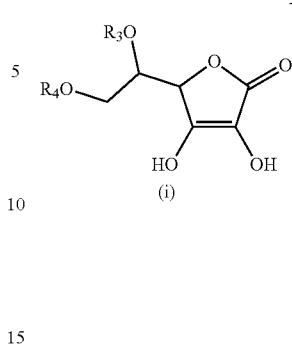

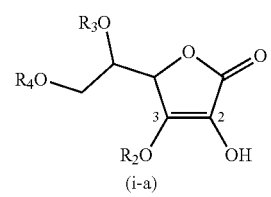

(i-a)

In some embodiments, compounds described herein can be prepared using methods shown in Scheme 2, which include alkylating the free 2,3-enediol with a soft alkylating agent in the presence of two equivalent or organic or inorganic base to give a dialkylated product with both 2- and 3-positions alkylated.

Scheme 2

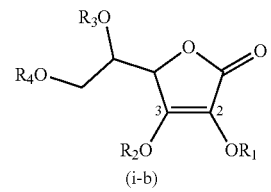

(i-b)

In certain embodiments, the alkylating agent is of Formula (ii), (iii), or (iv):

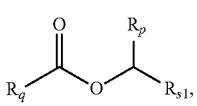

(ii)

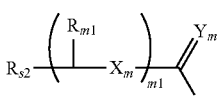

(iii)

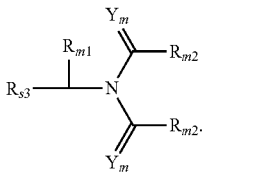

(iv)

In some embodiments, due to the different pKa values of C2—OH and C3—OH (and hence different nucleophilicities) of Formula (i), two products can be formed from reacting a compound of Formula (i) and a compound of Formula (ii): one product is from soft alkylation at both the 2- and 3-ol groups (2,3-diSA), while the other is from soft alkylation at the C3—OH and acylation at the C2—OH group (2-Ac-3-SA). The two products can be separated by column chromatography.

In certain embodiments, the alkylating agent is of Formula (ii):

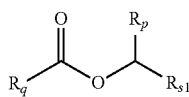

(ii)

wherein:

$R_q$ is optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, —$OR^{qO}$, or —$N(R^{qN})_2$;

each instance of $R^{qO}$ is independently optionally substituted $C_{1-6}$ alkyl, optionally subsubstituted heteroalkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, optionally substituted heteroaryl, or an oxygen protecting group;

each instance of $R^{qN}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, or a nitrogen protecting group; and $R_p$ is hydrogen or optionally substituted $C_{1-6}$ alkyl; and $R_{s1}$ is a suitable leaving group.

As generally defined herein, $R_q$ is optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, —$OR^{qO}$, or —$N(R^{qN})_2$. In certain embodiments, $R_q$ is optionally substituted $C_{1-6}$ alkyl. In certain embodiments, $R_q$ is substituted $C_{1-6}$ alkyl. In certain embodiments, $R_q$ is unsubstituted $C_{1-6}$ alkyl. In certain embodiments, $R_q$ is methyl, ethyl, n-propyl, i-propyl, n-butyl, s-butyl, t-butyl, n-pentyl, t-pentyl, neo-pentyl, i-pentyl, s-pentyl, or 3-pentyl. In certain embodiments, $R_q$ is optionally substituted $C_{3-6}$ alkenyl. In certain embodiments, $R_q$ is optionally substituted $C_{3-6}$ alkynyl. In certain embodiments, $R_q$ is optionally substituted $C_{3-6}$ carbocyclyl. In certain embodiments, $R_q$ is optionally substituted aryl. In certain embodiments, $R_q$ is optionally substituted 3- to 6-membered heterocyclyl. In certain embodiments, $R_q$ is optionally substituted heteroaryl. In certain embodiments, $R_q$ is —$OR^{qO}$. In certain embodiments, $R^q$ is —$O(CH_2CH_2O)_sCH_3$, wherein s is 1, 2, 3, or 4. In certain embodiments, $R^q$ is —$OCH_2CH_2OCH_3$, —$O(CH_2CH_2O)_2CH_3$, —$O(CH_2CH_2O)_3CH_3$, or —$(CH_2CH_2O)_4CH_3$. In certain embodiments, $R_q$ is —$N(R^{qN})_2$.

As generally defined herein, each instance of $R^{qO}$ is independently optionally substituted $C_{1-6}$ alkyl, optionally subsubstituted heteroalkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, optionally substituted heteroaryl, or an oxygen protecting group. In certain embodiments, $R^{qO}$ is optionally substituted $C_{1-6}$ alkyl. In certain embodiments, $R^{qO}$ is methyl, ethyl, n-propyl, or iso-propyl. In certain embodiments, $R^{qO}$ is optionally subsubstituted heteroalkyl. In certain embodiments, $R^{qO}$ is $(CH_2CH_2O)_sCH_3$, wherein s is 1, 2, 3, or 4. In certain embodiments, $R^{qO}$ is —$CH_2CH_2OCH_3$, —$(CH_2CH_2O)_2CH_3$, —$(CH_2CH_2O)_3CH_3$, or —$(CH_2CH_2O)_4CH_3$. In certain embodiments, $R^{qO}$ is optionally substituted $C_{3-6}$ alkenyl. In certain embodiments, $R^{qO}$ is optionally substituted $C_{3-6}$ alkynyl. In certain embodiments, $R^{qO}$ is optionally substituted $C_{3-6}$ carbocyclyl. In certain embodiments, $R^{qO}$ is optionally substituted aryl. In certain embodiments, $R^{qO}$ is optionally substituted 3- to 6-membered heterocyclyl. In certain embodiments, $R^{qO}$ is optionally substituted heteroaryl. In certain embodiments, $R^{qO}$ is an oxygen protecting group. In certain embodiments, $R^{qO}$ is Ac, Boc, TBS, TIPS, Bn, or Bz.

As generally defined herein, each instance of $R^{qN}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, or a nitrogen protecting group. In certain embodiments, $R^{qN}$ is optionally substituted $C_{1-6}$ alkyl. In certain embodiments, $R^{qN}$ is methyl, ethyl, n-propyl, or iso-propyl. In certain embodiments, $R^{qN}$ is optionally substituted $C_{3-6}$ alkenyl. In certain embodiments, $R^{qN}$ is optionally substituted $C_{3-6}$ alkynyl. In certain embodiments, $R^{qN}$ is optionally substituted $C_{3-6}$ carbocyclyl. In certain embodiments, $R^{qN}$ is optionally substituted aryl. In certain embodiments, $R^{qN}$ is optionally substituted 3- to 6-membered heterocyclyl. In certain embodiments, $R^{qN}$ is optionally substituted heteroaryl. In certain embodiments, $R^{qN}$ is an nitrogen protecting group. In certain embodiments, $R^{qN}$ is Bn, BOC, Cbz, Fmoc, trifluoroacetyl, triphenylmethyl, or Ts.

As generally defined herein, $R_p$ is hydrogen or optionally substituted $C_{1-6}$ alkyl. In certain embodiments, $R_p$ is hydrogen. In certain embodiments, $R_p$ is optionally substituted $C_{1-6}$ alkyl. In certain embodiments, $R_p$ is substituted $C_{1-6}$ alkyl. In certain embodiments, $R_p$ is unsubstituted $C_{1-6}$ alkyl. In certain embodiments, $R_p$ is methyl, ethyl, or propyl.

As generally defined herein, $R_{s1}$ is a leaving group, i.e. an atom or a group capable of being displaced by a nucleophile. Examples of suitable leaving groups include, but are not limited to, halogen (such as Cl, Br, or I (iodine)). In some embodiments, $R_{s1}$ is halogen. In some embodiments, $R_{s1}$ is I. In some embodiments, $R_{s1}$ is Br. In some embodiments, $R_{s1}$ is a sulfonic acid ester, such as toluenesulfonate (tosylate, -OTs), methanesulfonate (mesylate, -OMs), p-bromobenzenesulfonate (brosylate, -OBs), or trifluoromethanesulfonate (triflate, -OTf). In some cases, $R_{s1}$ is a brosylate, such as p-bromobenzenesulfonyloxy, a nosylate, such as 2-nitrobenzenesulfonyloxy, or a sulfonate-containing group. In some embodiments, $R_{s1}$ is a tosylate group.

In certain embodiments, the alkylating agent is of Formula (iii):

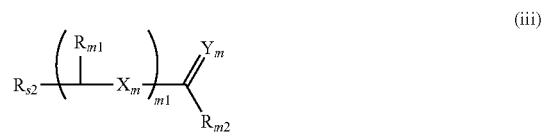

(iii)

wherein:
each instance of $X_m$ is independently —O—, or —NR$^{XN}$—;
$Y_m$ is independently =O or =NR$^{YN}$;
$R_{s2}$ is a suitable leaving group.
each instance of $R_{m1}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, or optionally substituted heteroaryl;
$R_{m2}$ is independently optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, optionally substituted heteroaryl, —OR$^{mO}$, or —N(R$^{mN}$)$_2$, or two $R_{m2}$ are taken together with their intervening atoms to form an optionally substituted heterocyclic ring, or one $R_{m1}$ and one $R_{m2}$ in Formula (iv) are taken together with their intervening atoms to form an optionally substituted heterocyclic ring;
each instance of R$^{mN}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted heterocyclyl, optionally substituted heteroaryl, or a nitrogen protecting group;
each instance of R$^{mO}$ is independently optionally substituted $C_{1-6}$ alkyl, optionally substituted heteroalkyl, optionally substituted $C_{3-6}$ alkenyl, optionally substituted $C_{3-6}$ alkynyl, optionally substituted $C_{3-6}$ carbocyclyl, optionally substituted aryl, optionally substituted heterocyclyl, optionally substituted heteroaryl, or an oxygen protecting group;
each instance of R$^{XN}$ and R$^{YN}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, or a nitrogen protecting group; and
$m_1$ is independently 1, 2, or 3.
In certain embodiments, the alkylating agent is of Formula (iv):

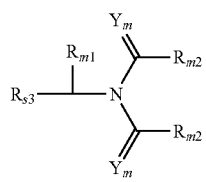

(iv)

wherein:
$Y_m$, $R_{m1}$, $R_{m2}$, R$^{mN}$, and R$^{mO}$ are as define herein; and
$R_{s3}$ is a suitable leaving group.
As generally defined herein, each occurrence of $X_m$ is independently —O—, or —NR$^{XN}$—, wherein R$^{XN}$ is as defined herein. In some embodiments, each occurrence of $X_m$ is independently —O—. In some embodiments, each occurrence of $X_m$ is —NR$^{XN}$—, wherein R$^{XN}$ is as defined herein. In some embodiments, each occurrence of $X_m$ is —NR$^{XN}$—, wherein R$^{XN}$ is hydrogen, optionally substituted $C_{1-6}$ alkyl, or a nitrogen protecting group. In some embodiments, $X_m$ is —NH—.
As generally defined herein, each occurrence of $Y_m$ is independently =O, or =NR$^{XN}$, wherein R$^{XN}$ is as defined herein. In some embodiments, each occurrence of $Y_m$ is independently =O. In some embodiments, each occurrence of $Y_m$ is NR$^{XN}$, wherein R$^{XN}$ is as defined herein. In some embodiments, each occurrence of $Y_m$ is NR$^{XN}$, wherein R$^{XN}$ is hydrogen, optionally substituted $C_{1-6}$ alkyl, or a nitrogen protecting group. In some embodiments, each occurrence of $Y_m$ is NH.

As generally described above, each instance of $R_{m1}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, or optionally substituted heteroaryl. In certain embodiments, $R_{m1}$ is hydrogen. In certain embodiments, $R_{m1}$ is optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, or optionally substituted heteroaryl. In certain embodiments, $R_{m1}$ is optionally substituted $C_{1-6}$ alkyl. In certain embodiments, $R_{m1}$ is substituted $C_{1-6}$ alkyl. In certain embodiments, $R_{m1}$ is unsubstituted $C_{1-6}$ alkyl. In certain embodiments, $R_{m1}$ is methyl, ethyl, or propyl. In certain embodiments, $R_{m1}$ is methyl. In some embodiments, $R_{m1}$ is optionally substituted $C_{3-6}$ alkenyl. In some embodiments, $R_{m1}$ is optionally substituted $C_{3-6}$ alkynyl. In some embodiments, $R_{m1}$ is optionally substituted $C_{3-6}$ carbocyclyl, optionally substituted 3- to 6-membered heterocyclyl, optionally substituted aryl, or optionally substituted heteroaryl. In some embodiments, $R_{m1}$ is optionally substituted $C_{3-6}$ carbocyclyl. In some embodiments, $R_{m1}$ is optionally substituted 3- to 6-membered heterocyclyl. In some embodiments, $R_{m1}$ is optionally substituted 6-membered heterocyclyl with one heteroatom selected from the group consisting of N, O, and S. In some embodiments, $R_{m1}$ is optionally substituted 5-membered heterocyclyl with one heteroatom selected from the group consisting of N, O, and S. In some embodiments, $R_{m1}$ is optionally substituted aryl. In some embodiments, $R_{m1}$ is optionally substituted phenyl. In some embodiments, $R_{m1}$ is phenyl. In some embodiments, $R_{m1}$ is optionally substituted heteroaryl.

As generally described above, each instance of $R_{m2}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, optionally substituted heteroaryl, —OR$^{mO}$, or —N(R$^{mN}$)$_2$. In certain embodiments, $R_{m2}$ is hydrogen. In certain embodiments, $R_{m2}$ is optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, optionally substituted heteroaryl, —OR$^{mO}$, or —N(R$^{mN}$)$_2$. In certain embodiments, $R_{m2}$ is optionally substituted $C_{1-6}$ alkyl. In certain embodiments, $R_{m2}$ is substituted $C_{1-6}$ alkyl. In certain embodiments, $R_{m2}$ is unsubstituted $C_{1-6}$ alkyl. In certain embodiments, $R_{m2}$ is methyl, ethyl, n-propyl, i-propyl, n-butyl, s-butyl, t-butyl, n-pentyl, t-pentyl, neo-pentyl, i-pentyl, s-pentyl, or 3-pentyl. In some embodiments, $R_{m2}$ is optionally substituted $C_{3-6}$ alkenyl. In some embodiments, $R_{m2}$ is optionally substituted $C_{3-6}$ alkynyl. In some embodiments, $R_{m2}$ is optionally substituted $C_{3-6}$ carbocyclyl, optionally substituted 3- to 6-membered heterocyclyl, optionally substituted aryl, optionally substituted heteroaryl, —OR$^{mO}$, or —N(R$^{mN}$)$_2$. In some embodiments, $R_{m2}$ is optionally substituted $C_{3-6}$ carbocyclyl. In some embodiments, $R_{m2}$ is optionally substituted 3- to 6-membered heterocyclyl. In some embodiments, $R_{m2}$ is optionally substituted aryl. In some embodiments, $R_{m2}$ is phenyl. In some embodiments, $R_{m2}$ is optionally substituted phenyl of the formula

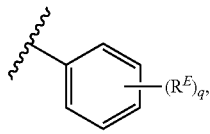

wherein q is 0, 1, 2, 3, 4, or 5; $R^E$ is independently selected from the group consisting of halogen, —CN, —NO$_2$, —N$_3$, optionally substituted alkyl, optionally substituted alkenyl, optionally substituted alkynyl, optionally substituted carbocyclyl, optionally substituted phenyl, optionally substituted heterocyclyl, optionally substituted heteroaryl, optionally substituted alkoxy, an optionally substituted amino group, or an optionally substituted acyl group. In certain embodiments, q is 0. In certain embodiments, q is 1. In certain embodiments, q is 2. In certain embodiments, q is 3. In certain embodiments, q is 4. In certain embodiments, q is 5. In certain embodiments, q is 1 and $R^E$ is optionally substituted alkyl or optionally substituted alkoxy. In certain embodiments, q is 1, and $R_{m2}$ is one of the formulae:

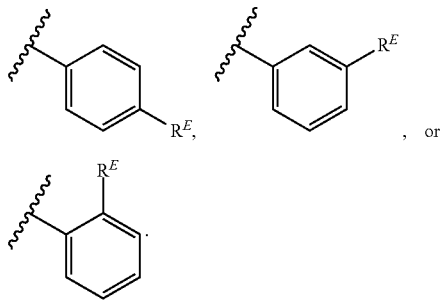

In certain embodiments, q is 2, and $R_{m2}$ is one of the formulae:

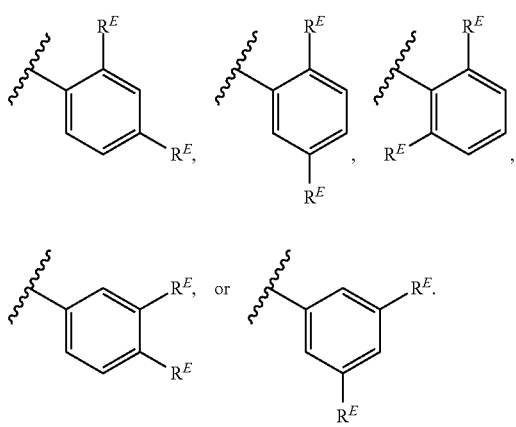

In certain embodiments, q is 3, and $R_{m2}$ is one of the formulae:

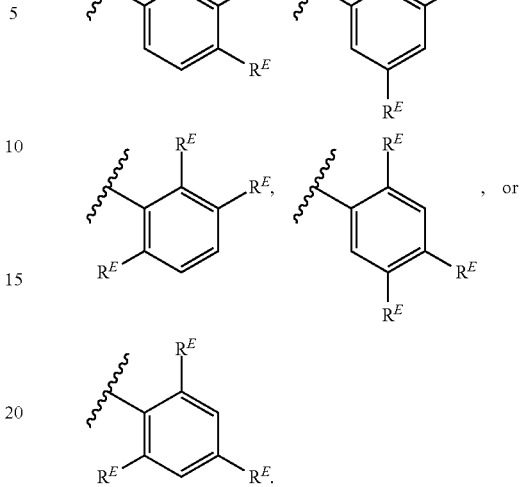

In certain embodiments, q is 4, and $R_{m2}$ is one of the formulae:

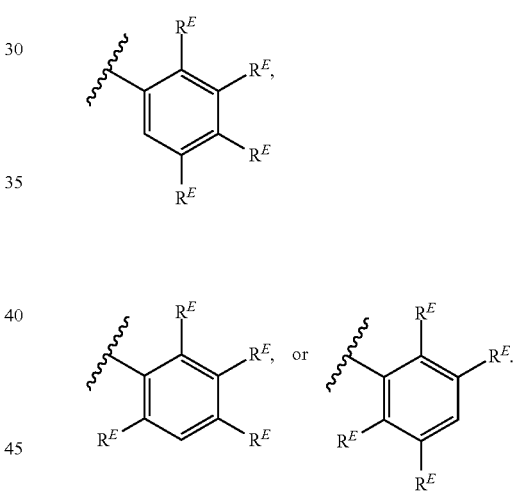

In certain embodiments, q is 5, and $R_{m2}$ is of the formula

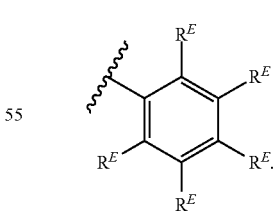

In certain embodiments, $R^E$ is optionally substituted alkyl. In certain embodiments, $R^E$ is methyl, ethyl, or propyl. In certain embodiments, $R^E$ is optionally substituted alkoxy. In certain embodiments, $R^E$ is methoxy or ethoxy. In certain embodiments, $R_{m2}$ is one of the following formulae:

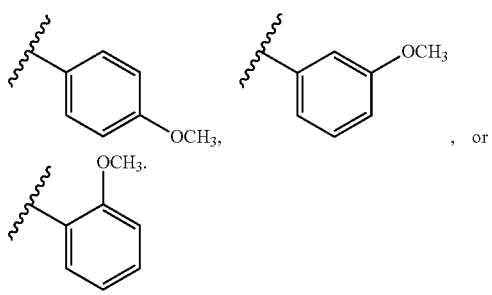

In some embodiments, $R_{m2}$ is optionally substituted heteroaryl. In some embodiments, $R_{m2}$ is optionally substituted 6-membered heteroaryl with one heteroatom selected from the group consisting of N, O, and S. In some embodiments, $R_{m2}$ is optionally substituted 6-membered heteroaryl with two heteroatoms each independently selected from the group consisting of N, O, and S. In some embodiments, $R_{m2}$ is optionally substituted 5-membered heteroaryl with one heteroatom selected from the group consisting of N, O, and S. In some embodiments, $R_{m2}$ is optionally substituted 5-membered heteroaryl with two heteroatoms each independently selected from the group consisting of N, O, and S.

In some embodiments, $R_{m2}$ is —$OR^{mO}$. In some embodiments, $R_{m2}$ is —$OR^{mO}$, wherein $R^{mO}$ is independently optionally substituted $C_{1-6}$ alkyl, optionally substituted $C_{3-6}$ carbocyclyl, optionally substituted aryl, optionally substituted heterocyclyl, optionally substituted heteroaryl, or an oxygen protecting group. In certain embodiments, $R_{m2}$ is —$OR^{mO}$, wherein $R^{mO}$ is optionally substituted $C_{1-6}$ alkyl. In certain embodiments, $R_{m2}$ is —$OR^{mO}$, wherein $R^{mO}$ is unsubstituted $C_{1-6}$ alkyl. In certain embodiments, $R_{m2}$ is —O-methyl, —O-ethyl, —O-propyl, —O-isopropyl, —O-isobutyl, or —O-isoamyl. In certain embodiments, $R_{m2}$ is —$OR^{mO}$, wherein $R^{mO}$ is optionally substituted heteroalkyl. In certain embodiments, $R_{m2}$ is —$O(CH_2CH_2O)_sCH_3$, wherein s is 1, 2, 3, or 4. In certain embodiments, $R_{m2}$ is —O—$CH_2CH_2O$—$CH_3$. In certain embodiments, $R_{m2}$ is —$O(CH_2CH_2O)_2CH_3$. In certain embodiments, $R_{m2}$ is —$O(CH_2CH_2O)_3CH_3$. In certain embodiments, $R_{m2}$ is —$O(CH_2CH_2O)_4CH_3$. In certain embodiments, $R_{m2}$ is —$OR^{mO}$, wherein $R^{mO}$ is optionally substituted $C_{3-6}$ alkenyl. In certain embodiments, $R_{m2}$ is —$OR^{mO}$, wherein $R^{mO}$ is optionally substituted $C_{3-6}$ alkynyl. In certain embodiments, $R_{m2}$ is —$OR^{mO}$, wherein $R^{mO}$ is optionally substituted 3- to 6-membered heterocyclyl. In certain embodiments, $R_{m2}$ is —$OR^{mO}$, wherein $R^{mO}$ is optionally substituted aryl. In certain embodiments, $R_{m2}$ is —O-phenyl. In certain embodiments, $R_{m2}$ is —$OR^{mO}$, wherein $R^{mO}$ is optionally substituted heteroaryl. In certain embodiments, $R_{m2}$ is —$OR^{mO}$, wherein $R^{mO}$ is an oxygen protecting group. In certain embodiments, $R_{m2}$ is —$OR^{mO}$, wherein $R^{mO}$ is Ac, Boc, TBS, TIPS, Bn, or Bz.

In some embodiments, $R_{m2}$ is —$N(R^{mN})_2$. In certain embodiments, $R_{m2}$ is —$NHR^{mN}$, wherein $R^{mN}$ is optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, or a nitrogen protecting group. In certain embodiments, $R_{m2}$ is —$NHR^{mN}$, wherein $R^{mN}$ is unsubstituted $C_{1-6}$ alkyl. In certain embodiments, $R_{m2}$ is —NH-methyl, —NH-ethyl, or —NH-propyl. In certain embodiments, $R_{m2}$ is —$NHR^{mN}$, wherein $R^{mN}$ is substituted $C_{1-6}$ alkyl. In certain embodiments, $R_{m2}$ is —NH-benzyl. In certain embodiments, $R_{m2}$ is —$N(R^{mN})_2$, wherein $R^{mN}$ is optionally substituted $C_{1-6}$ alkyl, optionally substituted $C_{3-6}$alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, or a nitrogen protecting group. In certain embodiments, $R_{m2}$ is —$N(R^{mN})_2$, wherein each instance of $R^{mN}$ is independently optionally substituted $C_{1-6}$ alkyl. In certain embodiments, $R_{m2}$ is —$N(R^{mN})_2$, wherein each $R^{mN}$ is independently unsubstituted $C_{1-6}$ alkyl. In certain embodiments, $R_{m2}$ is —$N(CH_3)R^{mN}$, wherein each $R^{mN}$ is independently optionally substituted $C_{1-6}$ alkyl or or a nitrogen protecting group. In certain embodiments, $R_{m2}$ is —$N(CH_2CH_3)R^{mN}$, wherein each $R^{mN}$ is independently optionally substituted $C_{1-6}$ alkyl or a nitrogen protecting group. In certain embodiments, $R_{m2}$ is —$N(R^{mN})_2$, wherein each instance $R^{mN}$ is independently selected from the group consisting of methyl, ethyl, isopropyl, isobutyl, isoamyl, and benzyl. In some embodiments, $R_{m2}$ is —$N(R^{mN})_2$, wherein each instance of $R^{mN}$ is the same. In some embodiments, $R_{m2}$ is —$N(R^{mN})_2$, wherein each instance of $R^{mN}$ is different. In certain embodiments, $R_{m2}$ is —$NH_2$. In certain embodiments, $R^{mN}$ is a nitrogen protecting group. In certain embodiments, $R^{mN}$ is Bn, BOC, Cbz, Fmoc, trifluoroacetyl, triphenylmethyl, or Ts.

In some embodiments, two $R_{m2}$ are optionally taken together with the intervening atoms to form an optionally substituted heterocyclic ring. In some embodiments, two $R_{m2}$ are taken together with the intervening atoms to form an optionally substituted 5-membered heterocyclic ring. In some embodiments, two $R_{m2}$ are taken together with the intervening atoms to form an optionally substituted 5-membered heterocyclic ring with one heteroatom selected from the group consisting of S, O, and N. In some embodiments, two $R_{m2}$ are taken together with the intervening atoms to form an optionally substituted 5-membered heterocyclic ring with one N. In some embodiments, two $R_{m2}$ are taken together with the intervening atoms to form an optionally substituted 5-membered heterocyclic ring with two heteroatoms each independently selected from the group consisting of S, O, and N. In some embodiments, two $R_{m2}$ are taken together with the intervening atoms to form an optionally substituted 6-membered heterocyclic ring. In some embodiments, two $R_{m2}$ are taken together with the intervening atoms to form an optionally substituted 6-membered heterocyclic ring with one heteroatom selected from the group consisting of S, O, and N. In some embodiments, two $R_{m2}$ are taken together with the intervening atoms to form an optionally substituted 6-membered heterocyclic ring with two heteroatoms each independently selected from the group consisting of S, O, and N. In some embodiments, two $R_{m2}$ are taken together with the intervening atoms to form an optionally substituted bicyclic heterocyclic ring with one heteroatom selected from the group consisting of S, O, and N. In some embodiments, two $R_{m2}$ are taken together with the intervening atoms to form an optionally substituted bicyclic heterocyclic ring with one N. In some embodiments, two $R_{m2}$ are taken together with the intervening atoms to form an optionally substituted heterocyclic ring of the formula

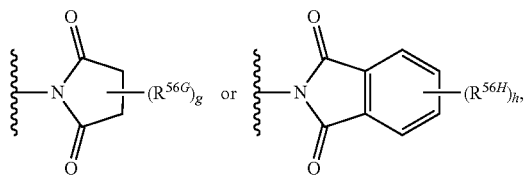

wherein $R^{56G}$, $R^{56H}$, g, and h are as defined herein. In some embodiments, two $R_{m2}$ are taken together with the intervening atoms to form a heterocyclic ring of the formula:

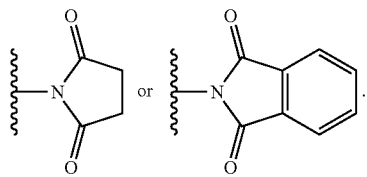

In some embodiments, one $R_{m1}$ and one $R_{m2}$ in Formula (iv) are taken together with their intervening atoms to form an optionally substituted heterocyclic ring.

As generally defined herein, each instance of $R^{mN}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, or a nitrogen protecting group. In certain embodiments, $R^{mN}$ is optionally substituted $C_{1-6}$ alkyl. In certain embodiments, $R^{mN}$ is methyl, ethyl, n-propyl, or iso-propyl. In certain embodiments, $R^{mN}$ is optionally substituted $C_{3-6}$ alkenyl. In certain embodiments, $R^{mN}$ is optionally substituted $C_{3-6}$ alkynyl. In certain embodiments, $R^{mN}$ is optionally substituted $C_{3-6}$ carbocyclyl. In certain embodiments, $R^{mN}$ is optionally substituted aryl. In certain embodiments, $R^{mN}$ is optionally substituted 3- to 6-membered heterocyclyl. In certain embodiments, $R^{mN}$ is optionally substituted heteroaryl. In certain embodiments, $R^{mN}$ is an nitrogen protecting group. In certain embodiments, $R^{mN}$ is Bn, BOC, Cbz, Fmoc, trifluoroacetyl, triphenylmethyl, or Ts.

As generally defined herein, each instance of $R^{mO}$ is independently optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, optionally substituted heteroaryl, or an oxygen protecting group. In certain embodiments, $R^{mO}$ is optionally substituted $C_{1-6}$ alkyl. In certain embodiments, $R^{mO}$ is methyl, ethyl, n-propyl, or iso-propyl.

In certain embodiments, $R^{mO}$ is optionally substituted heteroalkyl. In certain embodiments, $R^{mO}$ is —$(CH_2CH_2O)_s$ $CH_3$, wherein s is 1, 2, 3, or 4. In certain embodiments, $R^{mO}$ is —$CH_2CH_2OCH_3$, —$(CH_2CH_2O)_2CH_3$, —$(CH_2CH_2O)_3 CH_3$, or —$(CH_2CH_2O)_4CH_3$.

In certain embodiments, $R^{mO}$ is optionally substituted $C_{3-6}$ alkenyl. In certain embodiments, $R^{mO}$ is optionally substituted $C_{3-6}$ alkynyl. In certain embodiments, $R^{mO}$ is optionally substituted $C_{3-6}$ carbocyclyl. In certain embodiments, $R^{mO}$ is optionally substituted aryl. In certain embodiments, $R^{mO}$ is optionally substituted 3- to 6-membered heterocyclyl. In certain embodiments, $R^{mO}$ is optionally substituted heteroaryl. In certain embodiments, $R^{mO}$ is an oxygen protecting group. In certain embodiments, $R^{mO}$ is Ac, Boc, TBS, TIPS, Bn, or Bz.

As generally defined herein, $m_1$ is independently 1, 2, or 3. In certain embodiments, m1 is 1. In certain embodiments, m1 is 2. In certain embodiments, m1 is 3.

As generally defined herein, $R_{s2}$ is a leaving group, i.e. an atom or a group capable of being displaced by a nucleophile. Examples of suitable leaving groups include, but are not limited to, halogen (such as Cl, Br, or I). In some embodiments, $R_{s2}$ is halogen. In some embodiments, $R_{s2}$ is I. In some embodiments, $R_{s2}$ is Br. In some embodiments, $R_{s2}$ is a sulfonic acid ester, such as toluenesulfonate (tosylate, -OTs), methanesulfonate (mesylate, -OMs), p-bromobenzenesulfonyloxy (brosylate, -OBs), or trifluoromethanesulfonate (triflate, -OTf). In some cases, $R_{s2}$ is a brosylate, such as p-bromobenzenesulfonyloxy, a nosylate, such as 2-nitrobenzenesulfonyloxy, or a sulfonate-containing group. In some embodiments, $R_{s2}$ is a tosylate group.

As generally defined herein, $R_{s3}$ is a leaving group, i.e. an atom or a group capable of being displaced by a nucleophile. Examples of suitable leaving groups include, but are not limited to, halogen (such as Cl, Br, or I). In some embodiments, $R_{s3}$ is halogen. In some embodiments, $R_{s3}$ is I. In some embodiments, $R_{s3}$ is Br. In some embodiments, $R_{s3}$ is a sulfonic acid ester, such as toluenesulfonate (tosylate, -OTs), methanesulfonate (mesylate, -OMs), p-bromobenzenesulfonyloxy (brosylate, -OBs), or trifluoromethanesulfonate (triflate, -OTf). In some cases, $R_{s3}$ is a brosylate, such as p-bromobenzenesulfonyloxy, a nosylate, such as 2-nitrobenzenesulfonyloxy, or a sulfonate-containing group. In some embodiments, $R_{s3}$ is a tosylate group.

In certain embodiments, compounds described herein can be prepared by reacting a compound of Formula (i):

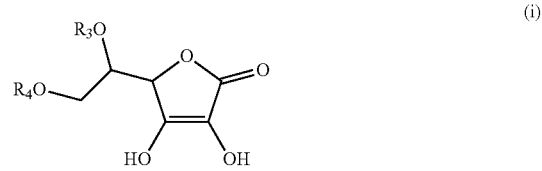

with a compound of Formula (ii):

In some embodiments, compounds described herein can be prepared using a method comprising steps of alkylating a compound of Formula (i):

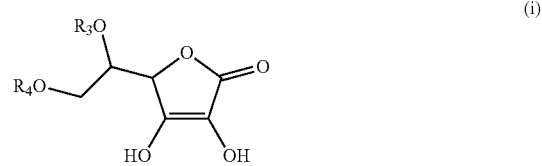

with a soft alkylating agent of Formula (ii), (iii) or Formula (iv)

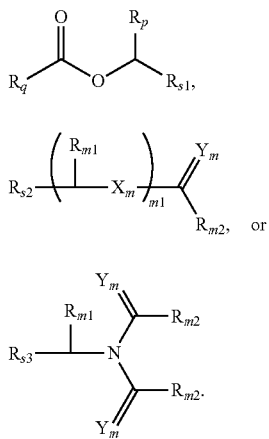

(ii)

(iii)

(iv)

In certain embodiments, the molar ratio of the soft alkylating agent to the compound of Formula (i) is about 1:1 to give a 3-monoalkylated product. In certain embodiments, the molar ratio of the soft alkylating agent to the compound of Formula (i) is about 2:1 to give a 2- and 3-dialkylated product. In certain embodiments, the alkylation reaction is carried out in the presence of an organic base (e.g., Et$_3$N) or inorganic base (e.g., potassium carbonate). In certain embodiments, the molar ratio of the organic or inorganic base to the compound of Formula (i) is about 1:1. In certain embodiments, the molar ratio of the organic or inorganic base to the compound of Formula (i) is about 2:1. In certain embodiments, the molar ratio of the soft alkylating agent to the compound of Formula (i) is about 1:1, and the molar ratio of the organic or inorganic base to the compound of Formula (i) is about 1:1; and the 3-monoalkylated product of Formula (i-a) is formed. In certain embodiments, the molar ratio of the soft alkylating agent to the compound of Formula (i) is about 2:1; the molar ratio of the organic or inorganic base to the compound of Formula (i) is about 2:1; and the 2- and 3-dialkylated product of Formula (i-b) is formed.

In some embodiments, compounds described herein can be prepared using methods shown in Scheme 3, comprising acylating the free 2,3-enediol with an acylating agent, followed by alkylation with a soft alkylating agent.

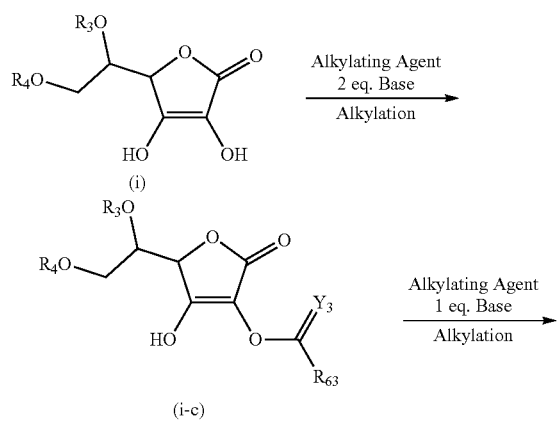

Scheme 3

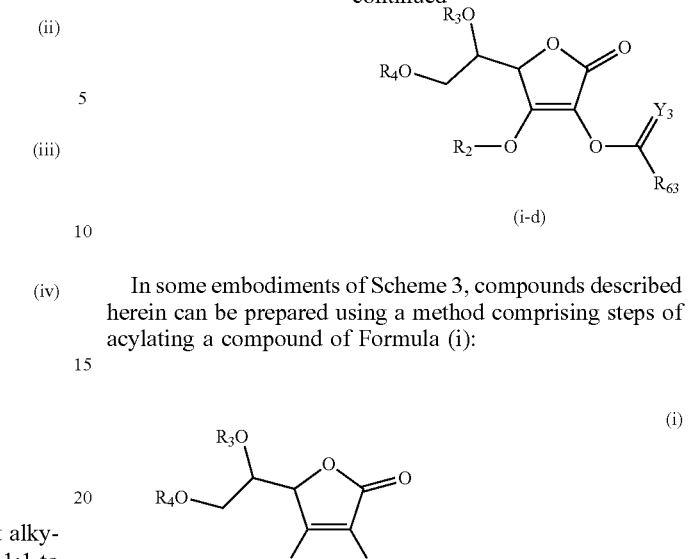

(i-d)

In some embodiments of Scheme 3, compounds described herein can be prepared using a method comprising steps of acylating a compound of Formula (i):

(i)

with an acylating agent; followed by alkylating with a soft alkylating agent of Formula (ii), (iii) or (iv):

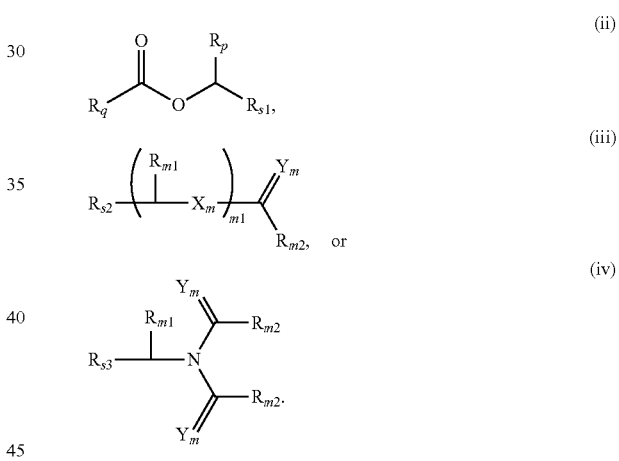

(ii)

(iii)

(iv)

In certain embodiments, the molar ratio of the acylating agent to the compound of Formula (i) is about 1:1. In certain embodiments, the acylation reaction is carried out in the presence of an organic base (e.g., pyridine) in a molar ratio of about 2:1 of the base to the compound of Formula (i) to form compound of Formula (i-c). In certain embodiments, the acylation reaction is carried out in the presence of pyridine in a molar ratio of about 2:1 of the base to the compound of Formula (i) to form compound of Formula (i-c). In certain embodiments, the molar ratio of the soft alkylating agent to the compound of Formula (i-c) is about 1:1 in the subsequent alkylation reaction. In certain embodiments, the subsequent alkylation reaction is carried out in the presence of an organic base (e.g., triethylamine). In certain embodiments, the subsequent alkylation reaction is carried out in the presence of an organic base (e.g., triethylamine) in a molar ratio of about 1:1 of the base to the compound of Formula (i-c) and a soft alkylating agent in a molar ratio of about 1:1 of the soft alkylating agent to the compound of Formula (i-c). In certain embodiments, the subsequent alkylation reaction is carried out in the presence of triethylamine in a molar ratio of about 1:1 of the base to the compound of Formula (i-c).

In some embodiments, compounds described herein can be prepared using methods shown in Scheme 4, comprising alkylating the free 2,3-enediol with a soft alkylating agent in the presence of 2 equivalent of organic or inorganic base, followed by acylation with an acylating agent in the presence of one equivalent of organic or inorganic base.

Scheme 4

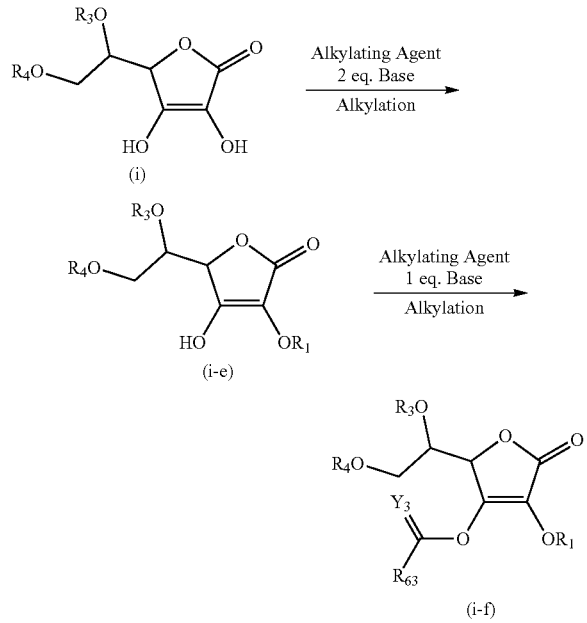

In some embodiments of Scheme 4, compounds described herein can be prepared using a method comprising steps of alkylating a compound of Formula (i):

(i)

with a soft alkylating agent of Formula (ii), (iii) or Formula (iv):

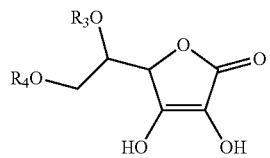

(ii)

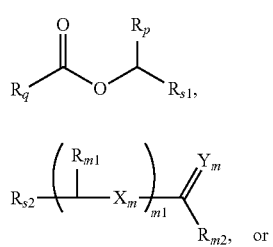

(iii)

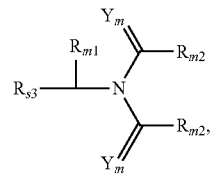

(iv)

to form a compound of Formula (i-1x):

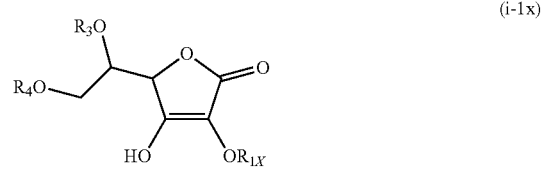

(i-1x)

followed by acylation with an acylating agent,
wherein
each of $R_{s1}$, $R_{s2}$ and $R_{s3}$ is independently a leaving group;
$R_q$ is optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, $OR^{qO}$, or $N(R^{qN})_2$;
each instance of $R^{qO}$ is independently optionally substituted $C_{1-6}$ alkyl, optionally subsubstituted heteroalkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, optionally substituted heteroaryl, or an oxygen protecting group;
each instance of $R^{qN}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, or a nitrogen protecting group;
each instance of $X_m$ is independently —O—, or —NR$^{XN}$—;
each instance of $Y_m$ is independently O or NR$^{YN}$;
each instance of $R_{m1}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, optionally substituted heteroaryl;
each instance of $R_{m2}$ is independently optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, optionally substituted heteroaryl, —OR$^{mO}$, —N(R$^{mN}$)$_2$, or two $R_{m2}$ are taken together with their intervening atoms to form an optionally substituted heterocyclic ring, or one $R_{m1}$ and one $R_{m2}$ in Formula (iv) are taken together with their intervening atoms to form an optionally substituted heterocyclic ring;
each instance of R$^{mN}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted heterocyclyl, optionally substituted heteroaryl, or a nitrogen protecting group;

each instance of $R^{mO}$ is independently optionally substituted $C_{1-6}$ alkyl, optionally substituted heteroalkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, or optionally substituted heteroaryl, or an oxygen protecting group;

$m_1$ is independently 1, 2, or 3;

$R_{1X}$ is of Formula (A) or Formula (B):

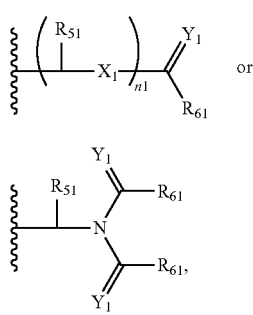

each instance of $X_1$ is independently —O—, or —$NR^{XN}$—;

each instance of $Y_1$ is independently O or $NR^{YN}$;

each instance of $R_{51}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, optionally substituted heteroaryl;

each instance of $R_{61}$ is independently optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, optionally substituted heteroaryl, —$OR^{56O}$, —$N(R^{56N})_2$, or two $R_{61}$ are taken together with their intervening atoms to form an optionally substituted heterocyclic ring, or $R_{51}$ and $R_{61}$ are taken together with the intervening atoms to form an optionally substituted heterocyclic ring;

each instance of $R^{XN}$, $R^{YN}$, and $R^{56N}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, or a nitrogen protecting group;

each instance of $R^{56O}$ is independently optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, optionally substituted heteroaryl, or an oxygen protecting group; and $n_1$ is 1, 2, or 3.

In certain embodiments of Scheme 4, the molar ratio of the soft alkylating agent to the compound of Formula (i) is about 1:1. In certain embodiments of Scheme 4, the alkylation reaction is carried out in the presence of an organic base (e.g., pyridine) in a molar ratio of about 2:1 of the base to the compound of Formula (i). In certain embodiments of Scheme 4, the molar ratio of the soft alkylating agent to the compound of Formula (i) is about 1:1 and the molar ratio of the organic base to the compound of Formula (i) is about 2:1. In certain embodiments, the alkylation reaction is carried out in the presence of pyridine in a molar ratio of about 2:1 of the base to the compound of Formula (i). In certain embodiments, the molar ratio of the acylating agent to the compound of Formula (i-e) or (i-1x) is about 1:1 in the subsequent acylation reaction. In certain embodiments, the subsequent acylation reaction is carried out in the presence of an organic base (e.g., triethylamine). In certain embodiments, the subsequent acylation reaction is carried out in the presence of an organic base (e.g., triethylamine) in a molar ratio of about 1:1 of the base to the compound of Formula (i-e) or (i-1x). In certain embodiments, the subsequent acylation reaction is carried out in the presence of triethylamine in a molar ratio of about 1:1 of the base to the compound of Formula (i-e) or (i-1x).

In some embodiments of Schemes 3 and 4, the acylating agent is of Formula (v):

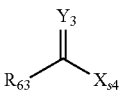

wherein $R_{63}$ and $Y_3$ are as defined herein; and $X_{s4}$ is a suitable leaving group.

As generally defined herein, $R_{s4}$ is a leaving group, i.e. an atom or a group capable of being displaced by a nucleophile. Examples of suitable leaving groups include, but are not limited to, halogen (such as Cl, Br, or I (iodine)). In some embodiments, $R_{s4}$ is halogen. In some embodiments, $R_{s4}$ is I. In some embodiments, $R_{s4}$ is Br. In some embodiments, $R_{s4}$ is a sulfonic acid ester, such as toluenesulfonate (tosylate, -OTs), methanesulfonate (mesylate, -OMs), p-bromobenzenesulfonyloxy (brosylate, -OBs), or trifluoromethanesulfonate (triflate, -OTf). In some cases, $R_{s4}$ is a brosylate, such as p-bromobenzenesulfonyloxy, a nosylate, such as 2-nitrobenzenesulfonyloxy, or a sulfonate-containing group. In some embodiments, $R_{s4}$ is a tosylate group.

As used herein, inorganic bases refer to inorganic compounds with the ability to react with, that is, neutralize acids to form salts. Exemplary inorganic bases are carbonates or hydroxides of alkali earth metals like sodium hydroxide, potassium hydroxide, sodium carbonate, potassium carbonate, sodium bicarbonate and potassium bicarbonate.

As used herein, organic bases refer to organic compounds which act as bases. In certain embodiments, organic bases are proton acceptors. Exemplary organic bases are pyridine, N-methyl morpholine, N-methyl pyrrolidine, imidazole, benzimidazole, tertiary alkyl amine such as triethyl amine, tertiary butyl amine etc, and non-nucleophilic bases such as 1,8-diazobicycloundec-7-ene (DBU) or N,N,N,N-tetramethyl-1,8-naphthalenediamine.

In certain embodiments, the synthetic reactions described herein can be carried out in the presence of a phase transfer catalyst. A phase transfer catalyst is a catalyst that facilitates the migration of a reactant from one phase into another phase where the reaction occurs. Examples of suitable phase transfer catalysts include, but are not limited to, quaternary ammonium or phosphonium salts, e.g., ammonium or phosphonium tetrabutyl halide, or ammonium or phosphonium trioctyl benzyl halide.

Pharmaceutical Compositions and Kits

The present invention provides pharmaceutical compositions comprising a compound described herein, e.g., a compound of Formula (I), (II), or (III), or pharmaceutically acceptable salts thereof, as described herein, and optionally a pharmaceutically acceptable excipient. It will be understood by one of ordinary skill in the art that the compounds described herein, or salts thereof, may be present as hydrates, solvates, or polymorphs. In certain embodiments, a provided composition comprises two or more compounds described herein. In certain embodiments, a compound described herein, or pharmaceutically acceptable salts thereof, is provided in an effective amount in the pharmaceutical composition. In certain embodiments, the effective amount is a therapeutically effective amount. In certain embodiments, the effective amount is an amount effective for treating a vitamin C deficiency in a subject. In certain embodiments, the effective amount is an amount effective for treating a skin disease and/or condition in a subject. In certain embodiments, the effective amount is a prophylactically effective amount. In certain embodiments, the effective amount is a neutraceutically effective amount.

Pharmaceutical compositions described herein can be prepared by any method known in the art of pharmacology. In general, such preparatory methods include the steps of bringing a compound described herein (the "active ingredient") into association with a carrier and/or one or more other accessory ingredients, and then, if necessary and/or desirable, shaping and/or packaging the product into a desired single- or multi-dose unit.

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, about 10 mg to about 100 mg, or about 100 mg to about 1000 mg of a compound per unit dosage form.

Also encompassed by the present discosure are kits (e.g., pharmaceutical packs). The kits provided may comprise a provided pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of a provided pharmaceutical composition or compound. In some embodiments, a provided pharmaceutical composition or compound provided in the container and the second container are combined to form one unit dosage form. In some embodiments, a provided kit further includes instructions for use.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation.

The formulations of the pharmaceutical compositions described herein may be prepared by any method known or hereafter developed in the pharmaceutical science. In general, such preparatory methods include the step of bringing the active ingredient into association with a carrier and/or one or more other accessory ingredients, and then, if necessary and/or desirable, shaping and/or packaging the product into a desired single- or multi-dose unit.

A pharmaceutical composition may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The relative amounts of the active ingredient, the pharmaceutically acceptable excipient will vary, depending upon the identity, size, and/or condition of the subject treated and further depending upon the route by which the composition is to be administered. By way of example, the composition may comprise between 0.1% and 100% (w/w) active ingredient.

Pharmaceutical compositions may comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. *Remington's The Science and Practice of Pharmacy,* 21$^{st}$ Edition, A. R. Gennaro, (Lippincott, Williams & Wilkins, Baltimore, Md., 2006) discloses various excipients used in formulating pharmaceutical compositions and known techniques for the preparation thereof. Except insofar as any conventional carrier medium is incompatible with a substance or its derivatives, such as by producing any undesirable biological effect or otherwise interacting in a deleterious manner with any other component(s) of the pharmaceutical composition, its use is contemplated to be within the scope of this disclosure.

In some embodiments, the pharmaceutically acceptable excipient is at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the pharmaceutical excipient is pharmaceutical grade. In some embodiments, the pharmaceutical excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the inventive formulations. Excipients such as cocoa butter and suppository waxes, coloring agents, coating agents, sweetening, flavoring, and perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol,); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include antioxidants, chelating agents, antimicrobial preservatives, antifungal preservatives, alcohol preservatives, acidic preservatives, formaldehyde releasing agents and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent. In some embodiments, the preservative is a formaldehyde releasing agent. Exemplary formaldehyde releasing agents include, but are not limited to, imidazolidinyl urea (see Cosmetics and Toiletries, 2013, 128(7), 474-476).

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include, but are not limited to, pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the polypeptides of the disclosure are mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type may be employed as fillers in soft and hard- filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polethylene glycols and the like.

The active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient may be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of the compound as described herein may include ointments, pastes, creams, lotions, gels, powders, solutions, sprays, inhalants and/or patches. Generally, the active component is admixed under sterile conditions with a pharmaceutically acceptable carrier and/or any needed preservatives and/or buffers as may be required. Additionally, the present disclosure contemplates the use of transdermal patches, which often have the added advantage of providing controlled delivery of an active ingredient to the body. Such dosage forms may be prepared, for example, by dissolving and/or dispensing the active ingredient in the proper medium. Alternatively or additionally, the rate may be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO 99/34850 and functional equivalents thereof.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 0.1% to about 30% (w/w) active ingredient, although the concentration of the active ingredient may be as high as the solubility limit of the active ingredient in the solvent. Formulations for topical administration may further comprise one or more of the additional ingredients described herein.

General considerations in the formulation and/or manufacture of pharmaceutical agents may be found, for example, in *Remington: The Science and Practice of Pharmacy* $21^{st}$ ed., Lippincott Williams & Wilkins, 2005.

In another aspect, the invention provides a neutraceutical composition comprising a compound of Formulae (I)-(III) and optionally a neutraceutically acceptable excipient. In certain embodiments, the neutraceutical composition of the invention may be provided in the form of a bar, beverage, drink, or snack food.

The suitable neutraceutically acceptable diluents include, but are not limited to, binding agents (e.g. pregelatinized maize starch, polyvinyl pyrrolidone or hydroxypropyl methylcellulose); fillers (e.g. lactose, microcrystalline cellulose or calcium hydrogen phosphate); lubricants (e.g. magnesium stearate, talc, or silica); disintegrants (e.g. potato starch or sodium starch glycolate); or wetting agents (e.g. sodium lauryl sulfate). The tablet may be coated by methods well known in the art. The provided neutraceutical composition may optionally include sweeteners, preservatives, vitamins (e.g. pyridoxine, riboflavin), and minerals (e.g., calcium salts, zinc salts, potassium salts), hormones (e.g. dehydroepiandrosterone (DHEA), melatonin), biochemicals (e.g., adenosine triphosphate, coenzyme A, cysteine), glandulars (e.g., edible compositions derived from glandular organs of animals such as the thyroid, pancreas, adrenal cortex), herbals (e.g., ginkgo, garlic, goldenseal, echinacea).

In another aspect, the invention provides a medical food composition comprising a compound of Formulae (I)-(III) and optionally a neutraceutically acceptable excipient. In certain embodiments, the provided medical food composition may be in the form of a bar, beverage, drink, or snack food.

The provided medical food composition can be administered to a patient as a food supplement. In certain embodiments, the provided medical food compositions are administered about once to about five times a day. In certain embodiments, the provided medical food compositions are administered about once a day. In certain embodiments, the provided medical food compositions are administered about twice a day. In certain embodiments, the provided medical food compositions are administered about three times a day. In certain embodiments, the provided medical food compositions are administered about four times a day. In certain embodiments, the provided medical food compositions are administered about five times a day.

Method of Use

The present invention provides compounds and compositions to delivery vitamin C to a subject. The present invention provides compounds and compositions thereof for treating and/or reducing the risk of a disease. In some embodiments, methods of treating a disease in a subject are provided which comprise administering an effective amount of a compound or composition as described herein to a subject in need of treatment. In certain embodiments, the effective amount is a therapeutically effective amount. In certain embodiments, the effective amount is an amount effective for treating a vitamin C deficiency in a subject. In certain embodiments, the effective amount is an amount effective for treating a skin disease and/or condition in a subject. In certain embodiments, the effective amount is a prophylactically effective amount. In certain embodiments, the effective amount is a neutraceutically effective amount. As used herein, a neutraceutically effective amount is an amount effective to provide a neutrition value and/or health or medical benefit to a subject.

In one aspect, the present invention further provides methods of delivering vitamin C to a subject comprising administering a compound or composition as described herein to the subject.

The present invention further provides methods of treating and/or preventing vitamin C deficiency comprising administering a compound a compound or composition as described herein to a subject in need thereof.

The present invention further provides methods of treating a skin disease comprising administering a compound a compound or composition as described herein to a subject in need thereof. In certain embodiments, the skin disease is selected from the group consisting of dry skin, severe dry skin, dandruff, acne, keratoses, psoriasis, eczema, skin flakiness, pruritus, melasmas, hyperkeratotic skin, and inflammatory dermatoses.

The present invention further provides methods of treating a skin condition to improve the cosmetic appearance of the skin comprising administering a compound or composition as described herein to a subject in need thereof. In certain embodiments, the skin condition is selected from the group consisting of age spots, lentigines, coarse wrinkles, fine wrinkles, warts, blemished skin, hyperpigmented skin, skin in need of cleansers and skin atrophy.

The compound or composition is typically formulated in dosage unit form for ease of administration and uniformity of dosage. It will be understood, however, that the total daily usage of the pharmaceutical compositions will be decided by the attending physician within the scope of sound medical judgment. The specific effective dose level for any particular subject will depend upon a variety of factors including the disorder being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compound or composition may be administered by any route. In some embodiments, the a compound or composition may be administered by a variety of routes, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, enteral, sublingual; by intratracheal instillation, bronchial instillation, and/or inhalation; and/or as an oral spray, nasal spray, and/or aerosol. In general the most appropriate route of administration will depend upon a variety of factors including the nature of the compound or composition, and/or the condition of the subject (e.g., whether the subject is able to tolerate oral administration). The disclosure embraces the delivery of the pharmaceutical compositions as described herein by any appropriate route taking into consideration likely advances in the sciences of drug delivery. In certain embodiments, the provided compounds or compositions are administered topically.

In certain embodiments, the compound or composition may be administered at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

In certain embodiments, the method comprises administering the provided compound or composition as the sole therapeutic agent, but in certain embodiments, the method comprises administering the provided compound or composition in combination with another therapeutic agent. The particular combination will take into account compatibility of the therapeutics and/or procedures and the desired therapeutic effect to be achieved.

In certain embodiments, the method comprises administering the provided compound or composition in combination with one or more active ingredients, which provide some benefit to the object of the application of the compound or composition, for example, hair or skin. Such active ingredients may include one or more substances such as cleaning agents, hair conditioning agents, skin conditioning agents, hair styling agents, antidandruff agents, hair growth promoters, perfumes, sunscreen compounds, chelating agent and antioxidants (e.g. vitamin E and its derivatives), pigments, moisturizers, film formers, humectants, alpha-hydroxy acids, hair colors, make-up agents, detergents, thickening agents, emulsifiers, antiseptic agents, deodorant actives and surfactants. They may include agents which enhance permeation into or through the skin, or topical pharmaceuticals such as, without limitation, corticosteriods, analgesics, anti-inflammatory agents, antibiotics, anesthetics, etc. These may all be used in conventional and/or approved amounts.

Further, the provided compounds and compositions of the invention may also include one or more absorbents, antiacne agents, anti-perspirants, anticaking agents, antifoaming agents, antimicrobial agents, antioxidants, antidandruff agents, astringents, binders, buffers, biological additives, buffering agents, bulking agents, chelating agents, chemical additives, coupling agents, conditioners, colorants, cosmetic astringents, cosmetic biocides, denaturants, drug astringents, detergents, dispersants, external analgesics, film formers, foaming agents, fragrance components, humectants, keratolytics, opacifying agents, pH adjusters, preservatives, propellants, proteins, retinoids, reducing agents, sequestrants, skin bleaching agents, skin-conditioning agents (humectants, miscellaneous, and occlusive), skin soothing agents, skin healing agents, softeners, solubilizing agents, lubricants, penetrants, plasticizers, salts, essential oils, and vitamins. The amount of each if used can very widely depending on the product. In certain embodiments, the provided compounds or compositions are administered in combination with at least one agent selected from vitamin A, vitamin B, vitamin D, vitamin E, retinyl palmitate, beta-carotene, tocopherol acetate, ascorbic acid, green tea, black tea, quercetin (flavonoids), sea kelp, pycnogenols (proanthocyanidins), selenium and alkylglycerol-AKG (shark liver oil).

By "in combination with," it is not intended to imply that the agents must be administered at the same time and/or formulated for delivery together, although these methods of delivery are within the scope of the disclosure. The agents can be administered concurrently with, prior to, or subsequent to, one or more other desired therapeutics or medical procedures. In general, each agent will be administered at a dose and/or on a time schedule determined for that agent.

EXAMPLES

In order that the invention described herein may be more fully understood, the following examples are set forth. It should be understood that these examples are for illustrative purposes only and are not to be construed as limiting this invention in any manner.

Synthesis of 2,3-O-(dipivaloyloxymethyl)-5,6-isopropylidene-L-ascorbic acid and 2-O-(pivaloyl)-3-O-(pivaloyloxymethyl)-5,6-isopropylidene-L-ascorbic acid (Scheme 5)

To 4 ml of chloromethyl pivalate (Aldrich-Sigma) (4.2 g, 27.8 mmole) dissolved in 20 ml of acetone was added 4.2 g (27.8 mmole) of NaI. The suspension was stirred for 2.5 hours at room temperature (J. Org. Chem. 1983, 48, 3277-3281). Vitamin C acetonide (2.0 g, 9.25 mmole) and $K_2CO_3$ (2.6 g, 18.5 mmole) were added and the suspension was stirred overnight at room temperature. The suspension was diluted with 100 ml of dichloromethane and filtered. The filtrate was concentrated in vacuo to give 5.37 g of oil containing less than a molar equivalent of acetone residue. The oil was dissolved in 150 ml of dichloromethane and washed quickly with 15 ml of water saturated with $NaHCO_3$. The organic layer was separated, dried over $Na_2SO_4$ with stirring for 30 min and concentrated to give 4.25 g of an oil. The oil was chromatographed on 140 g of neutral silica gel using pure hexanes to 30:70 ethyl acetate:hexanes as the elutent. The first product off the column was the 2,3-diSMtC4 product, rf 0.85 (1:1, ethyl acetate:hexane). The fractions containing the first product were concentrated in vacuo to give 1.55 g (38% yield). The second product off the column was the 2-ActC4-3-SMtC4 product, rf 0.80 (1:1, ethyl acetate:hexanes). The fractions containing the second product were concentrated in vacuo to give 1.40 g (36% yield).

Scheme 5

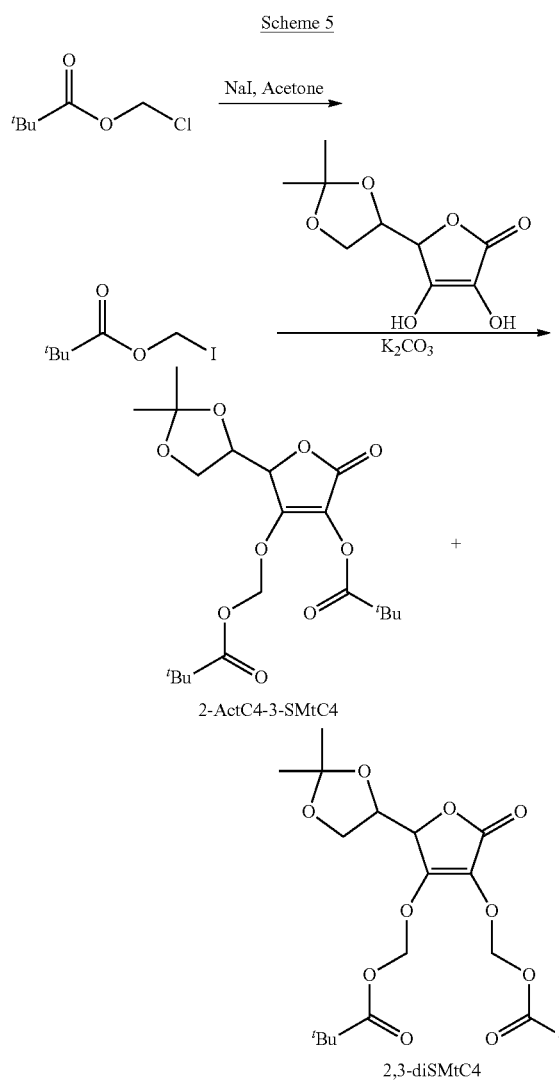

Synthesis of I-CH(CH₃)—O—(C=O)CH₃ (Scheme 6)

To 1.0 g (7.57 mmole) of paraldehyde in 20 ml of dichloromethane was added 1.78 g (22.7 mmole) of acetyl chloride in 10 ml of dichloromethane. Then NaI (3.97, 26.5 mmole), I₂ (3.8 mg, 0.151 mmole) and AlCl₃ (100.9 mg, 0.757 mmole) were added to the reaction solution (Synthesis, 2008, 272). The suspension was stirred overnight at room temperature wrapped in aluminum foil to protect the reaction from light. The suspension was filtered by vacuum and the filtrate was diluted with 70 ml of dichloromethane. The dichloromethane solution was washed quickly with 10 ml water containing 10% Na₂S₂O₃ and 10 ml of brine. The organic layer was separated, dried over Na₂SO₄ for 30 minutes with stirring and filtered. The filtrate was concentrated in vacuo to give 4.05 g of an oil. The amount of I-CH(CH₃)—O—(C=O)CH₃ in the oil was calculated from the ratio of the (C=O)CH₃ ¹H NMR absorption of the product to the CH₂Cl₂ ¹H NMR absorption of the solvent. The amount was estimated to be 83.5% of the 4.05 g of oil.

Scheme 6

Synthesis of -O-(acetyl)-3-O-(acetyloxyethylidene)-5,6-isopropylidene-L-ascorbic acid (Scheme 7)

The I-CH(CH₃)—O—(C=O)CH₃ product from the previous reaction (4.05 g, estimated 15.8 mmole of alkylating agent) was added to an acetone (50 ml) suspension containing vitamin C acetonide (1.36 g, 6.3 mmole) and K₂CO₃ (1.74 g, 12.6 mmole). The suspension that resulted was stirred overnight at room temperature wrapped in aluminum foil to protect the reaction from light. The suspension was concentrated in vacuo. The residue was dissolved in 80 ml of dichloromethane and washed with 20 ml of water saturated with NaHCO₃. The organic later was separated, dried over Na₂SO₄ for 30 min with stirring, filtered and the filtrate was concentrated in vacuo to give a yellow oil. The oil was chromatographed on 200 g of neutral silica gel using hexanes to 35:65 ethyl acetate:hexanes as the eluent. The second fraction was the desired product (1.24 g in 57% yield) exhibiting the characteristic ¹³C NMR spectrum with C2 at 115.88 and C3 at 156.28, rf 0.43 (ethyl acetate: hexanes, 1:1).

Scheme 7

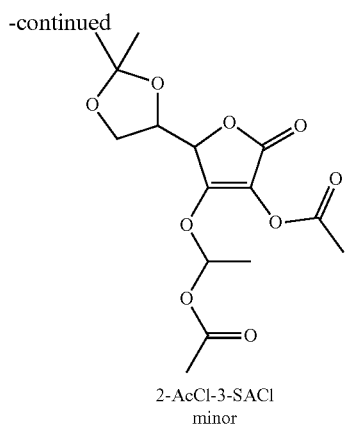

2-AcCl-3-SACl
minor

5,6-Isopropylidene-L-ascorbic acid

The synthesis of 5,6-isopropylidene-L-ascorbic acid from L-ascorbic acid followed the procedure reported by Jung and Shaw (J. Am. Chem. Soc., 102 [1980] 6304). L-Ascorbic acid (10.01 g, 0.0568 mol) was added to a 125 mL Erlenmeyer flask with approximately 50 mL of acetone (0.681 mol). The slurry was stirred as 1 mL of acetyl chloride (0.0140 mol) was added. The mixture was corked, sealed with Parafilm and left to stir at room temperature for 2-3 hours. The flask was then stored in a refrigerator (7° C.) for 20-24 hours. The solid from this mixture was isolated by vacuum filtration, and was rinsed with cold acetone. After drying at room temperature, the solid weighed 9.09 g, (74%). The identity of the solid as 5,6-isopropylidene-L-ascorbic acid was confirmed by NMR and a melting point of 202-205° C. (crude literature [J. Am. Chem. Soc., 102 (1980) 6304]: 195-200° C.); recrystallization from acetone/hexane did not improve the melting point (recrystallized literature [Can. J. Chem., 47 (1969) 2498]: 217-222° C.). $^1$H NMR (Me$_2$SO-d$_6$) δ 1.255 (6H, s), 3.882 (1H, dd, J=8.0, 6.8 Hz), 4.098 (1H, dd, J=7.8, 8.0 Hz), 4.2615 (1H, td, J=2.8, 6.6 Hz), 4.7095 (1H, d, 2.8 Hz), 8.482 (1H, s), 11.293 (1H, s).

5,6-Isopropylidene-2-O-(propyloxycarbonyl)-L-ascorbic acid and other 2-O-acyl derivatives 5,6-Isopropylidene-L-ascorbic acid (1.51 g, 0.00698 mol) and propyl chloroformate (0.86 g, 0.00702 mol) were added to a 150 mL round-bottom flask with approximately 50 mL of dichloromethane. The mixture was stirred and 1.2 mL of pyridine (0.0148 mol) in approximately 20 mL of dichloromethane was added. The flask was corked and the contents were left to stir for 20-24 hours. The orange-tinted solution was then rinsed with dichloromethane into a 250 mL reparatory funnel and washed three times with 10 mL aliquots of 1 M HCl. The washed dichloromethane layer was dried over sodium sulfate for 1 hour, then concentrated in vacuo without heating to give 1.67 g (79%) of 5,6-isopropylidene-2-O-(propyloxycarbonyl)-L-ascorbic acid. The product could be somewhat purified by trituration in hexane, but due to observed instability the product was usually moved forward to the next reaction. $^1$H NMR (CDCl$_3$) δ 1.006 (3H, t, J=7.6 Hz), 1.381 (3H, s), 1.406 (3H, s), 1.773 (2H, q, J=7.2 Hz), 4.103 (1H, dd, J=6.8, 8.8 Hz), 4.207 (1H, dd, J=6.8, 8.2 Hz), 4.268 (2H, t, J=6.6 Hz), 4.441 (1H, td, J=2.8, 6.7 Hz). 4.700 (1H, d, J=2.4 Hz).

The $^1$H NMR shifts of the straight-chain alkyl carbonate series of 2-O-acyl derivatives of 5,6-isopropylidene-L-ascorbic acid in CDCl$_3$ are shown in Table 1.

TABLE 1

The $^1$H NMR shifts of the straight-chain alkyl carbonate series of 2-O-acyl derivatives of 5,6-isopropylidene-L-ascorbic acid in CDCl$_3$.

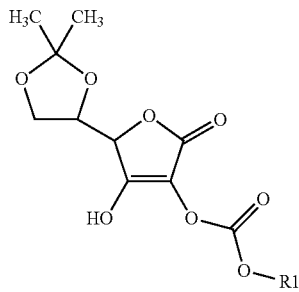

| R1 | $^1$H shifts associated with 5,6-isopropylidene-L-ascorbic acid | | | | | | $^1$H shifts associated with R1 | | |
|---|---|---|---|---|---|---|---|---|---|
|  | (CH$_3$)$_2$C(O)$_2$ | | 6C—H | 6C—H | 5C—H | 4C—H | | | |
| CH$_3$ | 1.377 | 1.404 | 4.103 | 4.206 | 4.442 | 4.716 |  | 3.959 |  |
| CH$_2$CH$_3$ | 1.379 | 1.405 | 4.103 | 4.206 | 4.440 | 4.703 | 1.405 |  | 4.373 |
| CH$_2$CH$_2$CH$_3$ | 1.381 | 1.406 | 4.103 | 4.207 | 4.441 | 4.700 | 1.006 | 1.773 | 4.268 |

5,6-Isopropylidene-3-O-(pivaloyloxymethyl)-2-O-(ethyloxycarbonyl)-L-ascorbic acid and other 3-O-(pivaloyloxymethyl)-2-O-acyl derivatives The pivaloyloxymethylation reaction was similar for all derivatives, and generally followed a procedure published by Sloan and Koch for pivaloyloxymethylation of phenols (J. Org. Chem., 48 [1983] 3777). The use of triethylamine rather than an inorganic base to ionize the 2-acyl derivative follows a reaction published by Wheeler et. al. for the synthesis of acyloxymethyl derivatives of carboxylic acids (J. Med. Chem., 22 [1979] 657). Chloromethyl pivalate (0.48 g, 0.00319 mol) and sodium iodide (0.48 g, 0.00320 mol) were added to a 150 mL round-bottom flask with approximately 50 mL of acetone. The mixture was stirred while corked and covered with aluminum foil for 5-6 hours to form the iodomethyl pivalate in situ. 5,6-Isopropylidene-2-O-(ethyloxycarbonyl)-L-ascorbic acid (0.91 g, 0.00316 mol) was dissolved in approximately 20 mL of acetone in a 250 mL round-bottom flask with stirring. Triethylamine (0.46 mL, 0.00375 mol) dissolved in approximately 15 mL of acetone and the iodomethyl pivalate suspension in acetone were rinsed into the well stirred 5,6-isopropylidene-2-O-(ethyloxycarbonyl)-L-ascorbic acid solution with acetone. The flask was corked, covered with foil and left to stir for 18-24 hours. The resulting suspension was concentrated in vacuo without heating to an orange solid. This solid was suspended in approximately 75 mL of dichloromethane and stirred for 1 hour. The dichloromethane suspension was washed 5 times with 10-15 mL aliquots of water. The dichloromethane layer was dried over sodium sulfate for 1 hour, then was concentrated in vacuo without heating to give a yellow oil: 1.07 g (84%). The product was purified by column chromatography using 87 g of silica gel. The product came through in the first 100 mL volume of 1:1 acetone:hexane, after five 100 mL volumes of hexane and three 100 mL volumes of 1:3 acetone:hexane. The fraction containing the product was concentrated in vacuo without heating to give a yellow oil weighing 0.68 g (54% or 42% overall yield from ascorbic acid acetonide). $^1$H NMR (CDCl$_3$) δ 1.223 (9H, s), 1.334 (3H, s), 1.379 (3H, t, J=7.2 Hz), 1.382 (3H, s), 4.081 (1H, dd, J=6.2, 8.6 Hz), 4.157 (1H, dd, J=7.0, 8.2 Hz), 4.330 (2H, td, J=2.0, 7.2 Hz), 4.366 (1H, td, J=2.4, 6.6 Hz), 4.704 (1H, d, J=2.8 Hz), 5.889 (2H, dd, J=5.8, 13.8 Hz).

5,6-Isopropylidene-2-O-acetyl-L-ascorbic acid

The synthesis of 5,6-isopropylidene-2-O-acetyl-L-ascorbic acid generally followed the synthesis of the other 2-O-acyl derivatives, but was slightly altered due to the increased reactivity of the starting material and suspected increased water solubility of the product. 5,6-Isopropylidene-L-ascorbic acid (1.00 g; 0.00463 mol) was added to a 150 mL round-bottom flask with acetyl chloride (0.38 g; 0.00484 mol) and approximately 20 mL of ice cold dichloromethane. The mixture was stirred as 0.76 mL of pyridine (0.00935 mol) dissolved in approximately 15 mL of cold dichloromethane was added. The reaction mixture was stirred overnight in an ice bath. The mixture was then diluted with approximately 100 mL of dichloromethane and washed with three 5 mL aliquots of 1 M HCl. The organic layer was dried over sodium sulfate for 1 hour before being concentrated in vacuo without heating to a white solid weighing 0.91 g (76.1%). Due to instability observed in the other 2-O-acyl derivatives, the crude product was moved forward to the next reaction. $^1$H NMR (CDCl$_3$) δ 1.379 (3H, s), 1.406 (3H, s), 2.361 (3H, s), 4.102 (1H, dd, J=6.8, 8.8 Hz), 4.208 (1H, dd, J=7.0, 8.2 Hz), 4.439 (1H, td, J=2.8, 6.8 Hz), 4.696 (1H, d, J=2.4 Hz).

The $^1$H NMR shifts of exemplary straight-chain alkyl carbonate series of 3-(pivaloyloxymethyl)-2-O-acyl derivatives of 5,6-isopropylidene-L-ascorbic acid in CDCl$_3$ are shown in Table 2.

TABLE 2

The $^1$H NMR shifts of the straight-chain alkyl carbonate series of 3-(pivaloyloxymethyl)-2-O-acyl derivatives of 5,6-isopropylidene-L-ascorbic acid in CDCl$_3$.

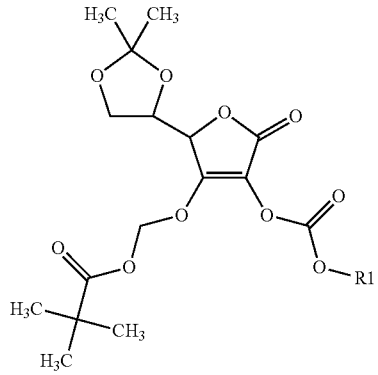

| | $^1$H shifts of 5,6-isopropylidene-L-ascorbic acid. | | | | | | $^1$H shifts of POM$^a$ | |
|---|---|---|---|---|---|---|---|---|
| R1 | (CH$_3$)$_2$C(O)$_2$ | 6C—H | 6C—H | 5C—H | 4C—H | $^1$H shifts of R1 | C(CH$_3$)$_3$ | OCH$_2$O |
| CH$_3$ | 1.334 | 1.384 | 4.082 | 4.153 | 4.367 | 4.698 | 3.929 | 1.221 | 5.886 |
| CH$_2$CH$_3$ | 1.334 | 1.382 | 4.081 | 4.157 | 4.366 | 4.704 | 1.379   4.330 | 1.223 | 5.889 |
| CH$_2$CH$_2$CH$_3$ | 1.333 | 1.382 | 4.080 | 4.153 | 4.366 | 4.703 | 0.996  1.763  4.236 | 1.222 | 5.888 |

$^a$POM = pivaloyloxymethyl.

5,6-Isopropylidene-2-O-(3,6-dioxyheptyloxycarbonyl)-L-ascorbic acid

The synthesis 5,6-isopropylidene-2-O-(3,6-dioxyheptyloxycarbonyl)-L-ascorbic acid followed the synthesis of the other 2-O-acyl derivatives, but the in situ synthesis of a chloroformate followed a procedure presented by Majumdar et. al. (AAPS PharmSciTech, 13 [2012], 853). Triphosgene (0.99 g; 0.00334 mol) was dissolved in approx. 10 mL of dichloromethane in a 150 mL round-bottom flask, followed by 0.82 mL of pyridine (0.0101 mol) dissolved in approx. 10 mL of dichloromethane. The cloudy mixture was stirred as methoxyethyloxyethyl alcohol (1.21 g; 0.0101 mol) dissolved in approx. 5 mL of dichloromethane was added. The mixture was stirred for an hour at room temperature to generate methoxyethyloxyethyl chloroformate in situ, then for 30 minutes in an ice bath. 5,6-Isopropylidene-L-ascorbic acid (2.16 g; 0.00999 mol) was dissolved in approx. 20 mL of cold dichloromethane in a 250 mL round-bottom flask, followed by 1.63 mL of pyridine (0.0201 mol) dissolved in approx. 10 mL of cold dichloromethane. This mixture was stirred as the methyloxyethyloxyethyl chloroformate reaction mixture was rinsed in with a small amount of cold dichloromethane. The mixture was left to stir at room temperature overnight. The resulting yellow mixture was then diluted with approximately 90 mL of dichloromethane and washed with five 6 mL aliquots of 1 M HCl. The yellow organic layer was dried over sodium sulfate for 1 hour before being concentrated in vacuo without heating to a yellow oil weighing 2.82 g (77.9%). Due to instability observed in the other 2-O-acyl derivatives, the crude product was moved forward to the next reaction. $^1$H NMR (CDCl$_3$) δ 1.375 (3H, s), 1.408 (3H, s), 3.401 (3H, s), 3.588 (2H, m), 3.669 (2H, m), 3.773 (2H, t, J=4.6 Hz), 4.103 (1H, dd, J=6.6, 8.8 Hz), 4.196 (1H, dd, J=6.8, 8.8 Hz), 4.450 (3H, m), 4.708 (1H, d, J=3.2 Hz).

5,6-Isopropylidene-3-O-(acetyloxymethyl)-2-O-acetyl-L-ascorbic acid and other 3-O-(acetyloxymethyl)-2-O-acyl derivatives The syntheses of the 3-O-(acetyloxymethyl)-2-O-acyl derivatives were similar to the syntheses of the 3-O-(pivaloyloxymethyl)-2-O-acyl derivatives, but without the need to generate an iodomethyl reactant in situ. 5,6-Isopropylidene-2-O-acetyl-L-ascorbic acid (0.91 g; 0.00352 mol) was dissolved in approx. 100 mL of acetone in a 250 mL round-bottom flask, followed by triethylamine (0.50 mL; 0.00359 mol) dissolved in approx. 20 mL of acetone, and then bromomethylacetate (0.55 g; 0.00360 mol) dissolved in approx. 20 mL of acetone. This mixture was stirred overnight at room temperature. The resulting yellow suspension with white solid was concentrated in vacuo to an orange, opaque oil, which was taken up into 200 mL of dichloromethane to give a clear, yellow solution. The solution was washed with five 5 mL aliquots of water before drying over sodium sulfate for 1 hour. The dry dichloromethane solution was concentrated in vacuo without heating to a viscous orange oil weighing 0.87 g (74.8%). Following the same column procedure as in the other 3-O-alkyl derivatives, 5,6-isopropylidene-3-O-(acetyloxymethyl)-2-O-acetyl-L-ascorbic acid was purified to a white solid weighing 0.58 g (49.9%, or 38% overall yield from ascorbic acid acetonide). The white solid had a melting point of 87-89° C. The other 3-O-acetyloxymethyl derivatives were not solid. $^1$H NMR (CDCl$_3$) δ 1.349 (3H, s), 1.392 (3H, s), 2.109 (3H, s), 2.301 (3H, s), 4.084 (1H, dd, J=6.4, 8.4 Hz), 4.160 (1H, dd, J=7.0, 8.8 Hz), 4.362 (1H, td, J=2.4, 6.4 Hz), 4.720 (1H, d, J=2.4 Hz), 5.817 (2H, dd, J=6.0, 34.4 Hz).

The $^1$H NMR shifts of the 3-(acetyloxymethyl)-2-O-acyl derivatives in CDCl$_3$ are shown in Table 3.

TABLE 3

The $^1$H NMR shifts of the 3-(acetyloxymethyl)-2-O-acyl derivatives in CDCl$_3$.

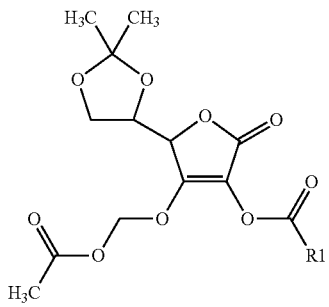

| | $^1$H shifts of 5,6-isopropylidene-L-ascorbic acid. | | | | | $^1$H shifts of R1 | | | | | $^1$H shifts of ACOM$^a$ | |
|---|---|---|---|---|---|---|---|---|---|---|---|---|
| R1 | (CH$_3$)$_2$C(O)$_2$ | | 6C—H | 6C—H | 5C—H | 4C—H | | | | | CH$_3$ | OCH$_2$O |
| CH$_3$ | 1.349 | 1.392 | 4.084 | 4.160 | 4.362 | 4.720 | | | 2.301 | | 2.109 | 5.817 |
| DiPEG$^b$ | 1.344 | 1.384 | 4.082 | 4.166 | 4.367 | 4.735 | 3.380 | 3.556 | 3.670 | 3.786 4.438 | 2.123 | 5.852 |
| PO$^c$ | 1.347 | 1.390 | 4.085 | 4.159 | 4.362 | 4.705 | 1.002 | | 1.771 | 4.243 | 2.116 | 5.852 |

$^a$ACOM = acetyloxymethyl.
$^b$DiPEG = 3,6-dioxyheptyloxycarbonyl.
$^c$PO = propyloxy.

Exemplary synthesized compounds of Formula (E-1) based on the general Scheme 1 are shown in Table 4.

TABLE 4

Exemplary synthesized compounds of Formula (E-1)

Formula (E-1)

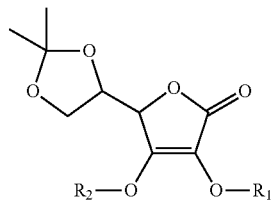

| Entry | R$_2$ | R$_1$ | Abreviation |
|---|---|---|---|
| 1 | CH$_2$—O—(C=O)CH$_3$ | (C=O)CH$_3$ | 2-AcC1-3-SMC1 |
| 2 | CH$_2$—O—(C=O)C$_2$H$_5$ | CH$_2$—O—(C=O)C$_2$H$_5$ | 2,3-diSMC2 |

TABLE 4-continued

Exemplary synthesized compounds of Formula (E-1)

Formula (E-1)

| Entry | $R_2$ | $R_1$ | Abreviation |
|---|---|---|---|
| 3 | $CH_2$—O—(C=O)$C_2H_5$ | (C=O)$C_2H_5$ | 2-AcC2-3-SMC2 |
| 4 | $CH_2$—O—(C=O)$C_4H_9$ | $CH_2$—O—(C=O)$C_4H_9$ | 2,3-diSMC4 |
| 5 | $CH_2$—O—(C=O)$C_4H_9$ | (C=O)$C_4H_9$ | 2-AcC4-3-SMC4 |
| 6 | $CH_2$—O—(C=O)t$C_4H_9$ | $CH_2$—O—(C=O)t$C_4H_9$ | 2,3diSMtC4 |
| 7 | $CH_2$—O—(C=O)t$C_4H_9$ | (C=O)t$C_4H_9$ | 2-ActC4-3-SMtC4 |
| 8 | $CH_2$—O—(C=O)$C_5H_{11}$ | $CH_2$—O—(C=O)$C_5H_{11}$ | 2,3diSMC5 |
| 9 | $CH_2$—O—(C=O)$C_5H_{11}$ | (C=O)$C_5H_{11}$ | 2-AcC5-3-SMC5 |
| 10 | $CH(CH_3)$—O—(C=O)t$C_4H_9$ | $CH(CH_3)$—O—(C=)t$C_4H_9$ | 2,3-diSAtC4 |
| 11 | $CH(CH_3)$—O—(C=O)t$C_4H_9$ | (C=O)t$C_4H_9$ | 2-ActC4-3-SAtC4 |
| 12 | $CH(CH_3)$—O—(C=O)$CH_3$ | (C=O)$CH_3$ | 2-AcC1-3-SAC1 |
| 13 | $CH_2$—O—(C=O)O$C_3H_7$ | $CH_2$—O—(C=O)O$C_3H_7$ | 2,3-diSMOC3 |
| 14 | $CH_2$—O—(C=O)O$C_3H_7$ | (C=O)O$C_3H_7$ | 2-AcOC3-3-SMOC3 |
| 15 | $CH_2$—O—(C=O)$C_6H_4OCH_3$ | $CH_2$—O—(C=O)$C_6H_4OCH_3$ | 2,3-diSMAr |
| 16 | $CH_2$—O—(C=O)$C_6H_4OCH_3$ | (C=O)$C_6H_4OCH_3$ | 2-AcAr-3-SMAr |
| 17 | $CH_2$—O—(C=O)t$C_4H_9$ | (C=O)O$CH_3$ | 2-AcOC1-3-SMtC4 |
| 18 | $CH_2$—O—(C=O)t$C_4H_9$ | (C=O)O$C_2H_5$ | 2-AcOC2-3-SMtC4 |
| 19 | $CH_2$—O—(C=O)t$C_4H_9$ | (C=O)O$C_3H_7$ | 2-AcOC3-3-SMtC4 |
| 20 | $CH_2$—O(C=O)$CH_3$ | (C=O)$CH_3$ | 2-AcC1-3-SMC1 |
| 21 | $CH_2$—O(C=O)$CH_3$ | (C=O)O$C_3H_7$ | 2-AcOC3-3-SMC1 |
| 22 | $CH_2$—O(C=O)$CH_3$ | (C=O)O($CH_2CH_2O)_2CH_3$ | 2-AcO(C2O)$_2$C1-3-SMC1 |
| 23 | $CH_2$—N-Phth | $CH_2$—N-Phth | 2,3-diSMPhth |
| 24 | $CH_2$—N-Suc | $CH_2$—N-Suc | 2,3-diSMSuc |
|  | N-Phth = | N-Succ = |  |

Exemplary synthesized compounds of Formula (E-2) based on the general scheme 1 are shown in Table 5 as follows.

TABLE 5

Exemplary synthesized compounds of Formula (E-2)

Formula (E-2)

| Entry | $R_2$ | $R_1$ | Abreviation |
|---|---|---|---|
| 1 | $CH_2$—O—(C=O)$C_5H_{11}$ | (C=O)$C_5H_{11}$ | 2-AcC5-3-SMC5 |
| 2 | $CH_2$—N-Phth | $CH_2$—N-Phth | 2,3-diSMPhth |

The exemplary compounds in Table 4 and Table 5 were subject to elemental analysis. The chemical shifts for the O—$CH_2$—O, 4-CH, 5-CH and 6-$CH_2$ absorptions in the $^1$H NMR spectra are consistent in both the 2, 3-diSM(A) and 2-Ac-3-SM(A) species for each compound in the series. From J. Org. Chem., 69 (2004) 7026-7032, the following $^1$H and $^{13}$C absorptions were obtained for 2-alkyl-3-acyl, 3-alkyl-2-acyl and 2-alkyl-3-alkyl derivatives of vitamin C acetonide (Table 6). The $^1$H and $^{13}$C absorptions of the compounds in the present invention are shown in Table 7.

TABLE 6

$^1$H and $^{13}$C absorptions of vitamin C acetonide derivatives in literature (J. Org. Chem., 69 (2004) 7026-7032)

|  | 2-C $^{13}$C | 3-C $^{13}$C | 4-H $^1$H |
|---|---|---|---|
| 2-alkyl-3-acyl | 130.1-131.2 | 142.3-144.6 | 5.15-5.18 |
| 3-alkyl-2-acyl | 114.5.114.8 | 159.5-160.7 | 4.67-4.71 |
| 2-alkyl-3-alkyl | 121.2-123.0 | 155.1-156.4 | 4.53-4.55 |

TABLE 7

$^1$H and $^{13}$C absorptions of exemplary compounds in the present invention

|  | 2-C $^{13}$C | 3-C $^{13}$C | 4-H $^1$H |
|---|---|---|---|
| 2-ActC4-3-SMtC4 | 116.10 | 156.58 | 4.69 |
| 2,3-diSMtC4 | 120.42 | 154.41 | 4.57 |

Solubilities

Aqueous solubility ($S_{AQ}$): Each compound (50-100 mg) was stirred at room temperature (rt, 23±0.5° C.) in 4 small vials containing 2 mL of Millipore $H_2O$ for 1 hour. After the suspensions were allowed to settle, about 0.020 mL of each supernatant was added to a UV cuvette containing about 2.98 mL of Millipore $H_2O$, and the UV absorption of each solution was measured. The concentration, $S_{AQ}$, of each compound was determined using Beer's Law and the previously measured molar absorptivities ($\epsilon$, L mol$^{-1}$cm$^{-1}$) of each compound in water where A is the absorbance (no units), b is the path length of the cuvette (cm) and c is the concentration (mol L$^{-1}$) of each compound in the supernatant.

Beer's Law:

$A=\epsilon bc$ $c=A/\epsilon b$

Lipid solubility ($S_{LIPID}$): Each compound (50-100 mg) was stirred at rt in four test tubes containing 2 or 3 mL of isopropyl myristate (IPM) or octanol (OCT) overnight. The saturated suspensions were filtered and about 0.020 mL of each filtrate was diluted with 5 or 10 mL of acetonitrile (ACN). The UV absorbances of the diluted filtrates were measured and the concentrations of each compound in either IPM ($S_{IPM}$) or OCT ($S_{OCT}$) were determined using Beer's Law as above but using previously measured $\epsilon$ of each compound in ACN.

Partition Coefficients

Samples of about 0.020 mL of the aqueous solutions from the determination of $S_{AQ}$ were diluted with about 2.98 mL of Millipore $H_2O$, and the UV absorbances of the diluted solutions were measured: AB or absorbance before partitioning. The undiluted aqueous solutions (1 or 2 mL) were then partitioned against 1-5 mL of OCT or IPM in a separatory funnel with vigorous shaking for 10 sec. After the biphasic mixtures were allowed to settle, samples of the aqueous phases (about 0.020 mL) were diluted with about 2.98 mL of Millipore water; and the UV absorbances of the diluted aqueous phases were measured to give an absorbance after partitioning: AA. The partition coefficient between a lipid and water ($K_{LIPID:AQ}$) was calculated as follows:

$K_{LIPID:AQ}=(V_{AQ}/V_{LIPID})(AB-AA/AA)$

The solubilities in the lipid, $S_{OCT}$ or $S_{IPM}$, could also then be calculated from $K_{LIPID:AQ}=S_{LIPID}/S_{AQ}$.

Hydrolysis of Prodrugs

The hydrolysis of the prodrugs of ascorbic acid acetonide were followed by measuring the loss of the UV absorbances of the prodrugs at 219 nm and the appearance of the absorbance of ascorbic acid acetonide at 254 nm. For example, 10.2 mg of 2-ethylcarbonyl-3-ethylcarbonyloxymethyl-5,6-isopropylidene ascorbic acid was dissolved in 2 mL ACN. A sample (0.050 mL) of the solution was added to 2.95 mL of pH 7.1 buffer, and UV spectra were acquired every 30 min for 36 hours. The half life for the appearance of ascorbic acid acetonide from the prodrug was 18 hours. Under similar conditions the half life of the 2,3-biphthalimidomethyl prodrug of ascorbic acid acetonide was 8.25 hours.

In order to verify that ascorbic acid acetonide was being produced during the hydrolysis, the hydrolysis at pH 10.0 was followed by iodine titration. If the free enediol of ascorbic acid acetonide is present, it is oxidized to dehydroascorbic acid acetonide while the iodine is reduced to iodide ions. If no free enediol is present, the excess iodine reacts with a starch indicator to give a blue color. During the titration, as iodine solution was added to the prodrug solution, a blue color formed initially but faded as the free enediol was released by hydrolysis of the prodrug and the iodine was reduced to iodide. In the case of the hydrolysis of 2-ethylcarbonyl-3-ethylcarbonyloxymethyl-5,6-isopropylidene ascorbic acid, it took several 5-10 minute intervals after the sequential addition of iodine solution to give a persistent blue color. According to the titration, 95.7% of the theoretical amount of ascorbic acid acetonide was formed from hydrolysis of the prodrug.

Acetonide Cleavage

Almost all of the prodrugs were initially synthesized as derivatives of 5,6-isoproplidene (acetonide) ascorbic acid to protect ascorbic acid from side reactions on the 5- and 6-hydroxyl groups. The general procedure of Wu et al. Letters in Organic Chemistry 3 (2006) 271-274 was used. Antimony trichloride ($SbCl_3$) (0.1-0.2 mmol) was added to a well stirred ACN (10 mL) solution of the prodrug of ascorbic acid acetonide (1.0 mmol). A small amount (1.0 mmol) of water was added and the reaction was followed by TLC. Upon completion of the reaction, the mixture was treated with 0.5 mL of saturated $NaHCO_3$ solution and the mixture was concentrated at a rotoevaporator to give a solid. The solid was suspended in 50 mL of dicholoro-methane, the precipitate was filtered and the filtrate was evaporated to give an oil. In the example of 2-pentylcarbonyl-3-pentylcarbonyloxymethyl-5,6-isopropylidene ascorbic acid, the yield of analytically pure 2-pentylcarbonyl-3-pentylcarbonyloxymethyl ascorbic acid was 73%. NMR analysis confirmed the disappearance of the 6 protons at 1.4 ppm associated with the acetonide. There is also a shift of the singlet C4 hydrogen from 4.75 to 4.9 as well as a shift of the multipliplet C5 and C6 protons, from 4.4 and 4.0-4.2 to 4.0 and 3.75-3.85 ppm, respectively.

Prediction of Flux

In order to accurately predict flux through a specific membrane all that are needed are the solubilities of a molecule in a lipid and in water, its molecular weight and the membrane specific and vehicle specific Roberts-Sloan RS equation (J. Pharm. Sci., 1999, 88, 515-522).

The importance of the water solubility, $S_{AQ}$, and the lipid solubility, $S_{LIPID}$, of a molecule that is diffusing through any membrane, regardless of whether the vehicle is a lipid or water, was first reported in 1984 (Int. J. Pharm., 1984, 21, 251-264). Trends in the maximum flux of prodrugs through hairless mouse skin in vitro from an isopropyl myristate, IPM, vehicle, $J_{MMIPM}$ of the prodrugs suggested that $J_{MMIPM}$ depended on both their solubility in IPM, $S_{IPM}$, and in water, $S_{AQ}$, and that the maximum flux for members of a homologous series of prodrugs was exhibited by that member that was the most water soluble. The dependence of $J_{MMIPM}$ on $S_{AQ}$ and $S_{IPM}$ was attributed to the arrangement of the components of the lipid bilayers in the lipid matrix of the stratum corneum, SC, which is considered to be the rate limiting barrier to diffusion. It was proposed that the lipid bilayer presented alternating lipid and aqueous phases in which a molecule must dissolve and through which it must traverse during diffusion across the SC. Thus, in order to optimize flux across the SC, a molecule must exhibit solubility in both the lipid and aqueous phases of the bilayers.

Subsequent papers on prodrugs of 5-Fluorouracil, 5-FU, 6- mercaptopurine, 6-MP, and theophylline, ThH, confirmed the original observations in a qualitative manner. It was not until 1999 (J. Pharm. Sci., 1999, 88, 575) that sufficient internally consistent physicochemical data, log $S_{IPM}$ and log $S_{AQ}$, and flux data, log $J_{MMIPM}$, was available to develop a robust equation that provided a good fit to existing data (n=42) at that time. This equation was the Roberts-Sloan RS equation. RS was developed from Fick's Law but it was expanded to include solubilities in lipid and water (in addition to molecular weight, MW) as the independent variables and to accommodate a lipid vehicle. RS may also be considered a transformation of the popular Potts-Guy (Pharm. Res., 1992, 9, 663-669), PG, equation but RS differs significantly from PG in that the dependent variable in RS is flux while permeability coefficient, P, is the dependent variable in PG. P is reported in units of distance/time so it does not include amount diffusing whereas flux is reported in units of amount/(time)(area). Since amount delivered is an essential measurement to judge therapeutic effectiveness, P is not practically useful. The n=42 log $J_{MMIPM}$ database was eventually increased to n=94 with the synthesis, characterization and evaluation of more prodrugs (AAPS PharmSci. Tech., 2012, 13, 853-862). When the n=94 log $J_{MMIPM}$ database was fitted to RS, there was little change in the coefficients to the independent variables in RS: x=−0.377, y=0.527, z=0.00346, $r^2$=0.90, n=94; x=−0.211, y=0.534, z=0.00364, $r^2$=0.94, n=42.

Roberts Sloan Equation:

$$\log J_{MMIPM} = x + y \log S_{IPM} + (1-y) \log S_{AQ} - z \, MW$$

Subsequent to the initial report of the development of RS, the n=42 log $J_{MMIPM}$ database was also fitted to a series/parallel model (J. Pharm. Sci., 2000, 89, 1415). The series/parallel model allowed parallel paths for flux through the membranes to exist that depended (a) only on the aqueous solubility of the permeant, (b) only on the lipid solubility of the permeant or (c) on both the lipid and aqueous solubilities of the permeant as it crossed a series of alternating lipid and aqueous phases. This series/parallel model showed that the parallel path through the membrane that exhibited the highest capacity to carry diffusing molecules across the membranes was the series path. The path that depended only the lipid solubility of the permeant became a major contributor to flux as lipid solubility increased and water solubility decreased for the permeant, but the existence of a path that depended only on the aqueous solubility of the permeant was not necessary to explain the flux data. The high capacity series path was later used as the basis for the biphasic solubility model for flux (Therapeutic Delivery, 2011, 1, 83-105), which suggested that the aqueous phase of the series path, in which the permeant molecule had to dissolve and through which it had to traverse, resided in the area contiguous with the polar head groups of molecules comprising the lipid bilayers in the lipid matrix. Fit of the n=42 log $J_{MMIPM}$ database to the series/parallel equation was no better than the fit to the RS so the simpler RS equation is usually used to predict flux.

The RS equation is quite versatile. When similar data for the flux of molecules through human skin in vitro from water, log $J_{MHAQ}$, n=62 was fitted to RS, where solubility in octanol, OCT, was the lipid independent variable, a good fit was obtained: $r^2$=0.93 (Int. J. Pharm., 2007, 329, 25-36). The log $J_{MHAQ}$ database was eventually increased to n=185 (Int. J. Pharm., 2008, 351, 92-103). Although $r^2$ decreased to 0.84 for n=185, the fact that the data was compiled from 30 different publications and more than 19 different labs each using slightly different protocols makes $r^2$=0.84 the best fit of any reported equation to such a large database. Similarly the fit of the flux through human skin in vitro from a mineral oil, MO, vehicle, log $J_{MHMO}$, gave an excellent fit to RS where solubility in MO was the lipid independent variable: $r^2$=0.93, r=10 (Int. J. Pharm., 2001, 90, 1318-1323). A larger database for the flux through human skin in vitro from mineral oil gave $r^2$=0.80 for an n=30 database (Therapeutic Delivery, 2011, 2, 83-105). Finally the fit of the flux through silicone membrane from water, log $J_{MPAQ}$, to RS, where solubility in OCT was the lipid independent variable, gave $r^2$=0.90 for n=63 (Therapeutic Delivery, 2013, 4, 203-224). Thus regardless of vehicle and regardless of the membrane RS is a good equation with which to predict flux from $S_{AQ}$, $S_{LIPID}$ and MW.

Using the Robert-Sloan equation and the vitamin C data in Table 8 flux values were calculated using coefficients to log $S_{AQ}$, log $S_{OFT}$ and MW for n=185 Log $J_{MHAQ}$ database: x=−2.50, y=0.538, z=0.00402. Using those coefficients, it was observed that the flux of ascorbic acid from 2-AcC1-3-SMC1 ascorbic acid is about ⅓ of that delivered by ascorbic acid itself. However the 2-AcC1-3- SMC1 is stable to oxidation since the enediol is transiently protected. By comparison, the predicted flux of 6-palmitoyl ascorbic acid is about 1/1000 of that of ascorbic acid and its enediol system is not protected so it easily oxidized. Similarly, the flux of ascorbic acid acetonide from its 2-AcC1-3-SMC1 prodrug is about ⅕ that of ascorbic acid acetonide, but again the prodrug is stable to oxidation since the enediol system is protected.

TABLE 8

Flux Values of Vitamin C and derivatives

| | log $S_{OCT}$ | log $S_{AQ}$ | MW | Predicted log $J_{MHAQ}$ |
|---|---|---|---|---|
| 2-AcC1-3-SMC1 ascorbic acid | 1.66 | 2.05 | 290 | −1.82 (0.015) |
| ascorbic acid | 0.62 | 3.22 | 176 | −1.38 (0.042) |
| 6-palmitoyl ascorbic acid | 1.77 | −2.36 | 414 | −4.30 (0.000050) |
| 2-AcC1-3-SMC1 ascorbic acid acetonide | 1.55 | 1.56 | 330 | −2.28 (0.0053) |
| ascorbic acid acetonide | 1.30 | 2.25 | 216 | −1.62 (0.023) |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

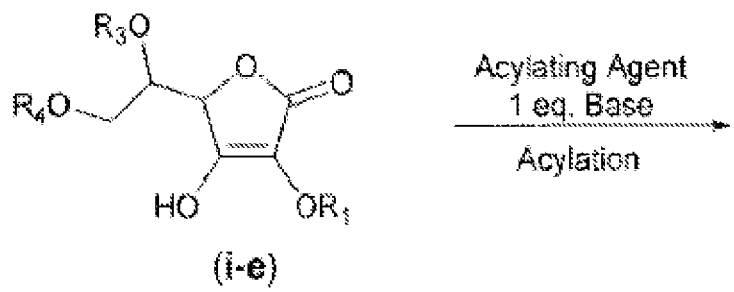

What is claimed is:

1. A compound of Formula (I):

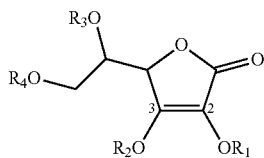

(I)

or a pharmaceutically or cosmetically acceptable salt thereof,
wherein:
  $R_1$ is hydrogen or of Formula (A), Formula (B), or Formula (E):

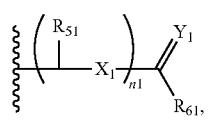

(A)

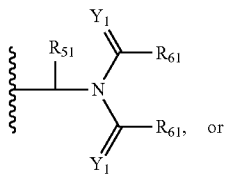

(B)

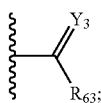

(E)

$R_2$ is of Formula (C), Formula (D), or Formula (E):

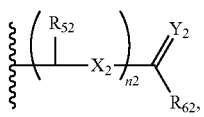

(C)

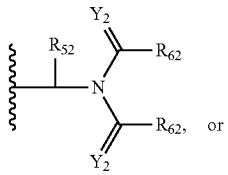

(D)

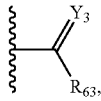

(E)

provided that $R_1$ and $R_2$ are not both of Formula (E);
$R_3$ and $R_4$ are each independently hydrogen or of Formula (E):

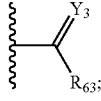

(E)

or optionally $R_3$ and $R_4$ are taken together with the intervening atoms to form an optionally substituted heterocyclic ring;
each of $X_1$ and $X_2$ is independently —O—, or —NR$^{XN}$—;
each instance of $Y_1$, $Y_2$, and $Y_3$ is independently O or NR$^{YN}$;
each instance of $R_{51}$ and $R_{52}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, or optionally substituted heteroaryl;
each instance of $R_{61}$, $R_{62}$, and $R_{63}$ is independently optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, optionally substituted heteroaryl, —OR$^{56O}$, or —N(R$^{56N}$)$_2$, or two $R_{61}$ are taken together with their intervening atoms to form an optionally substituted heterocyclic ring, or two $R_{62}$ are taken together with their intervening atoms to form an optionally substituted heterocyclic ring;

$R_{51}$ and $R_{61}$ are optionally taken together with the intervening atoms to form an optionally substituted heterocyclic ring;

$R_{52}$ and $R_{62}$ are optionally taken together with the intervening atoms to form an optionally substituted heterocyclic ring;

each instance of $R^{XN}$, $R^{YN}$, and $R^{56N}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, or a nitrogen protecting group;

each instance of $R^{56O}$ is independently optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, optionally substituted heteroaryl, or an oxygen protecting group;

$n_1$ is 1, 2, or 3; and $n_2$ is 1, 2, or 3.

2. The compound of claim 1, wherein the compound is of Formula (II):

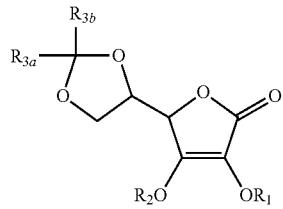

(II)

or a pharmaceutically or cosmetically acceptable salt thereof, wherein each of $R_{3a}$ and $R_{3b}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, or optionally substituted heteroaryl.

3. The compound of claim 2, wherein the compound is of Formula (III-a):

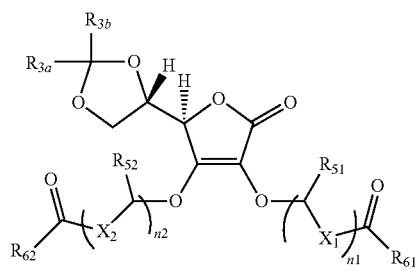

(III-a)

or a pharmaceutically or cosmetically acceptable salt thereof.

4. The compound of claim 2, wherein the compound is of Formula (III-a1-ii):

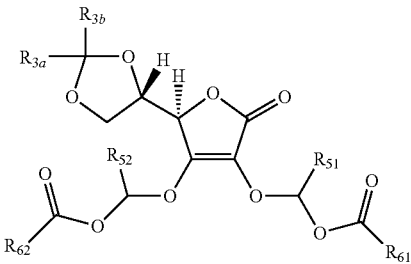

(III-a1-ii)

or a pharmaceutically or cosmetically acceptable salt thereof.

5. The compound of claim 2, wherein the compound is of Formula (III-a2):

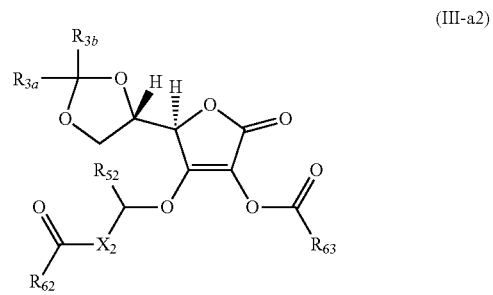

(III-a2)

or a pharmaceutically or cosmetically acceptable salt thereof.

6. The compound of claim 2, wherein the compound is of Formula (III-a2-i):

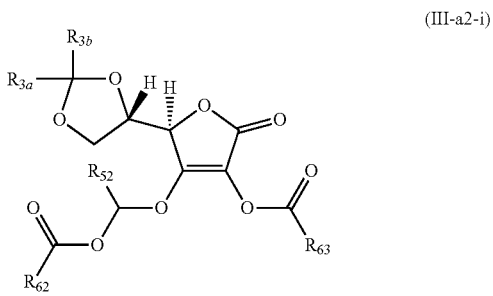

(III-a2-i)

or a pharmaceutically or cosmetically acceptable salt thereof.

7. The compound of claim 1, wherein $R_{61}$ and $R_{62}$ are each independently optionally substituted $C_{1-6}$ alkyl; or a pharmaceutically or cosmetically acceptable salt thereof.

8. The compound of claim 1, wherein the compound is of Formula (III-b):

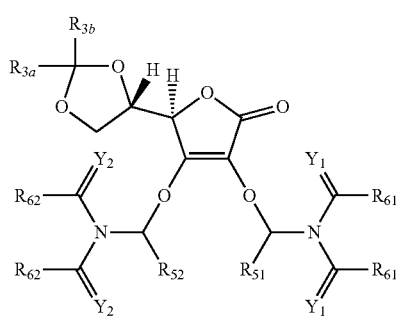

(III-b)

or a pharmaceutically or cosmetically acceptable salt thereof.

9. The compound of claim 1, wherein the compound is of Formula (III-b1) or (III-b2):

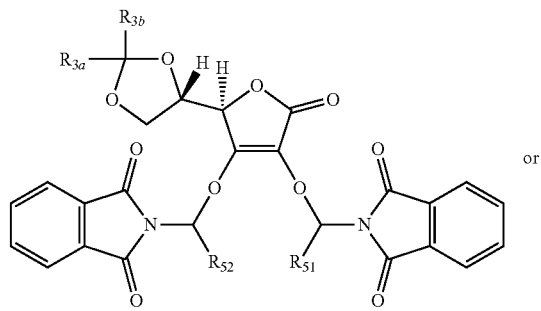

(III-b1)

or

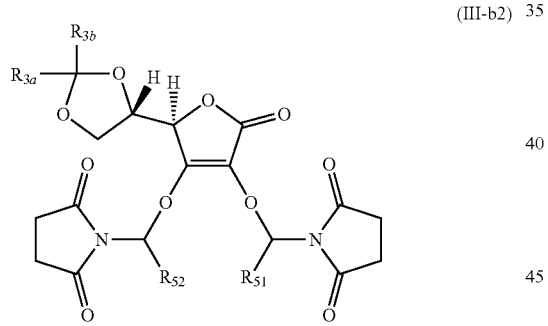

(III-b2)

or a pharmaceutically or cosmetically acceptable salt thereof.

10. The compound of claim 1, wherein $R_{51}$ and $R_{52}$ are independently hydrogen or optionally substituted $C_{1-6}$ alkyl; or a pharmaceutically or cosmetically acceptable salt thereof.

11. A pharmaceutical composition comprising a compound of claim 1, or a pharmaceutically acceptable salt thereof; and a pharmaceutically acceptable excipient.

12. A cosmetic or personal care composition comprising a compound of claim 1, or a cosmetically acceptable salt thereof; and a cosmetically acceptable excipient.

13. A nutraceutical composition comprising a compound of claim 1 and optionally a nutraceutically acceptable carrier.

14. A medical food composition comprising a compound of claim 1 and optionally a nutritionally acceptable carrier.

15. A method of preparing a compound of claim 1 comprising reacting a compound of Formula (i):

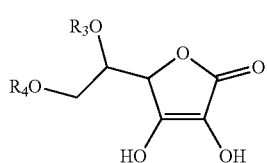

(i)

with a soft alkylating agent of Formula (ii):

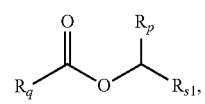

(ii)

wherein $R_{s1}$ is a leaving group;

$R_q$ is optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, $OR^{qO}$, or $N(R^{qN})_2$;

each instance of $R^{qO}$ is independently optionally substituted $C_{1-6}$ alkyl, optionally substituted heteroalkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, optionally substituted heteroaryl, or an oxygen protecting group;

each instance of $R^{qN}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, or a nitrogen protecting group; and $R_p$ is hydrogen or optionally substituted $C_{1-6}$ alkyl.

16. A method of preparing a compound of claim 1 comprising alkylating a compound of formula (i):

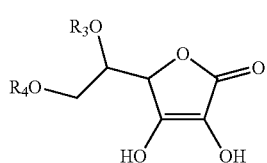

(i)

with a soft alkylating agent of Formula (ii), (iii), or (iv):

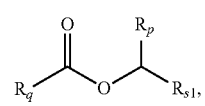

(ii)

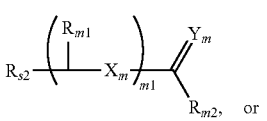

(iii)

(iv)

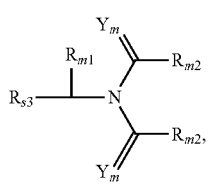

wherein
each of $R_{s1}$, $R_{s2}$ and $R_{s3}$ is independently a leaving group;
$R_q$ is optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, $OR^{qO}$, or $N(R^{qN})_2$;
each instance of $R^{qO}$ is independently optionally substituted $C_{1-6}$ alkyl, optionally substituted heteroalkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, optionally substituted heteroaryl, or an oxygen protecting group;
each instance of $R^{qN}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, or a nitrogen protecting group; and
$R_p$ is hydrogen or optionally substituted $C_{1-6}$ alkyl;
each instance of $X_m$ is independently —O— or —$NR^{XN}$—;
each instance of $Y_m$ is independently O or $NR^{YN}$;
each instance of $R_{m1}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, or optionally substituted heteroaryl;
each instance of $R_{m2}$ is independently optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, optionally substituted heteroaryl, —$OR^{mO}$, or —$N(R^{mN})_2$, or two $R_{m2}$ are taken together with their intervening atoms to form an optionally substituted heterocyclic ring, or one $R_{m1}$ and one $R_{m2}$ in Formula (iv) are taken together with their intervening atoms to form an optionally substituted heterocyclic ring;
each instance of $R^{mN}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted heterocyclyl, optionally substituted heteroaryl, or a nitrogen protecting group;
each instance of $R^{mO}$ is independently optionally substituted $C_{1-6}$ alkyl, optionally substituted heteroalkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, or an oxygen protecting group; and
$m_1$ is independently 1, 2, or 3.

17. A method of making a compound of claim 1, the method comprising steps of:
acylating a compound of Formula (i):

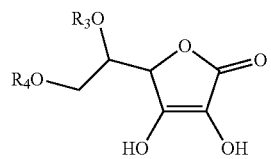

(i)

with an acylating agent to form a compound of Formula (i-c):

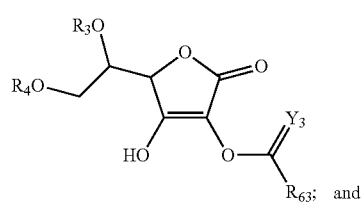

(i-c)

alkylating the compound of Formula (i-c) with a soft alkylating agent of Formula (ii), (iii), or (iv):

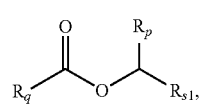

(ii)

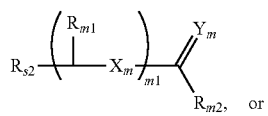

(iii)

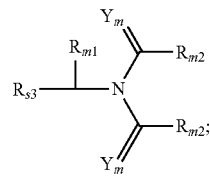

(iv)

wherein
each of $R_{s1}$, $R_{s2}$, and $R_{S3}$ is independently a leaving group;
$R_q$ is optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, $OR^{qO}$, or $N(R^{qN})_2$;
each instance of $R^{qO}$ is independently optionally substituted $C_{1-6}$ alkyl, optionally substituted heteroalkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, optionally substituted heteroaryl, or an oxygen protecting group;
each instance of $R^{qN}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, or a nitrogen protecting group;

$R_p$ is hydrogen or optionally substituted $C_{1-6}$ alkyl;

each instance of $X_m$ is independently —O— or —NR$^{XN}$—;

each of $Y_m$ and $Y_3$ is independently O or NR$^{YN}$;

each instance of $R_{m1}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, or optionally substituted heteroaryl;

each instance of $R_{m2}$ is independently optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, optionally substituted heteroaryl, —OR$^{mO}$, or —N(R$^{mN}$)$_2$, or two $R_{m2}$ are taken together with their intervening atoms to form an optionally substituted heterocyclic ring, or one $R_{m1}$ and one $R_{m2}$ in Formula (iv) are taken together with their intervening atoms to form an optionally substituted heterocyclic ring;

each instance of R$^{mN}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted heterocyclyl, optionally substituted heteroaryl, or a nitrogen protecting group;

each instance of R$^{mO}$ is independently optionally substituted $C_{1-6}$ alkyl, optionally substituted heteroalkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, or an oxygen protecting group;

$R_{63}$ is independently optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, optionally substituted heteroaryl, —OR$^{56O}$, or —N(R$^{56N}$)$_2$; and $m_1$ is independently 1, 2, or 3.

18. A method of making a compound of claim 1, the method comprising steps of:

alkylating a compound of Formula (i):

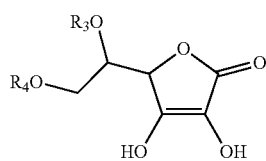
(i)

with a soft alkylating agent of Formula (ii), (iii), or Formula (iv):

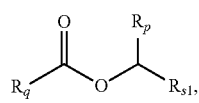
(ii)

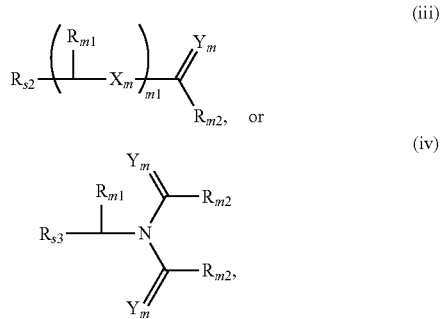
(iii)

(iv)

to form a compound of Formula (i-1x):

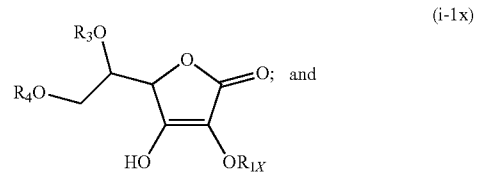
(i-1x)

acylating the compound of Formula (i-1x) with an acylating agent, wherein each of $R_{s1}$, $R_{s2}$, and $R_{s3}$ is independently a leaving group;

$R_q$ is optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, OR$^{qO}$, or N(R$^{qN}$)$_2$;

each instance of R$^{qO}$ is independently optionally substituted $C_{1-6}$ alkyl, optionally substituted heteroalkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, optionally substituted heteroaryl, or an oxygen protecting group;

each instance of R$^{qN}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, or a nitrogen protecting group;

$R_p$ is hydrogen or optionally substituted $C_{1-6}$ alkyl;

each instance of $X_m$ is independently —O— or —NR$^{XN}$—;

each instance of $Y_m$ is independently O or NR$^{YN}$;

each instance of $R_{m1}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, or optionally substituted heteroaryl;

each instance of $R_{m2}$ is independently optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, optionally substituted heteroaryl, —OR$^{mO}$, or —N(R$^{mN}$)$_2$, or two $R_{m2}$ are taken together with their intervening atoms to form an optionally substituted heterocyclic ring, or one $R_{m1}$ and one $R_{m2}$ in Formula (iv) are taken together with their intervening atoms to form an optionally substituted heterocyclic ring;

each instance of $R^{mN}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted heterocyclyl, optionally substituted heteroaryl, or a nitrogen protecting group;

each instance of $R^{mO}$ is independently optionally substituted $C_{1-6}$ alkyl, optionally substituted heteroalkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, or an oxygen protecting group;

$m_1$ is independently 1, 2, or 3;

$R_{1X}$ is of Formula (A) or Formula (B):

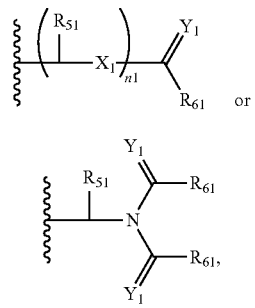

each instance of $X_1$ is independently —O— or —NR$^{XN}$—;

each instance of $Y_1$ is independently O or NR$^{YN}$;

each instance of $R_{51}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, or optionally substituted heteroaryl;

each instance of $R_{61}$ is independently optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, optionally substituted heteroaryl, —OR$^{56O}$, or —N(R$^{56N}$)$_2$, or $R_{51}$ and $R_{61}$ are taken together with the intervening atoms to form an optionally substituted heterocyclic ring;

each instance of R$^{XN}$, R$^{YN}$, and R$^{56N}$ is independently hydrogen, optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted aryl, optionally substituted 3- to 6-membered heterocyclyl, optionally substituted heteroaryl, or a nitrogen protecting group;

each instance of R$^{56O}$ is independently optionally substituted $C_{1-6}$ alkyl, optionally substituted $C_{3-6}$ alkenyl, optionally substituted $C_{3-6}$ alkynyl, optionally substituted $C_{3-6}$ carbocyclyl, optionally substituted 3- to 6-membered heterocyclyl, optionally substituted aryl, optionally substituted heteroaryl, or an oxygen protecting group; and $n_1$ is 1, 2, or 3.

19. The compound of claim 1, wherein the compound is of Formula (III):

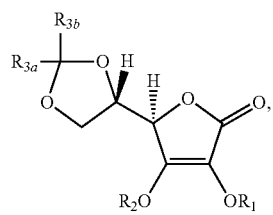

or a pharmaceutically or cosmetically acceptable salt thereof.

20. The compound of claim 1, wherein the compound is of Formula (III-a1):

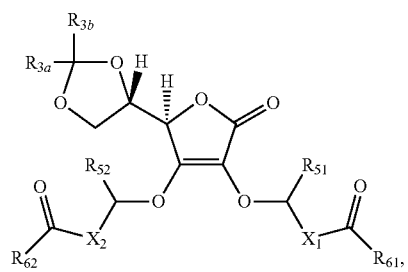

or a pharmaceutically or cosmetically acceptable salt thereof.

21. The compound of claim 1, wherein the compound is of Formula (III-a1-i):

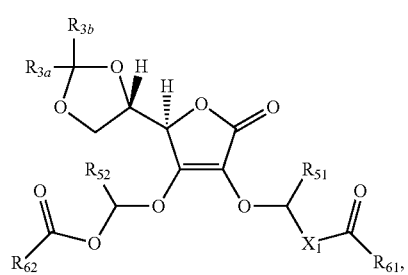

or a pharmaceutically or cosmetically acceptable salt thereof.

22. The compound of claim 1, wherein $R_{61}$ and $R_{62}$ are each independently —O(CH$_2$CH$_2$O)$_s$CH$_3$, wherein s is 1, 2, 3, or 4.

23. The compound of claim 1, wherein the compound is of Formula (E-1):

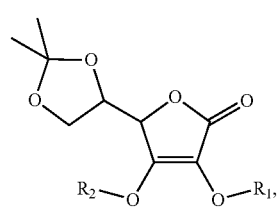

wherein $R_1$ and $R_2$ are as defined below:

| $R_2$ | $R_1$ |
|---|---|
| $CH_2-O-(C=O)CH_3$ | $(C=O)CH_3$ |
| $CH_2-O-(C=O)C_2H_5$ | $CH_2-O-(C=O)C_2H_5$ |
| $CH_2-O-(C=O)C_2H_5$ | $(C=O)C_2H_5$ |
| $CH_2-O-(C=O)C_4H_9$ | $CH_2-O-(C=O)C_4H_9$ |
| $CH_2-O-(C=O)C_4H_9$ | $(C=O)C_4H_9$ |
| $CH_2-O-(C=O)tC_4H_9$ | $CH_2-O-(C=O)tC_4H_9$ |
| $CH_2-O-(C=O)tC_4H_9$ | $(C=O)tC_4H_9$ |
| $CH_2-O-(C=O)C_5H_{11}$ | $CH_2-O-(C=O)C_5H_{11}$ |
| $CH_2-O-(C=O)C_5H_{11}$ | $(C=O)C_5H_{11}$ |
| $CH(CH_3)-O-(C=O)tC_4H_9$ | $CH(CH_3)-O-(C=O)tC_4H_9$ |
| $CH(CH_3)-O-(C=O)tC_4H_9$ | $(C=O)tC_4H_9$ |
| $CH(CH_3)-O-(C=O)CH_3$ | $(C=O)CH_3$ |
| $CH_2-O-(C=O)OC_3H_7$ | $CH_2-O-(C=O)OC_3H_7$ |
| $CH_2-O-(C=O)OC_3H_7$ | $(C=O)OC_3H_7$ |
| $CH_2-O-(C=O)C_6H_4OCH_3$ | $CH_2-O-(C=O)C_6H_4OCH_3$ |
| $CH_2-O-(C=O)C_6H_4OCH_3$ | $(C=O)C_6H_4OCH_3$ |
| $CH_2-O-(C=O)tC_4H_9$ | $(C=O)CH_3$ |
| $CH_2-O-(C=O)tC_4H_9$ | $(C=O)OC_2H_5$ |
| $CH_2-O-(C=O)tC_4H_9$ | $(C=O)OC_3H_7$ |
| $CH_2-O(C=O)CH_3$ | $(C=O)CH_3$ |
| $CH_2-O(C=O)CH_3$ | $(C=O)OC_3H_7$ |
| $CH_2-O(C=O)CH_3$ | $(C=O)O(CH_2CH_2O)_2CH_3$ |

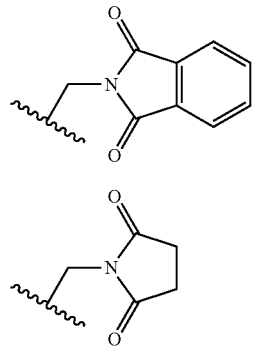

24. The compound of claim 1, wherein the compound is of Formula (E-2):

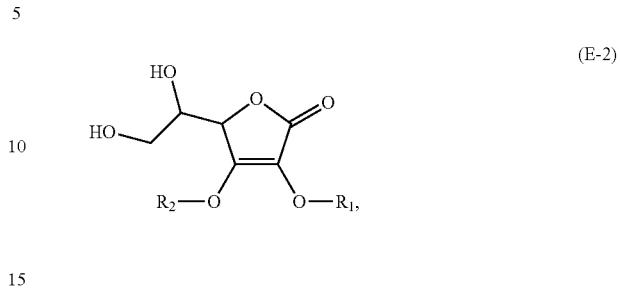

wherein $R_1$ and $R_2$ are as defined below:

| $R_2$ | $R_1$ |
|---|---|
| $CH_2-O-(C=O)C_5H_{11}$ | $(C=O)C_5H_{11}$ |

25. The cosmetic or personal care composition of claim 12, wherein the composition is suitable for topical administration.

* * * * *

UNITED STATES PATENT AND TRADEMARK OFFICE
CERTIFICATE OF CORRECTION

PATENT NO. : 9,550,744 B2
APPLICATION NO. : 15/024504
DATED : January 24, 2017
INVENTOR(S) : Kenneth B. Sloan Page 1 of 2

It is certified that error appears in the above-identified patent and that said Letters Patent is hereby corrected as shown below:

At Column 79, Lines 50 to 57, please replace the scheme:

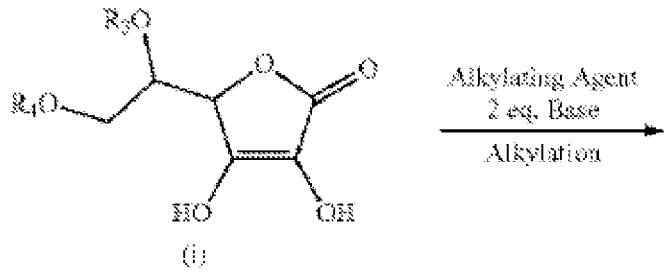

With the scheme:

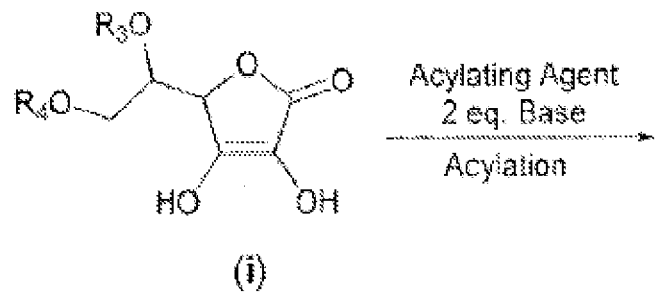

At Column 81, Lines 21 to 26, please replace the scheme:

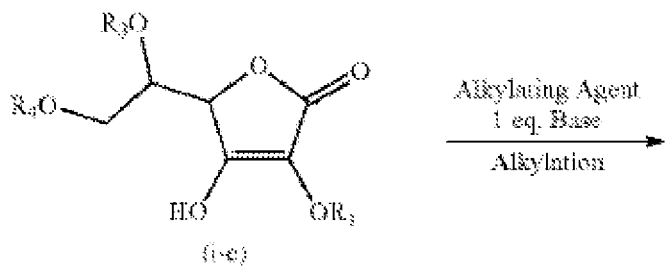

Signed and Sealed this
Third Day of October, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,550,744 B2

With the scheme: